US012691131B2

(12) United States Patent
Rafalko et al.

(10) Patent No.: US 12,691,131 B2
(45) Date of Patent: Jul. 28, 2026

(54) LIPOSOMAL FORMULATIONS, AND METHODS OF USING AND PREPARING THEREOF

(71) Applicant: Glycomine, Inc., San Carlos, CA (US)

(72) Inventors: Agnes Rafalko, San Francisco, CA (US); Teppei Shirakura, San Bruno, CA (US); Samuel Eric Greenberg, Los Gatos, CA (US)

(73) Assignee: Glycomine, Inc., San Carlos, CA (US)

(*) Notice: Subject to any disclaimer, the term of this patent is extended or adjusted under 35 U.S.C. 154(b) by 1005 days.

(21) Appl. No.: 17/593,755

(22) PCT Filed: Mar. 27, 2020

(86) PCT No.: PCT/US2020/025246

§ 371 (c)(1),
(2) Date: Sep. 23, 2021

(87) PCT Pub. No.: WO2020/205530

PCT Pub. Date: Oct. 8, 2020

(65) Prior Publication Data

US 2022/0184107 A1 Jun. 16, 2022

Related U.S. Application Data

(60) Provisional application No. 62/826,874, filed on Mar. 29, 2019.

(51) Int. Cl.

*A61K 31/7032* (2006.01)
*A61K 9/127* (2025.01)
*A61K 9/1272* (2025.01)
*A61K 47/10* (2017.01)
*A61P 3/00* (2006.01)

(52) U.S. Cl.

CPC ........ *A61K 31/7032* (2013.01); *A61K 9/1272* (2013.01); *A61K 47/10* (2013.01); *A61P 3/00* (2018.01)

(58) Field of Classification Search

CPC .......................... A61K 31/7032; A61K 9/1271
See application file for complete search history.

(56) References Cited

U.S. PATENT DOCUMENTS

| | | | | |
|---|---|---|---|---|
| 5,013,556 | A | 5/1991 | Woodle et al. | |
| 7,011,845 | B2 | 3/2006 | Kozbor et al. | |
| 7,108,863 | B2 * | 9/2006 | Zalipsky | A61K 9/1271 424/9.51 |
| 7,491,409 | B1 | 2/2009 | Meers et al. | |
| 10,449,149 | B2 * | 10/2019 | Rafalko | A61K 9/1271 |
| 11,045,419 | B2 * | 6/2021 | Rafalko | A61K 9/1271 |
| 2002/0072121 | A1 | 6/2002 | Lam et al. | |
| 2006/0058249 | A1 | 3/2006 | Tong et al. | |
| 2006/0172003 | A1 | 8/2006 | Meers et al. | |
| 2007/0120280 | A1 | 5/2007 | Anchordoquy et al. | |
| 2009/0054353 | A1 | 2/2009 | Gravier-Pelletier et al. | |
| 2009/0191259 | A1 | 7/2009 | Li et al. | |
| 2011/0014272 | A1 | 1/2011 | Haensler et al. | |
| 2011/0200582 | A1 | 8/2011 | Baryza et al. | |
| 2011/0257233 | A1 | 10/2011 | Cosford et al. | |
| 2012/0135064 | A1 | 5/2012 | Campbell et al. | |
| 2013/0171233 | A1 | 7/2013 | Paulson et al. | |
| 2015/0132369 | A1 | 5/2015 | Rezayat et al. | |
| 2016/0228364 | A1 * | 8/2016 | Rafalko | A61K 31/7028 |
| 2017/0165374 | A1 | 6/2017 | Perkins et al. | |
| 2018/0036239 | A1 | 2/2018 | Raflako et al. | |
| 2022/0110871 | A1 | 4/2022 | Rafalko et al. | |
| 2024/0082155 | A1 | 3/2024 | Rafalko et al. | |
| 2025/0186345 | A1 | 6/2025 | Rafalko et al. | |

FOREIGN PATENT DOCUMENTS

| | | | |
|---|---|---|---|
| CN | 1509166 | A | 6/2004 |
| JP | 2014525461 | A | 9/2014 |
| JP | 2016509572 | A | 3/2016 |
| JP | 2017537650 | A | 12/2017 |
| WO | WO-1998014171 | A1 | 4/1998 |
| WO | WO-2003059322 | A1 | 7/2003 |
| WO | WO-2005000266 | A2 | 1/2005 |
| WO | WO-2006050072 | A2 | 5/2006 |
| WO | WO-2007096532 | A1 | 8/2007 |
| WO | WO-2009118658 | A2 | 10/2009 |
| WO | WO-2013149141 | A1 | 10/2013 |
| WO | WO-2014063757 | A1 | 5/2014 |

(Continued)

OTHER PUBLICATIONS

Daraee et al. "Application of liposomes in medicine and drug delivery", Artificial Cells, Nanomedicine, and Biotechnology 2016, 44, 381-391 (Year: 2016).*
Deng et al. "Controlled gene and drug release from a liposomal delivery platform triggered by X-ray radiation" Nature Communications 2018, 9:2713, p. 1-11 (Year: 2018).*
NIH "D-Mannose 1-phosphate" 2024, National Library of Medicine, PubChem https://pubchem.ncbi.nlm.nih.gov/compound/D-Mannose-1-phosphate (accessed Sep. 23, 2024) (Year: 2024).*
Alwael et al., (2011). "Liquid Chromatographic Profiling of Monosaccharide Concentrations in Complex Cell-Culture Media and Fermentation Broths," Analytical Methods, 3(1):62-69.
Bones et al., (2011). Identification of N-Glycans Displaying Mannose-6-Phosphate and their Site of Attachment on Therapeutic Enzymes for Lysosomal Storage Disorder Treatment, Analytical Chemistry, 83:5344-5352.

(Continued)

*Primary Examiner* — Bethany P Barham
*Assistant Examiner* — Judith Marie Kamm
(74) *Attorney, Agent, or Firm* — Morrison & Foerster LLP

(57) ABSTRACT

The disclosure provides phosphorylated carbohydrate replacement therapies (CRT) that include compositions of phosphorylated carbohydrates and phospholipids, as well as methods for preparing such compositions. Such compositions are suitable for pharmaceutical delivery of phosphorylated carbohydrates to cell interior, endoplasmic reticulum, and Golgi, and can be used for treating CDG type I and CDG type II diseases as well as other metabolic disorders.

16 Claims, 5 Drawing Sheets

(56) References Cited

FOREIGN PATENT DOCUMENTS

| | | | |
|---|---|---|---|
| WO | WO-2015053910 | A2 | 4/2015 |
| WO | WO-2020205530 | A1 | 10/2020 |

OTHER PUBLICATIONS

Chan et al., (2016). "A Mouse Model of a Human Congenital Disorder of Glycosylation Caused by Loss of PMM2," Human Molecular Genetics, 25(11):2182-2193.
Colletier et al., (2002). "Protein Encapsulation in Liposomes: Efficiency Depends on Interactions between Protein and Phospholipid Bilayer," BMC Biotechnology Electronic Resource, 2(9):1-8.
Eklund et al., (2005). "Hydrophobic Man-1-P Derivatives Correct Abnormal Glycosylation in Type I congenital disorder of Glycosylation Fibroblasts," Glycobiology, 15(11):1084-1093.
Eklund et al., (2010). "Congenital Disorders of Glycosylation and Their Effects on the Liver Fibrocystic Diseases of the Liver," J Hepatol, 52(3):432-40.
Extended European Search Report received for European Patent Application No. 14851464.9, mailed on Mar. 16, 2017, 9 Pages.
Freeze (2009). "Towards a Therapy for Phosphomannomutase 2 Deficiency, The Defect in CDG-Ia Patients," Biochimica Et Biophysica Acta, 1792:835-840.
Freeze et al., (2012). "Neurology of Inherited Glycosylation Disorders," The Lancet Neurology, 11(5):453-466.
Fujiwara et al., (2010). "Intracellular Fate of Octaarginine-Modified Liposomes in Polarized MDCK Cells," International Journal of Pharmaceutics, 386:122-130.
Gao et al., (2006). "Non-Radioactive Analysis of Lipid-Linked Oligosaccharide Compositons by Fluorophore-Assisted Carbohydrate Electrophoresis," Methods in Enzymology, 415:3-20.
Garbuzenko et al., (2005). "Effect Of Grafted PEG On Liposome Size And On Compressibility And Packing Of Lipid Bilayer," Chemistry And Physics Of Lipids, 135(2):117-129.
Hardré et al., (2007). "Mono, Di and Tri-Mannopyranosyl Phosphates as Mannose-1-Phosphate Prodrugs for Potential CDG-Ia Therapy," Bioorganic & Medicinal Chemistry Letters, 17:152-155.
Hubbard et al., (1980). "Synthesis of the N-linked Oligosaccharideos of Glycoproteins," The Journal of Biological Chemistry, 255(24):11782-11793.
Huwyler et al., (1997). "Receptor Mediated Delivery of Daunomycin Using Immunoliposomes: Pharmacokinetics and Tissue Distribution in the Rat1," The Journal of Pharmacology and Experimental Therapeutics, 282(3):1541-1546.
Immordino et al., (2006). "Stealth Liposomes: Review of the Basic Science, Rationale, and Clinical Applications, Existing and Potential," International Journal of Nanomedicine, 1(3):297-315.
International Preliminary Report on Patentability received for PCT Patent Application No. PCT/US2014/055921, mailed on Mar. 31, 2016, 6 pages.
International Search Report and Written Opinion received for PCT Patent Application No. PCT/US2014/055921, mailed on Apr. 23, 2015, 8 pages.
International Search Report and Written Opinion received for PCT Patent Application No. PCT/US2020/025246, mailed on Jul. 1, 2020, 9 pages.
International Search Report and Written Opinion received for PCT Patent Application No. PCT/US2021/24517, mailed on Jun. 8, 2021, 14 pages.
Jaeken et al., (2007). "Congenital Disorders of Glycosylation: A Rapidly Expanding Disease Family," Annual review of genomics and human genetics, 8:261-278.
Jaeken et al., (2008). "On the Nomenclature of Congenital Disorders of Glycosylation (CDG)," Journal of Inherited Metabolic Disease, 31:669-672.
Kjaergaard et al., (1998). "Failure of Short-Term Mannose Therapy of Patients with Carbohydrate-Deficient Glycoprotein Syndrome Type 1A," Acta paediatrica, 87:884-888.
Körner et al., (1998). "Abnormal Synthesis of Mannose 1-Phosphate Derived Carbohydrates in Carbohydrate-Deficient Glycoprotein Syndrome Type I Fibroblasts with Phosphomannomutase Deficiency," Glycobiology, 8(2):165-171.
Koshkaryev et al., (2011). "Targeting of Lysosomes by Liposomes Modified with Octadecyl-rhodamine B," Journal of Drug Targeting, 19(8):606-614.
Leroy, (2006). "Congenital Disorders of N-Glycosylation including Diseases Associated with O- As Well As N-Glycosylation Defects," Pediatric Research, 60(6):643-656.
Mayatepek et al., (1998). "Mannose supplementation in Carbohydrate-Deficient Glycoprotein Syndrome Type I and Phosphomannomutase Deficiency," European journal of pediatrics, 157:605-612.
Niehues et al., (1998). "Carbohydrate-Deficient Glycoprotein Syndrome Type Ib. Phosphomannose Isomerase Deficiency and Mannose Therapy," The Journal of clinical investigation, 101(7):1414-1420.
Non-Final Office Action received for U.S. Appl. No. 15/788,591, mailed on Sep. 21, 2018, 12 pages.
Notice of Allowance received for U.S. Appl. No. 15/788,591, mailed on Jun. 14, 2019, 8 pages.
Pollock et al., (2010). "Uptake and Trafficking of Liposomes to the Endoplasmic Reticulum," The FASEB Journal, 24(6):1866-1878.
Rutschow et al., (2002). "Membrane-Permeant Derivatives of Mannose-1-phosphate," Bioorganic & Medicinal Chemistry, 10:4043-4049.
Schaftingen et al., (1995). "Phosphomannomutase Deficiency is a Cause of Carbohydrate-Deficient Glycoprotein Syndrome Type I," FEBS Letters, 377:318-320.
Schneider et al., (2012). "Successful Prenatal Mannose Treatment for Congenital Disorder of Glycosylation-Ia in Mice," Nature Medicine, 18(1):71-73.
Sparks et al., (2005). "Congenital Disorders of N-Linked Glycosylation and Multiple Pathway Overview," GeneReviews, Available Online at <https://www.ncbi.nlm.nih.gov/books/NBK1332/?report=printable> p. 1-24.
Sugimoto et al., (1995). "Oligomannose-Coated Liposomes As An Adjuvant For The Induction Of Cell-Mediated Immunity," FEBS Letters, 363:53-56.
Thiel et al., (2006). "Targeted Disruption of the Mouse Phosphomannomutase 2 Gene Causes Early Embryonic Lethality," Molecular and Cellular Biology, 26(15):5615-5620.
Torchilin et al., (2003). "TAT-Liposomes: A Novel Intracellular Drug Carrier," Current Protein and Peptide Science, 4:133-140.
Torchilin et al., (2005). "Recent Advances with Liposomes as Pharmaceutical Carriers," Nature Reviews. Drug Discovery, 4:145-160.
Wang et al., (2013). "A General Strategy for the Chemoenzymatic Synthesis of Asymmetrically Branched N-Glycans," Science, 341:379-383.
Weerapana et al., (2005). "Investigating Bacterial N-Linked Glycosylation: Synthesis and Glycosyl Acceptor Activity of the Undecaprenyl Pyrophosphate-Linked Bacillosamine," Journal of the American Chemical Society, 127(40):13766-13767.
Westmark et al., (1994). "Boronic Acids Selectively Facilitate Glucose Transport Through a Lipid Bilayer," Journal of the American Chemical Society, 116(20):9343-9344.
Westphal (2002). "A frequent Mild Mutation in ALG6 May Exacerbate the Clinical Severity of Patients with Congenital Disorder of Glycosylation Ia (CDG-Ia) caused by Phosphomannomutase Deficiency," Human Molecular Genetics, 11(5):599-604.
Auguste et al., (2003). "Association of hydrophobically-modified poly(ethylene glycol) with fusogenic liposomes," Biochimica Et Biophysica Acta, 1616(2):184-195.
Carrillo et al., (2018). "GNE myopathy: etiology, diagnosis, and therapeutic challenges," Neurotherapeutics, 15:900-914.
Extended European Search Report received for European Patent Application No. 21185152.2, mailed on May 3, 2022, 8 Pages.
Extended European Search Report received for European Patent Application No. 20782039.0, mailed on Mar. 16, 2023, 14 Pages.
Korb et al., (2008). "Current data on ATP-containing liposomes and potential prospects to enhance cellular energy status for hepatic applications," Critical Reviews In Therapeutic Drug Carrier Systems, 25(4):305-345.

(56) References Cited

OTHER PUBLICATIONS

Li et al., (2014). "A review on phospholipids and their main applications in drug delivery systems," Asian Journal of Pharmaceutical Sciences, 10(2):81-98.
Liu et al., (2013). "Acute bioenergetic intervention or pharmacological preconditioning protects neuron against ischemic injury," J Exp Stroke Transl Med, 6:7-17, 11 pages.
Partial supplementary European Search Report received for European Patent No. 20782039.0 mailed on Dec. 13, 2022, 18 pages.
Pogoryelova et al., (2018). "GNE myopathy: from clinics and genetics to pathology and research strategies," Orphanet Journal of Rare Diseases, (2018) 13:70, 15 pages.
Rouquette et al., (2019). "Adenosine and lipids: A forced marriage or a love match?" Advanced Drug Delivery Reviews, 151-152, 21:233-244.
Search Report received for Singaporean Patent Application No. 11202110623P, completed Mar. 16, 2023, 5 pages.
Streicher-Scott et al., (1994). "The Reconstituted Mitochondrial Adenine Nucleotide Translocator: Effects of Lipid Polymorphism," Archives Of Biochemistry And Biophysics, 315(2):548-554.
Tep et al., (2009). "Formulation and evaluation of ATP containing liposomes including lactosylated ASGPr ligand," Journal Of Liposome Research., 19(4):287-300.
Nonaka et al., (1981). "Familial distal myopathy with rimmed vacuole and lamellar (myeloid) body formation," J Neurol Sci, 51(1):141-55. Abstract Only.
Nogueira et al., (2015). "Design of liposomal formulations for cell targeting," Colloids and Surfaces B: Biointerfaces, 136:514-526.
U.S. Appl. No. 18/777,142 (Agnes et al.), filed on Jul. 18, 2024, titled "Pharmaceutical Preparation of Carbohydrates for Therapeutic Use."
El-Sayed et al., (2009). "Delivery of Macromolecules Using Arginine-Rich Cell-Penetrating Peptides: Ways to Overcome Endosomal Entrapment," The AAPS Journal, 11(1): 13-22.
Scherphof et al., (2001). "The Role of Heptocytes in the Clearance of Liposomes from the Blood Circulation," Progress in Lipid Research, 40:149-166.
Bulbake et al., (2017). "Liposomal Formulations in Clinical Use: An Updated Review," Pharmaceutics, 9, 12, 33 pages.
Ishida et al., (2006). "Accelerated blood clearance of PEGylated liposomes upon repeated injections: Effect of doxorubicin-encapsulation and high dose first injection," Journal Of Controlled Release, 115(3):251-258.
Partial European Search Report received for European Patent Application No. 25157136.0, mailed on Jul. 30, 2025, 16 Pages.
National Center for Biotechnology Information, (2025). "D-Mannose," PubChem, available online at <https://pubchem.ncbi.nlm.nih.gov/compound/D-Mannose>, 49 pages.
National Center for Biotechnology Information, (2025). "Doxorubicin," PubChem, available online at <https://pubchem.ncbi.nlm.nih.gov/compound/Doxorubicin>, 117 pages.
National Center for Biotechnology Information, (2025). "Etoposide," PubChem, available online at <https://pubchem.ncbi.nlm.nih.gov/compound/Etoposide>, Retrieved Sep. 18, 2025, 107 pages.
Nordström et al., (2021). "Quantitative Cryo-TEM Reveals New Structural Details of Doxil-Like PEGylated Liposomal Doxorubicin Formulation," Pharmaceutics, 13, 123, 19 pages.

* cited by examiner

LIPOSOMAL FORMULATIONS, AND METHODS OF USING AND PREPARING THEREOF

CROSS-REFERENCE TO RELATED APPLICATIONS

This application is a U.S. National Phase Patent Application of PCT/US2020/025246, filed Mar. 27, 2020, which claims priority to and the benefit of U.S. Provisional Patent Application No. 62/826,874, filed Mar. 29, 2019, each of which is incorporated herein by reference in its entirety.

FIELD

The present invention relates to compositions containing carbohydrates encapsulated in a liposome for delivery to the cell interior, methods of delivering the encapsulated carbohydrates into the interior of cells, and methods of using such compositions for treating diseases and disorders, such as congenital disorders of glycosylation (CDG). For example, the present invention relates to methods for preparation of carbohydrates and liposomes for pharmaceutical delivery to cell interior, endoplasmic reticulum (ER), and Golgi.

BACKGROUND

Glycosylation, the enzymatic attachment of carbohydrates (glycans) to proteins and lipids, is a co-translational and post-translational modification (PTM) that is more common than any other PTM as it applies to a majority of proteins synthesized in the rough endoplasmic reticulum (ER). Glycosylation plays a critical role in a variety of biological processes of membrane and secreted proteins. In the ER, glycosylation defines the protein structure and folding and acts as a quality control mechanism that dictates the export of properly folded proteins to Golgi or targets misfolded ones for degradation. Glycan moieties may also act as ligands for cell surface receptors to mediate cell attachment or stimulate signal transduction pathways. Congenital disorders of glycosylation, also known as CDG syndromes, are a group of rare genetic diseases where tissue proteins and/or lipids carry defective glycosylation and/or lack of glycosylation. These diseases are linked to numerous enzymatic deficiencies and often times cause severe, sometimes fatal, impairments of the nervous system, muscles, intestines, and several other organ systems.

Common clinical symptoms in children with CDG include hypotonia, developmental delay, failure to thrive, hepatic dysfunction, coagulopathy, hypothyroidism, esotropia, abnormal fat pattern and inverted nipples, hypoglycemia, seizure, cerebellar hypoplasia, and stroke-like episodes in a developmentally delayed child. At an older age, in adolescence or adulthood, the presentation may include ataxia, cognitive impairment, the absence of puberty in females, small testes in males, retinitis pigmentosa, scoliosis, joint contractures, and peripheral neuropathy.

CDG may be classified into two groups: CDG type I and CDG type II. CDG type I is characterized by defects in the initial steps of N-linked protein glycosylation, i.e., biosynthesis of dolichol pyrophosphate linked oligosaccharide (DO), which occur in the ER, or transfer of the DLO to asparagine residues of nascent polypeptides. CDG type II involves defects in further processing (synthetic or hydrolytic) of the protein-bound glycan. Currently, twenty-two CDG type I and fourteen type II variants have been identified. One of the most common subtypes of CDG is CDG-Ia (approximately 70% of all CDG cases), which is characterized by loss or reduction of phosphomannomutase 2 (PMM) activity leading to the deficiency or insufficiency in intracellular N-glycosylation (Jaeken et al. *J. of Inherit. Met. Disease.* 2008, 31: 669-672). PMM is responsible for the conversion of mannose-6-phosphate to mannose-1-phosphate.

Although several different approaches of developing therapies for CDG have been explored, researchers continue their search for a suitable cure or a therapy for mitigating the disease itself. Existing treatments for manifestations include, for example, nutritional supplements, tube feeding, and a wide range of therapies that attempt to treat gastroesophageal reflux, persistent vomiting, developmental delays, ocular abnormalities, and hypothyroidism. Patients also require intravenous (IV) hydration and physical therapy for stroke-like episodes. Adults with orthopedic symptoms often require wheel chairs, transfer devices, and surgical treatment for scoliosis (Sparks et al., Disorders of Glycosylation Overview. 2005 In: Pagon R A, Adam M P, Bird T D, et al., editors. GeneReviews™. Seattle (Wash.): University of Washington, Seattle; 1993-2013).

Currently, CDG-Ib is one known CDG for which a treatment is available, namely oral D-mannose administration. However, such therapy may not be as effective in treating CDG-Ia patients and there are currently limited treatment options for other CDG type I subtypes and CDG type II diseases. One of the reasons for the lack in established therapy for CDG-I disorders may be due to the plethora of heterogeneous clinical phenotypes presented that do not show a direct correlation to the PMM enzyme activity.

Patients suffering from a reduction in PMM activity have reduced productions of mannose-1-phosphate (Man-1-P), associated with symptoms of multivisceral impairments. In order to overcome PMM production deficiency, it is important to supply downstream enzymes with the required substrate (i.e., Man-1-P). However, the delivery and maintenance of such a systemic supply of Man-1-P is problematic, as extracellular enzymes within bodily fluids degrade Man-1-P when delivered exogenously by oral or intravenous administration. Another problem with exogenously delivered Man-1-P is that its high polarity prevents Man-1-P from penetrating into the cell interior (i.e., cytosol) and thus treating the deficiency in PMM production.

Derivatives of the polar Man-1-P can be synthesized to make Man-1-P more cell-permeable (US Patent Publication No. 2009/0054353). This approach, however, is also problematic, as the cell-permeable Man-1-P derivatives have been shown to be either unstable for clinical use or cytotoxic via the by-products of the Man-1-P derivatives (Eklund et al., *Glycobiology* 2005, 15: 1084-1093; Rutschow et al. *Bioorg Med Chem* 2002, 10: 4043-4049; and Hardre et al., *Bioorg Med Chem Lett* 2007, 17: 152-155).

Other potential therapies have focused on inhibiting enzymes that catabolize mannose-6-phosphate (Man-6-P), a precursor to Man-1-P, via the inhibition of phosphomannose isomerases (PMI). The approach focuses on forcing the reaction towards optimizing homeostasis, which with the use of PMI inhibitors, would have been skewed toward production of Man-6-P. These approaches, however, are ineffective as clinical treatment options due to their associated toxicity, off-target side effects, and poor selective tissue penetration.

Another potential solution is to use a delivery vehicle (e.g., lipid particles) to encapsulate and deliver Man-1-P to the cell interior (see WO 2015/053910). However, due to the high charge and polarity of phosphorylated carbohydrates in general, the optimal delivery vehicle must overcome challenges of stability, phosphorylated carbohydrates loading rate and concentration, toxicity, and delivery efficiency.

Accordingly, unmet needs exist for improved compositions and methods for delivering phosphorylated carbohydrates, such as Man-1-P and Man-6-P, to the cell interior in order to treat disorders, such as a congenital disorder of glycosylation (CDG), to subjects (including, for example, humans) in need of such treatment.

BRIEF SUMMARY

The present disclosure meets the unmet needs described above by providing compositions and kits comprising phosphorylated carbohydrates encapsulated by certain liposomes that address the phosphorylated carbohydrate loading efficiency, cytotoxicity, and stability problems associated with either permeabilizing cells or encapsulating phosphorylated carbohydrates using lipid particles. Such phosphorylated carbohydrates may be endogenous carbohydrates, including, for example, mannose-1-phosphate. By utilizing endocytotic pathways, these liposomes can enter the cell interior and deliver the phosphorylated carbohydrate into the cytosol of a cell. This use of certain liposomes to encapsulate phosphorylated carbohydrates, facilitates simultaneously the ease of therapy, allowing for higher dosages of the phosphorylated carbohydrate to reach the biochemical glycosylation pathway, as well as potential easement on administration. In some aspects, the disclosure provides methods for preparation of phosphorylated carbohydrates encapsulated by certain liposomes for pharmaceutical delivery to cell interior, endoplasmic reticulum, and Golgi. The disclosure provides phosphorylated carbohydrate replacement therapies for, but not limited to, treating diseases of CDG type I and CDG type II.

The present disclosure also addresses unmet needs related to effective therapeutics for diseases, such as diseases of CDG, as well as issues related to the delivery of such therapeutics. In some aspects, the disclosure provides a method of delivering phosphorylated carbohydrates such as mannose-1-phosphate to the cytosol of cells. Without wishing to be bound by any theory, it is believed that such method of deliver the phosphorylated carbohydrates (e.g., as part of a medicament) would bypass the work of genetically defective cytosolic enzymes, namely phosphomannomutase (PMM) and phosphomannose isomerase (PMI), which are found prevalent in CDG I disorders.

In some embodiments, the present disclosure provides a composition comprising a liposome comprising:

- i) 1,2-dioleoyl-sn-glycero-3-phosphoethanolamine (DOPE);
- ii) one or more stabilizer selected from
  - (a) one or more phospholipid having a polar head group selected from the group consisting of glycerol, choline, phosphate and serine and a fatty acid tail comprising a $C_{10-28}$ aliphatic chain, or
  - (b) an acidic cholesterol ester, or a mixture of (a) and (b); and
- iii) PEG conjugated to at least one phospholipid; and at least one endogenous phosphorylated carbohydrate, wherein the at least one endogenous phosphorylated carbohydrate is encapsulated in the liposome.

In some embodiments, the at least one phospholipid conjugated to PEG is 1,2-distearoyl-sn-glycero-3-phosphoethanolamine (DSPE). In some embodiments, the one or more stabilizers comprises 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), or 1,2-dioleoyl-sn-glycero-3-phospho-L-serine (DOPS). In some embodiments, DOPE is present at a concentration of up to 80 mol %. In some embodiments, the liposome further comprises cholesterol.

In some embodiments, the present disclosure provides a composition comprising a liposome comprising

- i) N-dodecanoyl-1,2-di-(9Z-octadecenoyl)-sn-glycero-3-phosphoethanolamine (N-C12-DOPE); and
- ii) 1,2-dioleoyl-sn-glycero-3-phosphocholine (DOPC); and at least one phosphorylated endogenous carbohydrate, wherein the at least one endogenous carbohydrate is encapsulated in the liposome.

In some embodiments, the liposome further comprises PEG conjugated to at least one phospholipid. In some embodiments, the at least one phospholipid conjugated to PEG is 1,2-distearoyl-sn-glycero-3-phosphoethanolamine (DSPE). In some embodiments, the liposome further comprises cholesterol.

In some embodiments, the at least one endogenous phosphorylated carbohydrate is a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof. In some embodiments, the at least one endogenous phosphorylated carbohydrate is a phosphorylated mannose. In some embodiments, the phosphorylated mannose is mannose-1-phosphate. In some embodiments, the phosphorylated mannose is mannose-6-phosphate. In some embodiments, the endogenous phosphorylated carbohydrate is present at a concentration of about 0.1-75 mM.

Other aspects of the present disclosure relate to a pharmaceutical composition containing a composition of any of the preceding embodiments, and a pharmaceutically acceptable carrier.

Other aspects of the present disclosure relate to a kit containing a composition of any of the preceding embodiments for use in any of the methods described herein.

Other aspects of the present disclosure relate to a method for delivering a phosphorylated carbohydrate to a subject in need thereof, by administering to the subject a composition of any of the preceding embodiments. In some embodiments, the composition is administered orally, topically, dermally, nasally, intravenously, intramuscularly, intraperitoneally, intracerobrospinally, intracranially, intraspinally, subcutaneously, intraarticularly, intrasynovialy, or intrathecally.

Other aspects of the present disclosure relate to a method for delivering a phosphorylated carbohydrate to a cell interior of a subject in need thereof, by administering to the subject a composition of any of the preceding embodiments. In some embodiments, the composition is administered orally, topically, dermally, nasally, intravenously, intramuscularly, intraperitoneally, intracerobrospinally, intracranially, intraspinally, subcutaneously, intraarticularly, intrasynovialy, or intrathecally.

Other aspects of the present disclosure relate to a method for treating a congenital disorder of glycosylation (CDG) in a subject in need thereof, by administering to the subject a composition of any of the preceding embodiments. In some embodiments, the congenital disorder of glycosylation (CDG) is selected from a CDG type I disorder, a CDG-Ia disorder, a CDG type II disorder, a CDG-IIc disorder, and a CDG-IIf disorder. In some embodiments, the congenital disorder of glycosylation (CDG) is a CDG-Ia disorder. In some embodiments, the composition is administered orally, topically, dermally, nasally, intravenously, intramuscularly, intraperitoneally, intracerobrospinally, intracranially, intraspinally, subcutaneously, intraarticularly, intrasynovialy, or intrathecally.

DESCRIPTION OF THE DRAWINGS

The present application can be best understood by reference to the following description taken in conjunction with the accompanying figures included in the specification.

DETAILED DESCRIPTION

Figure 1:
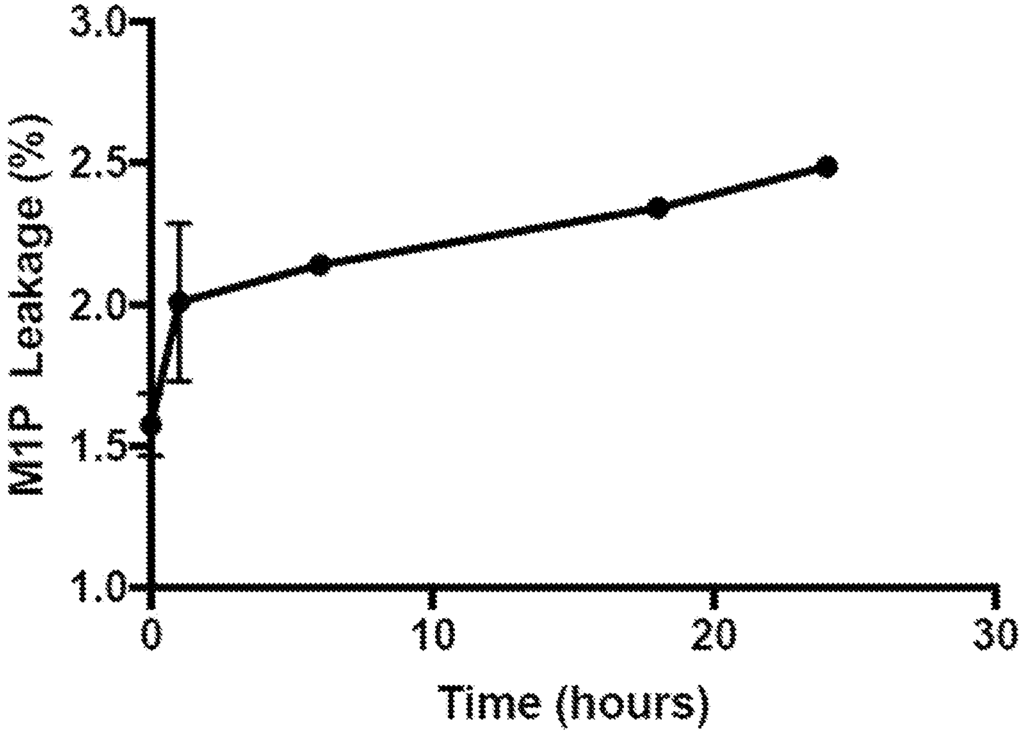
FIG. 1 depicts the in vitro M1P leakage profile under physiological conditions; n=3.

The present disclosure is based on the inventors' discovery that certain liposome compositions are effective at encapsulating phosphorylated carbohydrates and delivering phosphorylated carbohydrates to cell interior. Provided herein are compositions of phosphorylated carbohydrates encapsulated by these liposomes that are capable of delivering phosphorylated carbohydrates to a cell interior including, for example, the cytoplasm, endoplasmic reticulum, and Golgi. In some embodiments, the phosphorylated carbohydrate is mannose-1-phosphate or mannose-6-phosphate. Also provided here are pharmaceutical compositions and kits containing these compositions. Also provided here are methods for delivering a phosphorylated carbohydrate to a cell interior or treating a congenital disorder of glycosylation (CDG) of a subject in need thereof, by administering to the subject such compositions.

The high negative charge and polarity generally make it difficult for phosphorylated carbohydrates to pass through the membrane of the liposomes. This difficulty can limit the method and timing of the encapsulation of phosphorylated carbohydrates into the liposomes.

Unless defined otherwise, all scientific and technical terms are understood to have the same meaning as commonly used in the art to which they pertain. For the purpose of the present disclosure, the following terms are defined.

The term "about" as used herein refers to the usual error range for the respective value readily known to the skilled person in this technical field. Reference to "about" a value or parameter herein includes (and describes) embodiments that are directed to that value or parameter per se. For example, "about x" includes and describes "x" per se. In some embodiments, the term "about" when used in association with a measurement, or used to modify a value, a unit, a constant, or a range of values, refers to variations of +/−2%.

Reference to "between" two values or parameters herein includes (and describes) embodiments that include those two values or parameters per se. For example, description referring to "between x and y" includes description of "x" and "y" per se. Further, it should also be understood that "between x and y" can also be expressed as "about x to y" or "about x-μ".

As used herein, molar percent is also referred to as "mol %".

As used herein, the singular forms "a," "an," and "the" include plural reference unless the context clearly indicates otherwise.

Compositions

Provided herein are compositions comprising a liposome comprising one or more lipid particles and at least one phosphorylated carbohydrate, wherein the at least one phosphorylated carbohydrate is encapsulated in the liposome.

Liposomes

In some embodiments, the liposome is a vesicle composed of a lamellar phase lipid bilayer. Any suitable liposome known in the art may be used. In some embodiments, the liposome has a lamellar nanostructure.

Liposomes of the present disclosure may be prepared by any suitable method known in the art and disclosed herein. Examples of suitable methods for preparing liposomes include, for example, disrupting biological membranes, such as by mechanical dispersion including sonication, thin-film hydration, emulsions, French pressure cell, extrusion, and reconstitution of dried vesicles; solvent dispersion including ethanol injection, ether injection, double emulsion, reverse phase, and vaporization; and detergent removal methods.

In certain embodiments, the liposome is a stealth liposome that may be immunotolerant. In some embodiments, a stealth liposome is a liposome that is capable of avoiding detection by a subject's immune system. As such, a stealth liposome may be immunotolerant. For example, the subject may be a human.

When an active agent or therapeutic agent, such as a carbohydrate of the present disclosure, is encapsulated in a liposome, the liposome provides such active agent or therapeutic agent with full encapsulation, partial encapsulation, or both. In some variations, at least a portion of the carbohydrate may be encapsulated by a liposome and localized within the core of a liposome and/or within the inner surface (e.g., the membrane) of a liposome. Alternatively, in other variations, the entire carbohydrate may be encapsulated by a liposome and localized within the core of a liposome and/or within the inner surface (e.g., the membrane) of a liposome.

Liposomes of the present disclosure contain one or more lipids. In some embodiments, the lipid comprises a substance of biological or synthetic origin that is soluble or partially soluble in organic solvents or which partitions into a hydrophobic environment when present in aqueous phase. In some variations, lipids may be divided into at least three classes: (1) simple lipids which include, for example, fats, oils, and waxes; (2) compound lipids which include, for example, phospholipids and glycolipids; and (3) derived lipid which include, for example, steroids.

In some variations, the lipid may be a neutral lipid or an amphiphilic lipid. In some embodiments, a neutral lipid is a lipid that exists either in an uncharged or neutral zwitterionic form at a selected pH. At physiological pH, such lipids may include, for example, diacylphosphatidylcholine, diacylphosphatidylethanolamine, ceramide, sphingomyelin, cephalin, cholesterol, cerebrosides, and diacylglycerols. In some embodiments, an amphiphilic lipid is a lipid that contains both polar, water-soluble groups and non-polar, water-insoluble groups.

Suitable lipids include, for example, bilayer-forming lipids, non-bilayer-forming lipids, amphiphilic lipids, naturally-occurring lipids, phospholipids, glycerolipids, sphingolipids, phosphatidylglycerol, phosphatidic acid, lysolipids, fatty acids, sphingomyelin, glycosphingolipids, glucolipids, glycolipids, sulphatides, lipids with ether-linked and ester-linked fatty acids, polymerizable lipids, synthetic lipids, and semi-synthetic lipids. Synthetic or semi-synthetic lipids may be produced via deacylation or reacylation of natural lipids. Suitable features of synthetic and semi-synthetic lipids include, for example, myristoyl, palmitoyl, and stearoyl fatty acids. In some embodiments, wherein the lipid comprises one or more ester-linked fatty acids, the fatty acid is myristoyl fatty acid. In certain embodiments, the lipid is 1,2-dimyristoyl-glycerol (DMG) or a salt thereof. In other embodiments, wherein the lipid comprises one or more ester-linked fatty acids, the fatty acid is stearoyl fatty acid. In certain embodiments, the lipid is 1,2-diastearoyl glycerol (DSG) or a salt thereof. In some embodiments, liposomes of the present disclosure may contain a mixture of two or more types of lipids. Such mixture may be present at any ratio that is suitable for encapsulating a carbohydrate of the present disclosure and delivering such carbohydrate to a cell interior. In some embodiments, liposomes of the present disclosure may contain a lipid selected from phospholipid, a glycerolipid, a sphingolipid, and any combination thereof. As disclosed herein, such a lipid has a polar head group and a fatty acid tail that may be linked by, for example, an ester linkage or an ether linkage.

In some embodiments, liposomes of the present disclosure may contain one or more lipids having polar head groups. The lipids may contain any suitable polar head group known in the art. Suitable polar head groups include, for example, choline, ethanolamine, serine, glycerol, inositol, and any combination thereof.

In some embodiments, liposomes of the present disclosure may contain one or more phospholipids. Liposomes of the present disclosure may contain any suitable phospholipid known in the art. Suitable phospholipids include, for example, phosphatidylcholine (PC), phosphatidylethanolamine (PE), phosphatidylserine (PS), phosphatidylglycerol (PG), phosphatidylinositol (PI), and any combination thereof. In some embodiments, liposomes of the present disclosure may contain phosphatidylcholine (PC). In some embodiments, liposomes of the present disclosure may contain phosphatidylethanolamine (PE). In certain embodiments, liposomes of the present disclosure may contain phosphatidylcholine (PC) and phosphatidylethanolamine (PE).

In some embodiments, the phospholipid comprises two hydrophobic fatty acid tails. In some embodiments, each of the fatty acid tails comprises an aliphatic chain. In some embodiments, the two fatty acid tails are the same. In some embodiments, the two fatty acid tails are different. In some embodiments, the aliphatic chain is unsaturated. In some embodiments, the aliphatic chain is saturated. In some embodiments, the aliphatic chain is selected from the group consisting of an optionally substituted alkyl, an optionally substituted alkenyl, and an optionally substituted alkynyl. In some embodiments, the alkyl is linear. In some embodiments, each of the fatty acid chains is an unsubstituted $C_{4-28}$ alkyl. In some embodiments, each of the fatty acid chains is a $C_{4-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In some embodiments, each of the fatty acid chains is an unsubstituted $C_{4-28}$ alkenyl. In some embodiments, the alkenyl is linear or branched. In some embodiments, each of the fatty acid chains has one or more double bonds. In some embodiments, the double bond has cis configuration. In some embodiments, the double bond has trans configuration. In some embodiments, each of the fatty acid chains is a $C_{4-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In some embodiments, each of the fatty acid chains is selected from the group consisting of an optionally substituted $C_{10-28}$ alkyl, an optionally substituted $C_{10-28}$ alkenyl and an optionally substituted $C_{10-28}$ alkynyl. Suitable phospholipids include, for example, 1,2-dioleoyl-sn-glycero-3-phosphoethanolamine (DOPE), 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS), 1,2-distearoyl-sn-glycero-3-phosphoethanolamine (DSPE), N-dodecanoyl-1,2-di-(9Z-octadecenoyl)-sn-glycero-3-phosphoethanolamine (N-C12-DOPE), or a salt thereof, or a combination of any of the foregoing.

It should generally be understood that DPPG is also generally referred to in the art as 1,2-dipalmitoyl-sn-glycero-3-phospho-(1'-rac-glycerol); DOPG is also generally referred to in the art as 1,2-dioleoyl-sn-glycero-3-phospho-(1'-rac-glycerol); and N-C12-DOPE is also generally referred to in the art as (2R)-5-hydroxy-2-{[(9Z)-octadec-9-enoyl]oxy}-5,10-dioxo-4,6-dioxa-9-aza-5λ(5)-phosphahenicosan-1-yl (9Z)-octadec-9-enoate.

In one variation, the phospholipid is:

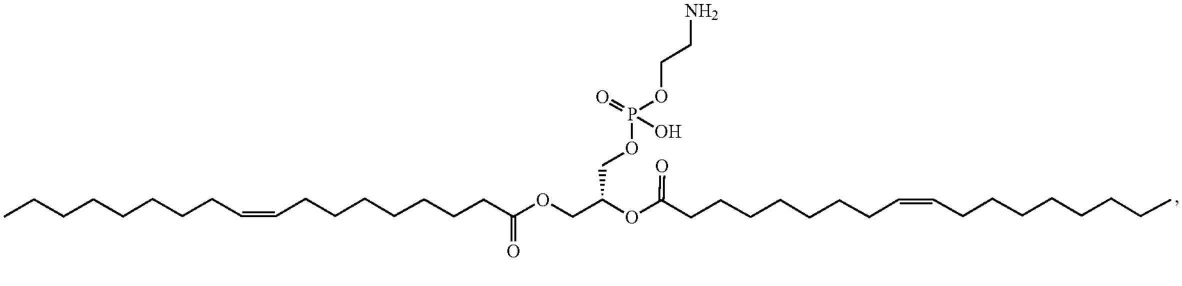,

-continued

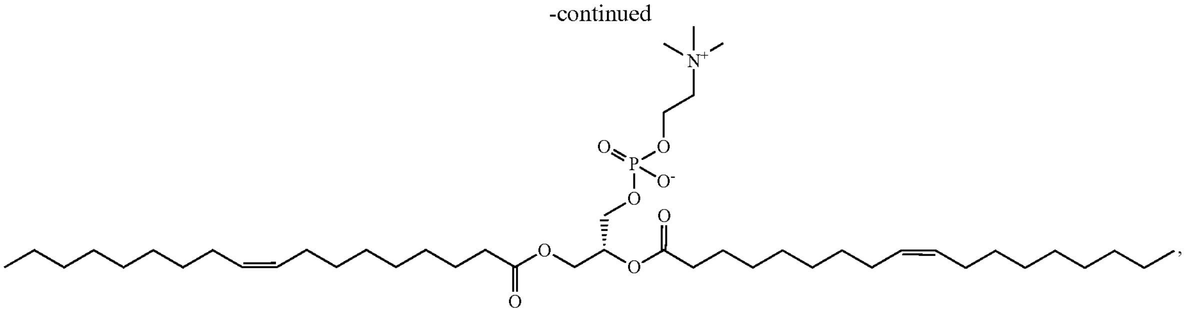

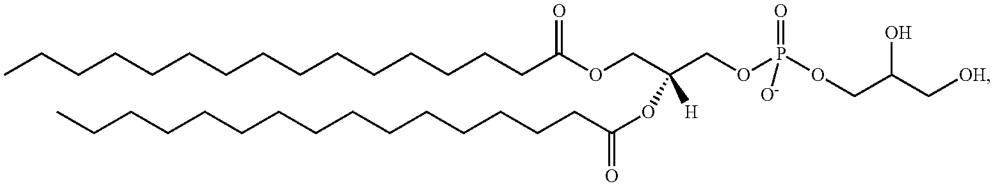

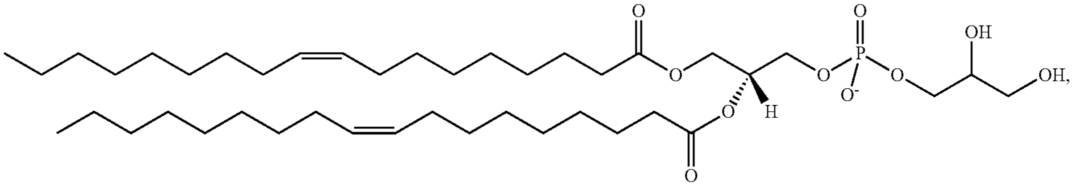

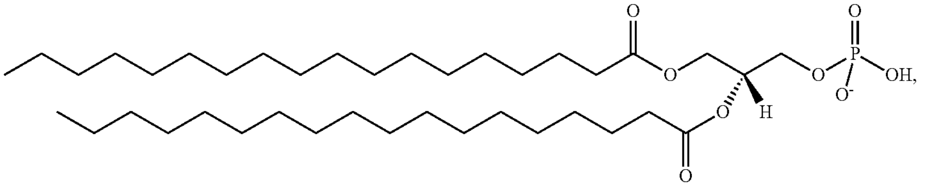

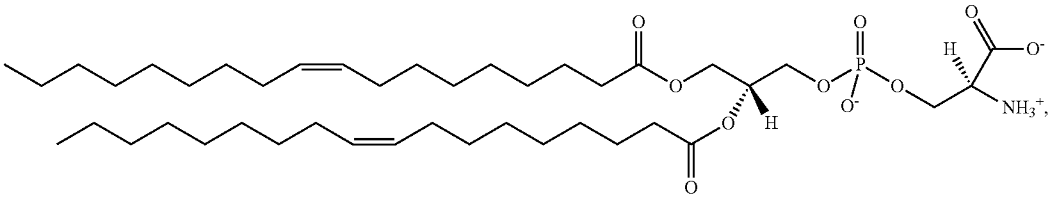

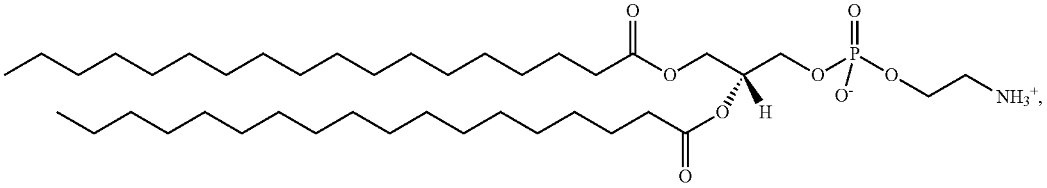

or

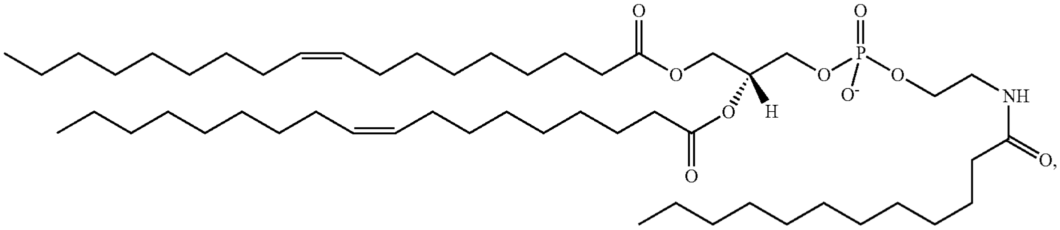 [SMILES: CCCCCCCC/C=C\CCCCCCCC(=O)OC[C@H](COP(=O)([O-])OCCNC(=O)CCCCCCCCCCC)OC(=O)CCCCCCC/C=C\CCCCCCCC]

or a salt thereof, or any combination of the foregoing.

In some embodiments, the one or more phospholipids are present at a concentration of up to about 10 molar percent, about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent, about 70 molar percent, about 75 molar percent, about 80 molar percent, about 85 molar percent, or about 90 molar percent. In some embodiments, the one or more phospholipids are present at a concentration of at least 5 molar percent, at least 10 molar percent, at least 15 molar percent, at least 20 molar percent, at least 25 molar percent, at least 30 molar percent, at least 35 molar percent, at least 40 molar percent, at least 45 molar percent, at least 50 molar percent, at least 55 molar percent, at least 60 molar percent, at least 65 molar percent, at least 70 molar percent, or at least 75 molar percent.

In some embodiments, the liposome further comprises a molecule that is capable of minimizing degradation of the lipid particle and/or enhancing retention of the lipid particle when administered to a subject, and/or makes the lipid particle immunotolerant when administered to a subject. In some embodiments the molecule is a stealth molecule, such as ethylene oxide, an ethylene oxide oligomer, an ethylene oxide polymer, polyethylene glycol (PEG), or any combination thereof; and/or a PEGylated neutral lipid. It should be understood that, in some variations, the PEGylated neutral lipids may be charged in physiological conditions.

In some embodiments, the PEGylated lipid is a lipid with ester-linked fatty acids. In certain embodiments, the PEGylated lipid is a lipid of formula (X):

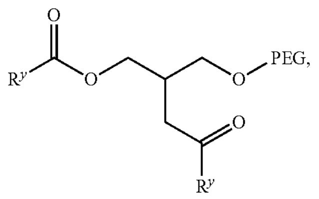

or a salt thereof, wherein each $R^y$ is independently a carbon chain. In some embodiments, each $R^y$ is independently an unsaturated carbon chain. In other embodiments, each $R^y$ is independently a saturated carbon chain. In certain embodiments, each $R^y$ is independently a $C_{10-28}$ alkyl. In one embodiment, the lipid of the PEGylated lipid is 1,2-dimyristoyl-glycerol (DMG). In one embodiment, the PEGylated lipid is PEG(2k)-DMG, which is also known as DMG-$PEG_{2000}$. In one embodiment, the PEGylated lipid is:

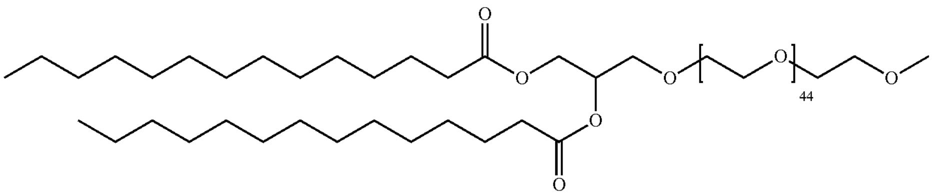

or a salt thereof. In another embodiment, the lipid of the PEGylated lipid is 1,2-diastearoyl glycerol (DSG). In one embodiment, the PEGylated lipid is PEG(2k)-DSG, which is also known as DSG-$PEG_{2000}$. In one embodiment, the PEGylated lipid is

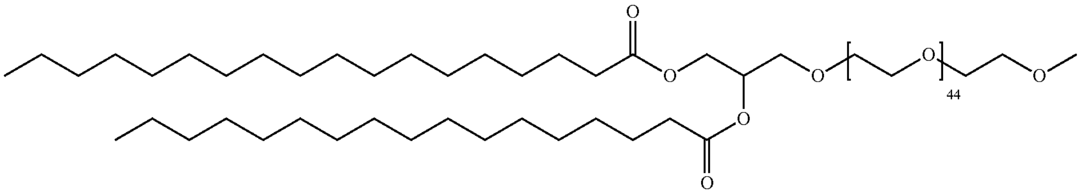

or a salt thereof.

In other embodiments, at least one phospholipid is conjugated to polyethylene glycol (PEG). In some embodiments, one phospholipid is conjugated to PEG. The PEG may be conjugated to one or more of phosphatidylcholine (PC), phosphatidylethanolamine (PE), phosphatidylserine (PS), phosphatidylglycerol (PG), phosphatidylinositol (PI), and any combination thereof. In certain embodiments, lipid particles of the present disclosure may contain PEG conjugated to phosphatidylcholine (PC). In some embodiments, the phospholipid conjugated to PEG is 1,2-dioleoyl-sn-glycero-3-phosphoethanolamine (DOPE), 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS), or 1,2-distearoyl-sn-glycero-3-phosphoethanolamine (DSPE), or a salt thereof. In some embodiments, the phospholipid conjugated to PEG is 1,2-distearoyl-sn-glycero-3-phosphoethanolamine (DSPE) or a salt thereof. In some embodiments, PEGylated phospholipid is DSPE-PEG. In some embodiments, PEGylated phospholipid is DSPE-$PEG_{2000}$. In some embodiments, the DSPE-PEG is further conjugated to a carbohydrate. In certain embodiments, the DSPE-PEG is further conjugated to a monosaccharide. In some embodiments, the DSPE-PEG is further conjugated to a galactose moiety. In certain embodiments, the DSPE-PEG-galactose has the following structure:

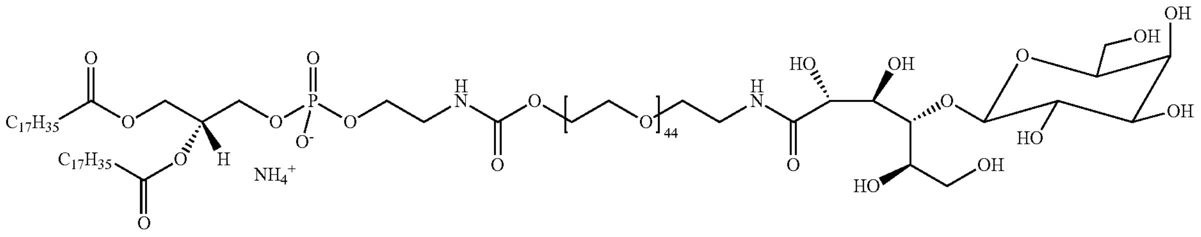

or a salt thereof.

In some embodiments, polyethylene glycol (PEG) may be present in the liposome of the present disclosure at a concentration that ranges from about 0.5 molar percent to about 20 molar percent. In some embodiments, PEG may be present in the liposome of the present disclosure at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent. In some embodiments, PEG may be present in the liposome of the present disclosure at a concentration of at least about 0.5 molar percent, at least about 1 molar percent, at least about 2 molar percent, at least about 3 molar percent, at least about 4 molar percent, at least about 5 molar percent, at least about 6 molar percent, at least about 7 molar percent, at least about 8 molar percent, at least about 9 molar percent, at least about 10 molar percent, at least about 11 molar percent, at least about 12 molar percent, at least about 13 molar percent, at least about 14 molar percent, at least about 15 molar percent, at least about 16 molar percent, at least about 17 molar percent, at least about 18 molar percent, at least about 19 molar percent, or at least about 20 molar percent; or between 0.5 molar percent and 50 molar percent, between 0.5 molar percent and 40 molar percent, between 0.5 molar percent and 30 molar percent, or between 0.5 molar percent and 20 molar percent. In certain embodiments, a phospholipid conjugated to polyethylene glycol (PEG) may be present in the liposome of the present disclosure at a concentration of about 3 molar percent. In certain embodiments, a phospholipid conjugated to polyethylene glycol (PEG) may be present in the liposome of the present disclosure at a concentration of about 5 molar percent.

In some embodiments, polyethylene glycol (PEG) may be present in the liposome of the present disclosure at a molecular weight that ranges from about 200 Da to about 40,000 Da. In some embodiments, polyethylene glycol (PEG) may be present in the liposome of the present disclosure at a molecular weight that ranges from about 200 Da to about 10,000 Da. In some embodiments, polyethylene glycol (PEG) may be present in the liposome of the present disclosure at a molecular weight of about 200 Da, about 300 Da, about 400 Da, about 500 Da, about 600 Da, about 700 Da, about 800 Da, about 900 Da, about 1,000 Da, about 1,500 Da, about 2,000 Da, about 2,500 Da, about 3,000 Da, about 3,500 Da, about 4,000 Da, about 4,500 Da, about 5,000 Da, about 5,500 Da, about 6,000 Da, about 6,500 Da, about 7,000 Da, about 7,500 Da, about 8,000 Da, about 8,500 Da, about 9,000 Da, about 9,500 Da, or about 10,000 Da; or between about 200 Da and about 10,000 Da.

In some embodiments, the liposome further comprises contain one or more sterols. In some embodiments, the one or more sterols comprise one or more neutral sterols. In other embodiments, the one or more sterols comprise one or more charged sterols. In still other embodiments, the one or more sterols comprise a combination of neutral sterols and charged sterols. Suitable phospholipids include, for example, cholesterol and cholesteryl hemisuccinate (CHEMS), dicetyl phosphate, and Solulan C24. In some embodiments, the one or more charged sterols comprise CHEMS. In other embodiments, the liposome further comprises cholesterol, also referred to herein as "Chol". In one variation, the liposome further comprises:

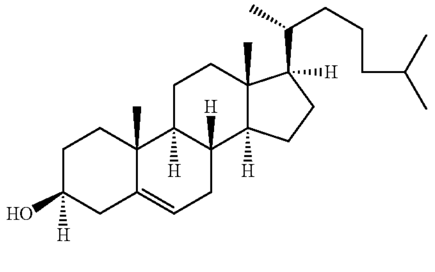

or a salt thereof.

In some embodiments, a sterol of the present disclosure, such as cholesterol or CHEMS, may be present in the liposome of the present disclosure at a concentration of up to about 5 molar percent, about 10 molar percent, about 15 molar percent, about 20 molar percent, about 30 molar percent, about 40 molar percent, or about 50 molar percent; or at least 5 molar percent, at least 10 molar percent, at least 15 molar percent, at least 20 molar percent, at least 25 molar percent, at least 30 molar percent, at least 35 molar percent, or at least 40 molar percent; or between 5 molar percent and 50 molar percent. In certain embodiments, a sterol of the present disclosure, such as cholesterol or CHEMS, may be present in the liposome of the present disclosure at a concentration of at most 15 molar percent. In certain embodiments, a sterol of the present disclosure, such as cholesterol or CHEMS, may be present in the liposome of the present disclosure at a concentration of about 3 molar percent, about 5 molar percent, about 20 molar percent or about 30 molar percent. In some embodiments, a sterol of the present disclosure, such as cholesterol or CHEMS, may be present in the liposome of the present disclosure at a molar ratio of 1:1 or 2:1.

In some embodiments, the liposomes of the present disclosure have an average particle size that ranges from about 0.02 microns in diameter to about 0.5 microns in diameter. In certain embodiments, the liposomes of the present disclosure have an average particle size of about 0.02 microns in diameter, about 0.03 microns in diameter, about 0.04 microns in diameter, about 0.05 microns in diameter, about 0.06 microns in diameter, about 0.07 microns in diameter, about 0.08 microns in diameter, about 0.09 microns in diameter, about 0.1 microns in diameter, about 0.15 microns in diameter, about 0.2 microns in diameter, about 0.25 microns in diameter, about 0.3 microns in diameter, about 0.35 microns in diameter, about 0.4 microns in diameter, about 0.45 microns in diameter, or about 0.5 microns in diameter. In some embodiments, the liposomes of the present disclosure have an average particle size of about 0.025 microns to about 0.25 microns. In some embodiments, the liposomes of the present disclosure have an average particle size of about 0.025 microns to about 0.05 microns, about 0.05 microns to about 0.1 microns, about 0.1 microns to about 0.2 microns, about 0.2 microns to about 0.3 microns, about 0.3 microns to about 0.4 microns, about 0.4 microns to about 0.5 microns, or about 0.04 microns to about 0.22 microns.

In one aspect, the liposome comprises:

i) at least one phospholipid having an ethanolamine head group and an unsaturated fatty acid tail, wherein the unsaturated fatty acid tail comprises at least one $C_{10-28}$ carbon chain;

ii) one or more of (a) to (c):
   a) at least one phospholipid having a polar head group and a saturated fatty acid tail,
   b) at least one phospholipid having a polar head group and an unsaturated fatty acid tail, wherein the polar head group comprises a quaternary ammonium cation, a glycerol group, or a serine group, and
   c) at least one acidic cholesterol ester or cholesterol; and iii) polyethylene glycol (PEG), wherein the PEG is conjugated to at least one phospholipid.

In some embodiments, the unsaturated fatty acid tail in i) of the liposome is selected from the group consisting of an optionally substituted $C_{10-28}$ alkenyl and an optionally substituted $C_{10-28}$ alkynyl. In some embodiments, each of the fatty acid chains is an unsubstituted $C_{10-28}$ alkenyl. In some embodiments, the alkenyl is linear or branched. In some embodiments, each of the fatty acid chains has one or more double bonds. In some embodiments, each double bond has cis configuration. In some embodiments, each double bond has trans configuration. In some embodiments, each of the fatty acid chains is a $C_{10-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. In some embodiments, the at least one phospholipid having an ethanolamine head group and an unsaturated fatty acid tail in i) of the liposome is 1,2-dioleoyl-sn-glycero-3-phosphoethanolamine (DOPE) or a salt thereof. In one variation, the at least one phospholipid having an ethanolamine head group and an unsaturated fatty acid tail in i) of the liposome is:

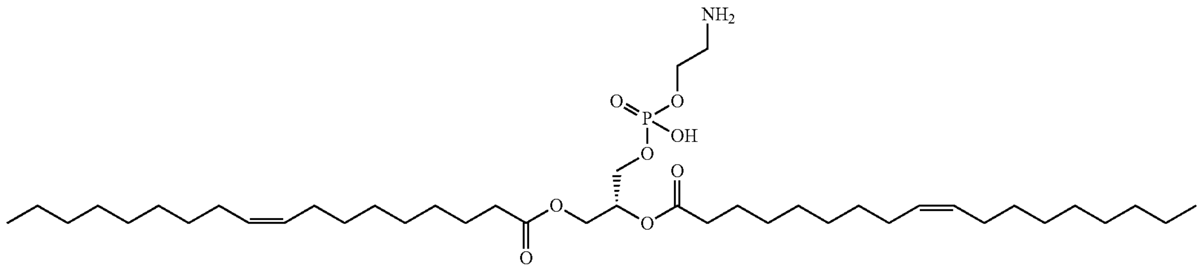 [SMILES: CCCCCCCC/C=C\CCCCCCCC(=O)OC[C@H](COP(=O)(O)OCCN)OC(=O)CCCCCCC/C=C\CCCCCCCC]

or a salt thereof.

In some embodiments, the at least one phospholipid having an ethanolamine head group and an unsaturated fatty acid tail in i) is present in the amount of up to about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent, about 70 molar percent, about 75 molar percent, about 80 molar percent, about 85 molar percent, or about 90 molar percent. In some embodiments, the at least one phospholipid having an ethanolamine head group and an unsaturated fatty acid tail in i) is present in the amount of at least about 10 molar percent, at least about 20 molar percent, at least about 30 molar percent, at least about 40 molar percent, at least about 50 molar percent, at least about 60 molar percent, at least about 70 molar percent or at least about 80 molar percent; or between about 10 molar percent and 80 molar percent. In some embodiments, the at least one phospholipid having an ethanolamine head group and an unsaturated fatty acid tail in i) is present in the amount of about 10-20 molar percent, about 20-30 molar percent, about 30-40 molar percent, about 40-50 molar percent, about 50-60 molar percent, about 60-70 molar percent, about 70-80 molar percent, about 10-30 molar percent, about 30-50 molar percent, about 50-80 molar percent, about 10-50 molar percent or about 40-80 molar percent.

In some embodiments, the polar head group in ii)a) of the liposome is selected from the group consisting of glycerol, choline, phosphate and serine. In some embodiments, the polar head group in ii)a) of the liposome is choline. In some embodiments, the saturated fatty acid tail is an optionally substituted alkyl. In some embodiments, the saturated fatty acid tail is an unsubstituted $C_{4-28}$ alkyl. In some embodiments, the saturated fatty acid tail is a $C_{4-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. In some embodiments, the at least one phospholipid having a polar head group and a saturated fatty acid tail in ii)a) of the liposome is 1,2-dipalmitoyl-phosphatidylglycerole (DPPG), 1,2-distearoyl-sn-glycero-3-phosphate (DSPA), 1,2-distearoyl-sn-glycero-3-phosphoethanolamine (DSPE), or 1,2-distearoyl-sn-glycero-3-phosphocholine (DSPC), or a salt thereof. In one variation, the at least one phospholipid having a polar head group and a saturated fatty acid tail in ii)a) of the liposome is:

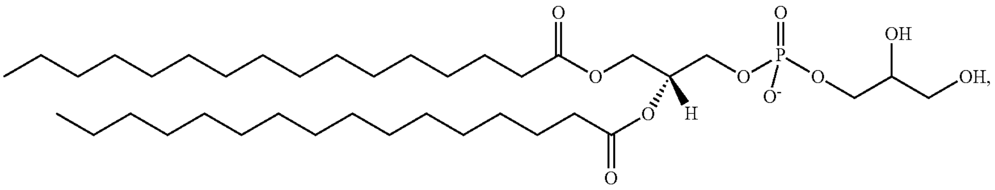

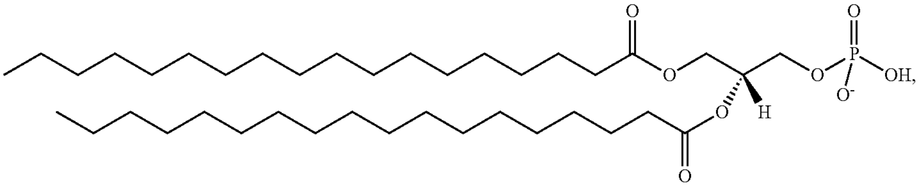

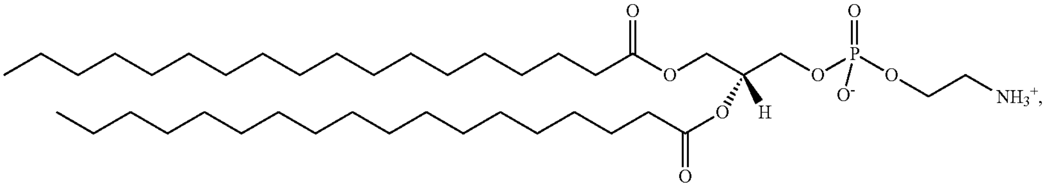

or

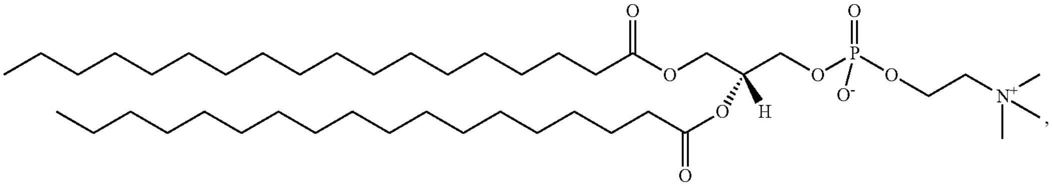

or a salt thereof.

In some embodiments, the unsaturated fatty acid tail in ii)b) of the liposome is selected from the group consisting of an optionally substituted alkenyl, and an optionally substituted alkynyl. In some embodiments, the unsaturated fatty acid tail in ii)b) of the liposome is an unsubstituted $C_{10-28}$ alkenyl. In some embodiments, the alkenyl is linear or branched. In some embodiments, the unsaturated fatty acid tail in ii)b) of the liposome has one or more double bonds. In some embodiments, each double bond has cis configuration. In some embodiments, each double bond has trans configuration. In some embodiments, the unsaturated fatty acid tail in ii)b) of the liposome is a unsubstituted $C_{10-28}$ alkenyl. In some embodiments, the unsaturated fatty acid tail in ii)b) of the liposome is a $C_{10-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. Suitable phospholipids include, for example, 1,2-dioleoyl-sn-glycero-3-phosphocholine (DOPC), 1,2-dioleoyl-sn-glycero-3-phosphoglycerol (DOPG), and 1,2- dioleoyl-sn-glycero-3-phospho-L-serine (DOPS), or a salt thereof. In one variation, the phospholipid is:

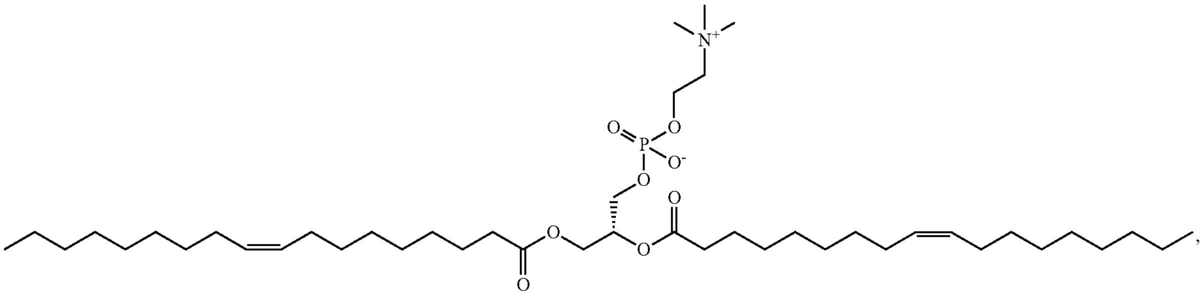

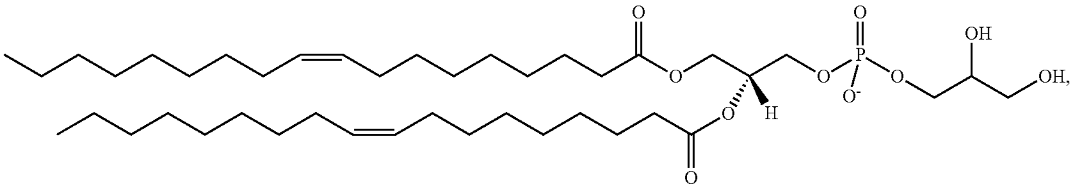

or

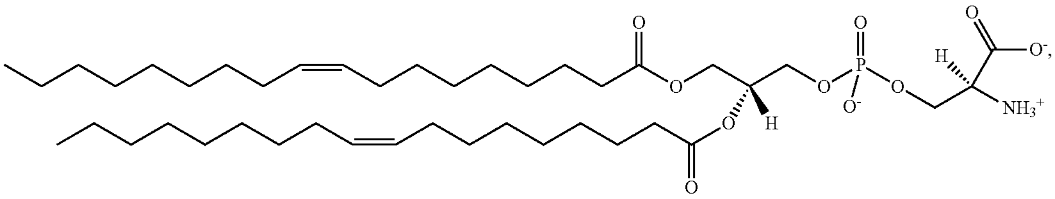

or a salt thereof.

In some embodiments, the at least one acidic cholesterol ester in ii)c) of the liposome is cholesteryl hemisuccinate (CHEMS). In one variation, the at least one acidic cholesterol ester in ii)c) of the liposome is:

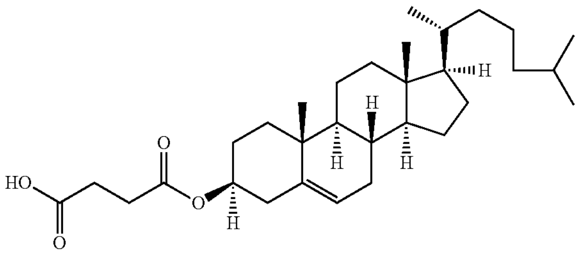

or a salt thereof.

In some embodiments, the one or more of a)-c) in ii) of the liposome is present in the amount of up to about 5 molar percent, about 10 molar percent, about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent or about 70 molar percent. In some embodiments, the one or more of a)-c) in ii) of the liposome is present in the amount of at least about 5 molar percent, at least about 10 molar percent, at least about 15 molar percent, at least about 20 molar percent, at least about 25 molar percent, at least about 30 molar percent, at least about 35 molar percent, at least about 40 molar percent, at least about 45 molar percent, at least about 50 molar percent, at least about 55 molar percent or at least about 60 molar percent. In some embodiments, the one or more of a)-c) in ii) of the liposome is present in the amount of about 5-10 molar percent, about 10-15 molar percent, about 15-20 molar percent, about 20-25 molar percent, about 25-30 molar percent, about 30-35 molar percent, about 35-40 molar percent, about 40-45 molar percent, about 45-50 molar percent, about 50-55 molar percent, about 55-60 molar percent, about 60-65 molar percent, about 65-70 molar percent, about 5-25 molar percent, about 25-50 molar percent or about 50-70 molar percent.

In some embodiments, the at least one phospholipid that is conjugated to PEG is phosphatidylcholine (PC), phosphatidylethanolamine (PE), phosphatidylserine (PS), phosphatidylglycerol (PG) or phosphatidylinositol (PI). In some embodiments, such phospholipid is 1,2-dioleoyl-sn-glycero-3-phosphoethanolamine (DOPE), 1,2-dioleoyl-sn-glycero-3-phosphocholine (DOPC), 1,2-dipalmitoyl-phosphatidylglycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS) or 1,2-distearoyl-sn-glycero-3-phosphoethanolamine (DSPE), or a salt thereof. In some embodiments, such phospholipid is 1,2-distearoyl-sn-glycero-3-phosphoethanolamine (DSPE), or a salt thereof.

In one variation, the phospholipid that is conjugated to PEG is:

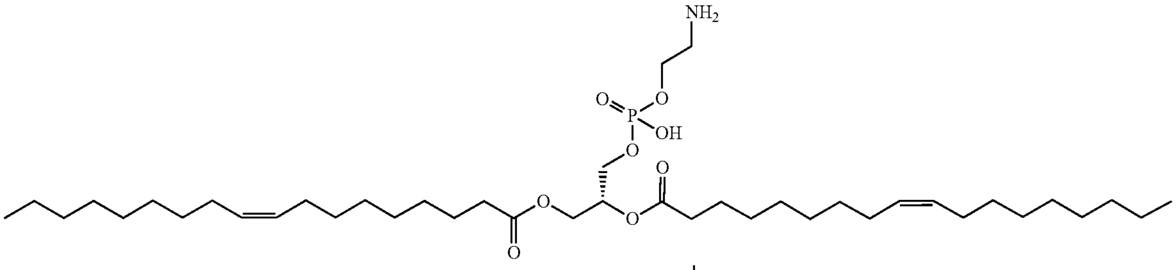

,

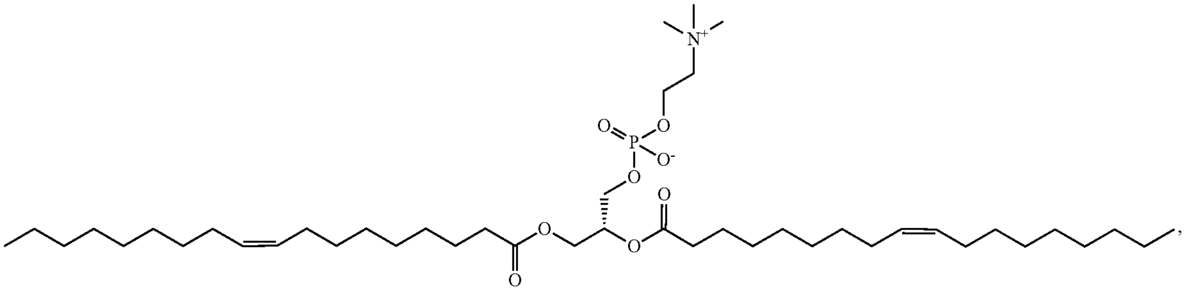

,

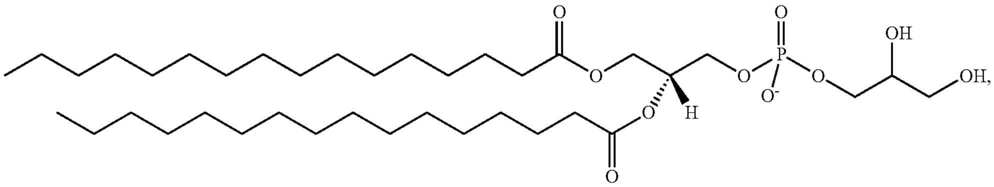

,

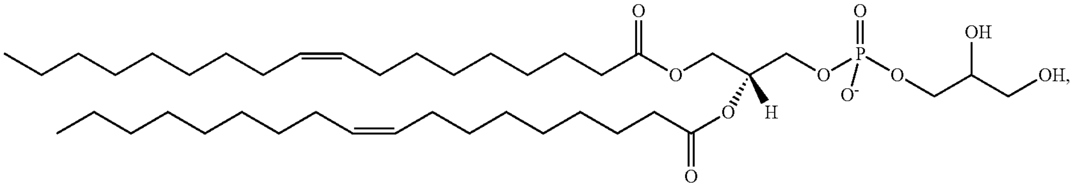

,

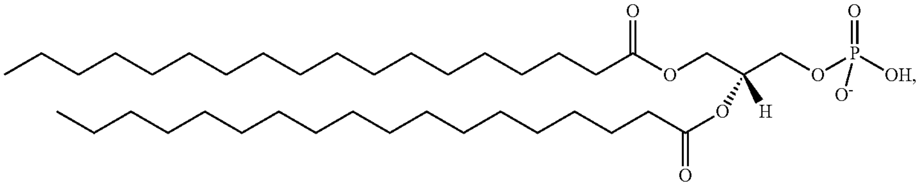

,

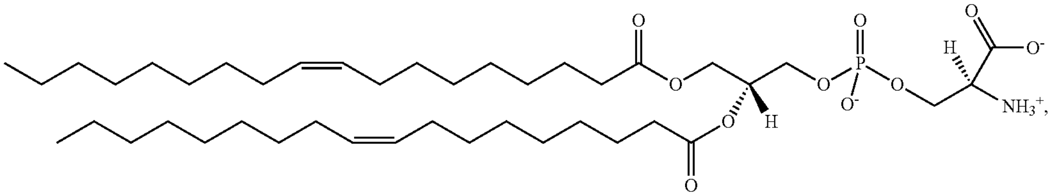

, or

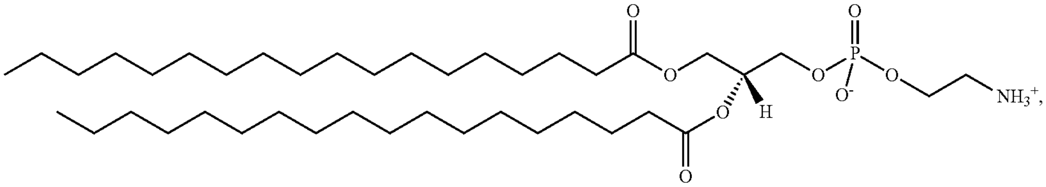

, or a salt thereof.

In some embodiments, the conjugated PEG is present in the liposome at a concentration that ranges from about 0.5 molar percent to about 20 molar percent. In some embodiments, the conjugated PEG is present in the liposome at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent; or between about 0.5 molar percent and 20 molar percent. In certain embodiments, the conjugated PEG is present in the liposome at a concentration of about 3 molar percent. In certain embodiments, the conjugated PEG is present in the liposome at a concentration of about 5 molar percent.

In some embodiments, the DOPE is present in the liposome composition in the amount of about 0-80 molar percent, about 10-80 molar percent, about 20-80 molar percent or about 30-80 molar percent, about 10-70 molar percent, about 20-70 molar percent, about 30-70 molar percent, about 30-60 molar percent, about 40-60 molar percent, about 30-35 molar percent, about 35-40 molar percent, about 40-45 molar percent, about 45-50 molar percent, about 50-55 molar percent, about 55-60 molar percent, about 60-65 molar percent, about 65-70 molar percent, or about 70-75 molar percent. In some variations, the DOPE is present in the amount of about 0-30 molar percent, about 5-30 molar percent, about 10-30 molar percent, about 15-30 molar percent, about 20-30 molar percent, or about 25-30 molar percent. In other variations, the DOPE is present in the amount of about 0-5 molar percent, about 0-10 molar percent, about 0-15 molar percent, about 0-20 molar percent, or about 0-25 molar percent.

In some embodiments, the liposome composition comprises N-C12-DOPE. In some embodiments, the N-C12-DOPE is present in the amount of about 0-80 molar percent, about 60-80 molar percent. about 65-80 molar percent, about 70-80 molar percent, or about 75-80 molar percent. In other embodiments, the N-C12-DOPE is present in the amount of about 60-65 molar percent, about 65-70 molar percent, about 70-75 molar percent, or about 75-80 molar percent.

In some embodiments, the DOPC is present in the amount of about 0-75 molar percent, about 10-75 molar percent, about 35-75 molar percent, about 35-70 molar percent, about 35-65 molar percent, about 35-60 molar percent, about 35-55 molar percent, or about 35-50 molar percent. In other embodiments, the DOPC is present in the amount of about 10-15 molar percent, about 15-20 molar percent, about 20-25 molar percent, about 25-30 molar percent, about 30-35 molar percent, about 35-40 molar percent, about 40-45 molar percent, about 45-50 molar percent, about 50-55 molar percent, about 55-60 molar percent, or about 60-65 molar percent.

In some embodiments, the DSPE-PEG is present in the amount of about 0-20 molar percent, about 0-10 molar percent, about 0-9 molar percent, about 0-8 molar percent, about 0-7 molar percent, about 0-6 molar percent, about 0-5 molar percent, or about 0-4 molar percent. In other embodiments, the DSPE-PEG is present in the amount of about 0.1-10 molar percent, about 0.1-6 molar percent, or about 0.1-4 molar percent.

In some embodiments, the liposome composition further comprises a sterol. In some embodiments, the sterol is cholesterol. In other embodiments, the sterol is CHEMS. In certain embodiments, the sterol is present in the amount of about 0-50 molar percent, about 0-45 molar percent, about 0-40 molar percent, about 30-40 molar percent, about 0-25 molar percent, about 0-20 molar percent, about 0-15 molar percent, about 0-10 molar percent, about 0-7 molar percent, about 0-6 molar percent, or about 0-5 molar percent. In other embodiments, the sterol is present in the amount of about 5-10 molar percent, about 10-15 molar percent, about 15-20 molar percent, about 20-25 molar percent, or about 25-30 molar percent. In still other embodiments, the sterol is present in the amount of about 5-20 molar percent.

In some embodiments, the liposome composition comprises DOPE, DOPC, and DSPE-PEG. In certain embodiments, the DSPE-PEG is DSPE-$PEG_{350-2000}$, DSPE-$PEG_{350-5000}$, DSPE-$PEG_{350-10000}$, or DSPE-$PEG_{350-40000}$; or DSPE-$PEG_{1000}$, DSPE-$PEG_{2000}$, DSPE-$PEG_{5000}$, or DSPE-$PEG_{10000}$. In other embodiments, the liposome composition further comprises N-C12-DOPE. In still other embodiments, the liposome composition further comprises cholesterol. In still other embodiments, the liposome composition further comprises CHEMS.

In some embodiments, the liposome composition comprises N-C12-DOPE, DOPC, and DSPE-PEG. In certain embodiments, the DSPE-PEG is DSPE-$PEG_{350-2000}$, DSPE-$PEG_{350-5000}$, DSPE-$PEG_{350-10000}$, or DSPE-$PEG_{350-40000}$; or DSPE-$PEG_{1000}$, DSPE-$PEG_{2000}$, DSPE-$PEG_{5000}$, or DSPE-$PEG_{10000}$. In other embodiments, the liposome composition further comprises DOPE. In still other embodiments, the liposome composition further comprises cholesterol.

It is to be understood that each of the components listed in any of the liposome compositions described herein may be present in any combination of the amounts described.

In one aspect, the liposome comprises:

i) 1,2-dioleoyl-sn-glycero-3-phosphoethanolamine (DOPE) or a salt thereof;

ii) one or more stabilizer selected from (a) one or more phospholipid having a polar head group selected from the group consisting of glycerol, choline, phosphate and serine and a fatty acid tail comprising a $C_{10-28}$ aliphatic chain, or (b) an acidic cholesterol ester, or a mixture of (a) and (b); and iii) PEG conjugated to at least one phospholipid.

In one variation, the liposome comprises:

i)

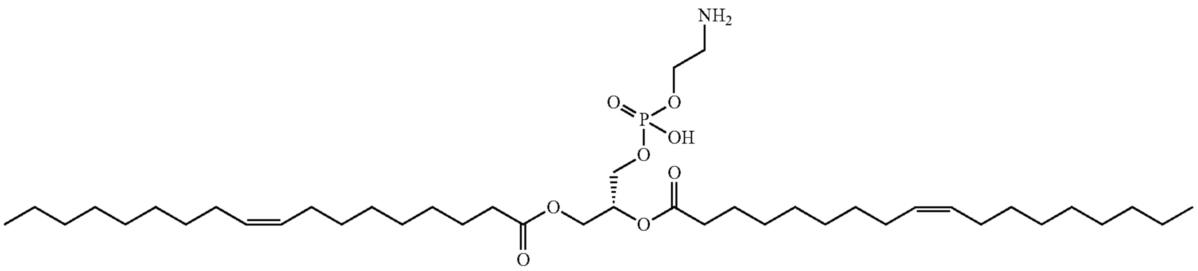 [SMILES: CCCCCCCC/C=C\CCCCCCCC(=O)OC[C@H](COP(=O)(O)OCCN)OC(=O)CCCCCCC/C=C\CCCCCCCC]

or a salt thereof;

ii) one or more stabilizer selected from (a) one or more phospholipid having a polar head group selected from the group consisting of glycerol, choline, phosphate and serine and a fatty acid tail comprising a $C_{10-28}$ aliphatic chain, or (b) an acidic cholesterol ester, or a mixture of (a) and (b); and iii) PEG conjugated to at least one phospholipid.

In some embodiments, the DOPE in i) is present in the amount of up to about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent, about 70 molar percent, about 75 molar percent, about 80 molar percent, about 85 molar percent or about 90 molar percent. In some embodiments, the DOPE in i) is present in the amount of at least about 10 molar percent, at least about 20 molar percent, at least about 30 molar percent, at least about 40 molar percent, at least about 50 molar percent, at least about 60 molar percent, at least about 70 molar percent or at least about 80 molar percent. In some embodiments, the DOPE in i) is present in the amount of about 10-20 molar percent, about 20-30 molar percent, about 30-40 molar percent, about 40-50 molar percent, about 50-60 molar percent, about 60-70 molar percent, about 70-80 molar percent, about 10-30 molar percent, about 30-50 molar percent, about 50-80 molar percent, about 10-50 molar percent or about 40-80 molar percent.

In some embodiments, the $C_{10-28}$ aliphatic chain in ii)a) of the liposome is unsaturated. In some embodiments, the $C_{10-28}$ aliphatic chain in ii)a) of the liposome is saturated. In some embodiments, the $C_{10-28}$ aliphatic chain in ii)a) of the liposome is selected from the group consisting of an optionally substituted $C_{10-28}$ alkyl, an optionally substituted $C_{10-28}$ alkenyl, and an optionally substituted $C_{10-28}$ alkynyl. In some embodiments, the $C_{10-28}$ alkyl is linear or branched. In some embodiments, the $C_{10-28}$ aliphatic chain in ii)a) of the liposome is an unsubstituted $C_{10-28}$ alkyl. In some embodiments, the $C_{10-28}$ aliphatic chain in ii)a) of the liposome is a $C_{10-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. In some embodiments, the $C_{10-28}$ aliphatic chain in ii)a) of the liposome is an unsubstituted $C_{10-28}$ alkenyl. In some embodiments, the alkenyl is linear or branched. In some embodiments, the $C_{10-28}$ aliphatic chain in ii)a) of the liposome has one or more double bonds. In some embodiments, each double bond has cis configuration. In some embodiments, each double bond has trans configuration. In some embodiments, the $C_{10-28}$ aliphatic chain in ii)a) of the liposome is a $C_{10-28}$ alkenyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. Suitable phospholipids include, for example, 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS) or a combination of forgoing.

In some embodiments, the $C_{10-28}$ aliphatic chain is a $C_{10-26}$ aliphatic chain. In other embodiments, the $C_{10-28}$ aliphatic chain is a $C_{10-24}$ aliphatic chain. In still other embodiments, the $C_{10-28}$ aliphatic chain is a $C_{10-22}$ aliphatic chain. In other embodiments, the $C_{10-28}$ aliphatic chain is a $C_{10-20}$ aliphatic chain. In still other embodiments, the $C_{10-28}$ aliphatic chain is a $C_{10-18}$ aliphatic chain. In some embodiments, the $C_{10-28}$ aliphatic chain is a $C_{10-16}$ aliphatic chain. In other embodiments, the $C_{10-28}$ aliphatic chain is a $C_{10-14}$ aliphatic chain. In still other embodiments, the $C_{10-28}$ aliphatic chain is a $C_{10-12}$ aliphatic chain. In some embodiments, the $C_{10-28}$ aliphatic chain is a $C_{14-18}$ aliphatic chain.

In some embodiments, the acidic cholesterol ester in ii)b) of the liposome is cholesteryl hemisuccinate (CHEMS). In one variation, the acidic cholesterol ester in ii)b) of the liposome is:

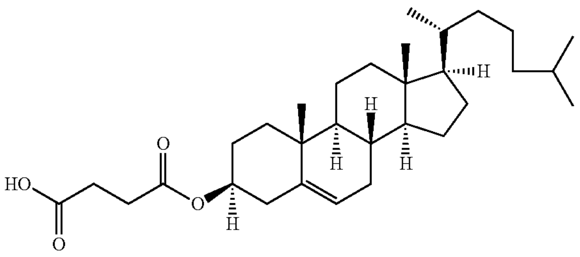

or a salt thereof.

In some embodiments, the one or more stabilizers in ii) of the liposome is present in the amount of up to about 5 molar percent, about 10 molar percent, about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent or about 70 molar percent. In some embodiments, the one or more stabilizers in ii) of the liposome is present in the amount of at least about 5 molar percent, at least about 10 molar percent, at least about 15 molar percent, at least about 20 molar percent, at least about 25 molar percent, at least about 30 molar percent, at least about 35 molar percent, at least about 40 molar percent, at least about 45 molar percent, at least about 50 molar percent, at least about 55 molar percent or at least about 60 molar percent. In some embodiments, the one or more stabilizers in ii) of the liposome is present in the amount of about 5-10 molar percent, about 10-15 molar percent, about 15-20 molar percent, about 20-25 molar percent, about 25-30 molar percent, about 30-35 molar percent, about 35-40 molar percent, about 40-45 molar percent, about 45-50 molar percent, about 50-55 molar percent, about 55-60 molar percent, about 60-65 molar percent, about 65-70 molar percent, about 5-25 molar percent, about 25-50 molar percent or about 50-70 molar percent.

In some embodiments, the at least one phospholipid that is conjugated to PEG is selected from the group consisting of phosphatidylcholine (PC), phosphatidylethanolamine (PE), phosphatidylserine (PS), phosphatidylglycerol (PG) and phosphatidylinositol (PI). In some embodiments, such phospholipid is 1,2-dioleoyl-sn-glycero-3-phosphoethanolamine (DOPE), 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS) or 1,2-distearoyl-sn-glycero-3-phosphoethanolamine (DSPE), or a salt thereof. In some embodiments, such phospholipid is 1,2-distearoyl-sn-glycero-3-phosphoethanolamine (DSPE), or a salt thereof.

In one variation, the phospholipid that is conjugated to PEG is:

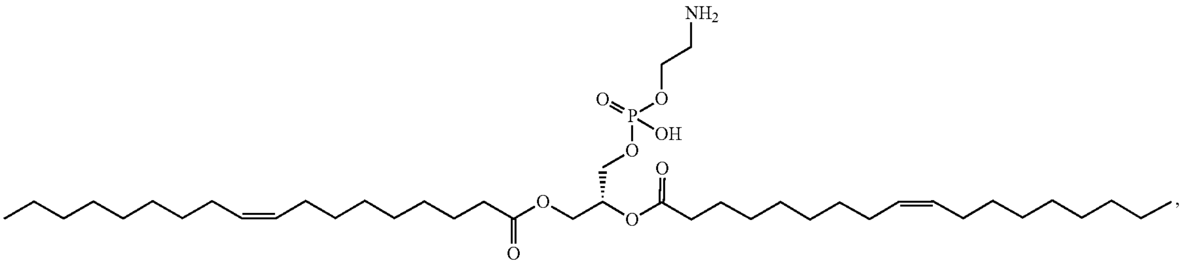

,

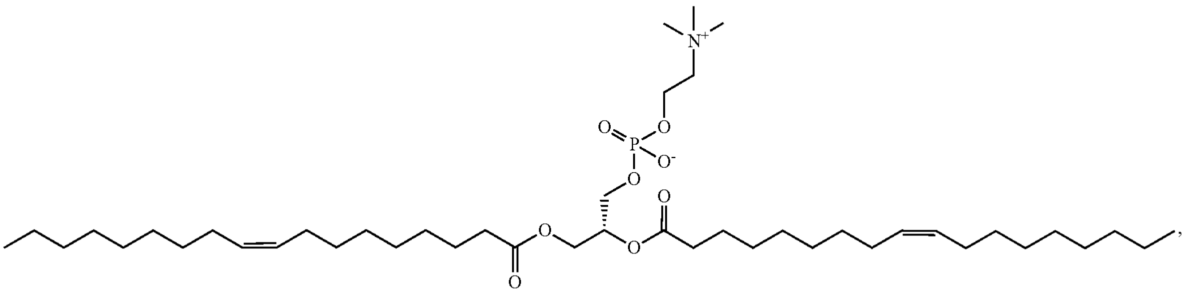

,

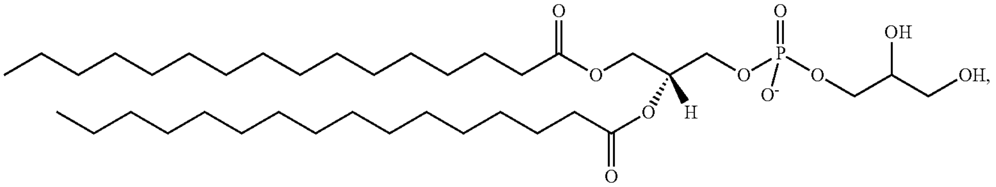

,

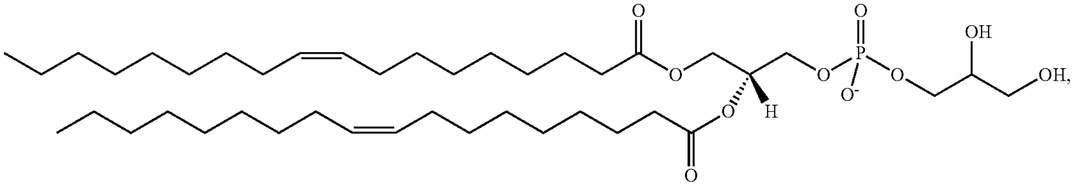

,

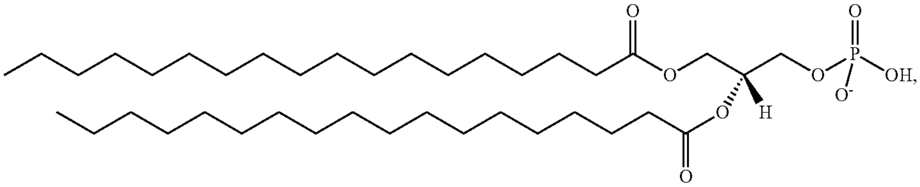

,

-continued

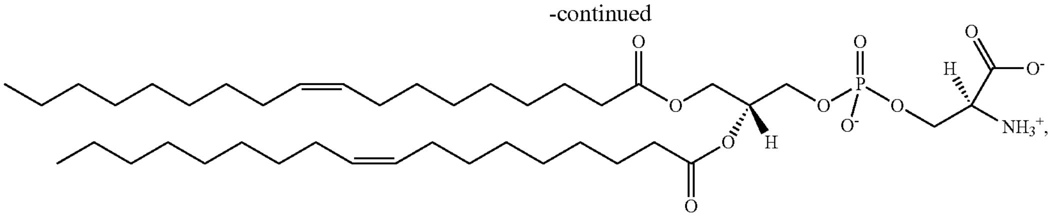

or

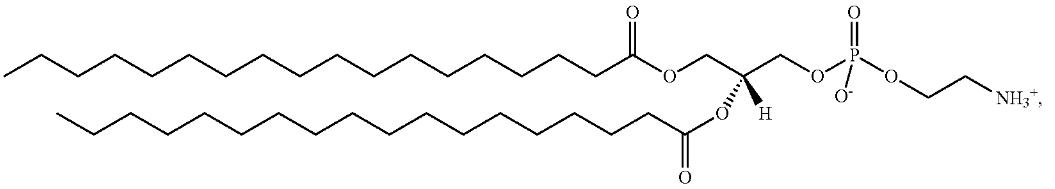

or a salt thereof.

In some embodiments, the conjugated PEG is present in the liposome at a concentration that ranges from about 0.5 molar percent to about 20 molar percent. In some embodiments, the conjugated PEG is present in the liposome at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent. In certain embodiments, the conjugated PEG is present in the liposome at a concentration of about 3 molar percent. In certain embodiments, the conjugated PEG is present in the liposome at a concentration of about 5 molar percent.

In some embodiments, the liposome further comprises cholesterol. In some embodiments, the cholesterol is present in the amount of up to about 10 molar percent, about 15 molar percent, about 20 molar percent, about 25 molar percent, about 30 molar percent, about 35 molar percent or about 40 molar percent.

In another aspect, the liposome comprises:

i) a phospholipid of formula (PL-1):

(PL-1)

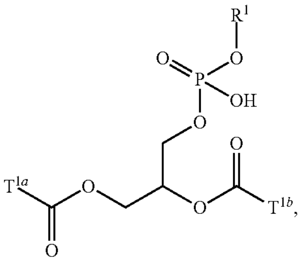

or a salt thereof, wherein:

at least one of $T^{1a}$ and $T^{1b}$ is an unsaturated carbon chain; and $R^1$ is aminoalkyl;

ii) at least one phospholipid of formula (PL-2), at least one phospholipid of formula (PL-3), or at least one cholesterol ester of formula (CE), or any combination of the foregoing:

(PL-2)

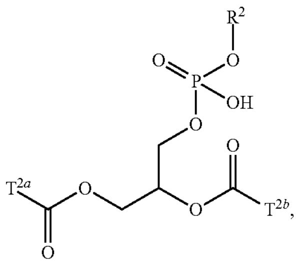

or a salt thereof, wherein:

each of $T^{2a}$ and $T^{2b}$ is an unsaturated carbon chain; and $R^2$ is alkyl substituted with a quaternary ammonium, glycerol, or alkyl substituted with —COOH and —$NH_2$;

(PL-3)

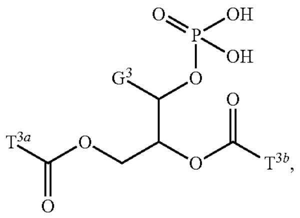

or a salt thereof, wherein:

each of $T^{3a}$ and $T^{3b}$ is a saturated carbon chain; and $G^3$ is H or alkyl substituted with at least one —OH; and (CE)

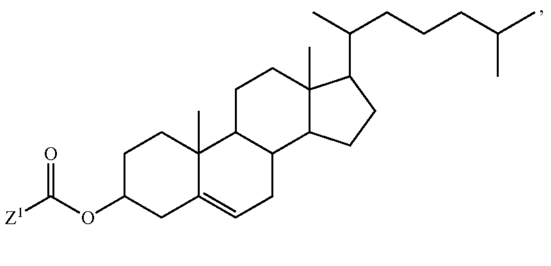

or a salt thereof, wherein:

$Z^1$ is alkyl substituted with —COOH; and iii) polyethylene glycol (PEG), wherein the PEG is conjugated to at least one phospholipid.

In yet another aspect, the liposome comprises:

i) a phospholipid of formula (PL-1):

(PL-1)

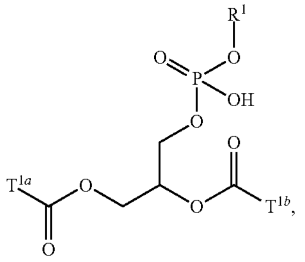

or a salt thereof, wherein:

at least one of $T^{1a}$ and $T^{1b}$ is an unsaturated carbon chain; and $R^1$ is aminoalkyl;

ii) at least one phospholipid of formula (PL-2), at least one phospholipid of formula (PL-3), or at least one cholesterol ester of formula (CE), or any combination of the foregoing:

(PL-2)

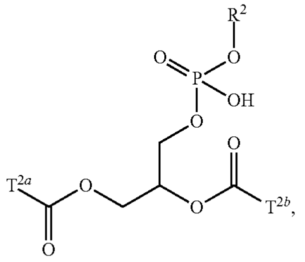

or a salt thereof, wherein:

each of $T^{2a}$ and $T^{2b}$ is an unsaturated carbon chain; and $R^2$ is alkyl substituted with a quaternary ammonium, glycerol, or alkyl substituted with —COOH and —$NH_2$;

(PL-3A)

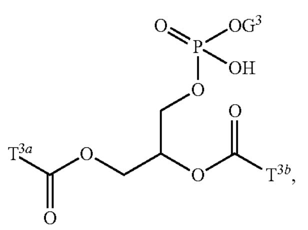

or a salt thereof, wherein:

each of $T^{3a}$ and $T^{3b}$ is a carbon chain; and $G^3$ is H or alkyl substituted with at least one —OH; and (CE)

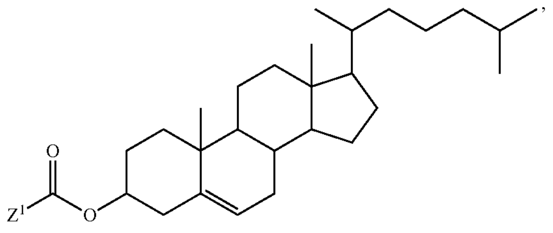

or a salt thereof, wherein:

$Z^1$ is alkyl substituted with —COOH; and iii) polyethylene glycol (PEG), wherein the PEG is conjugated to at least one phospholipid.

An "aminoalkyl" refers to an alkyl chain substituted with an amino group. Thus, in Formula (PL-1), the alkyl chain is connected to the oxygen atom of the phosphate moiety. In some embodiments, $R^1$ of Formula (PL-1) is an amino substituted $C_{1-6}$ alkyl. In some embodiments, the amino substituted $C_{1-6}$ alkyl is linear or branched. In some embodiments, $R^1$ of Formula (PL-1) is $C_{1-6}$alkyl-$NH_2$. In some embodiments, $R^1$ of Formula (PL-1) is aminoethyl, —$CH_2CH_2NH_2$. In some embodiments, each of Tia and Tib is independently $C_{10-28}$ alkenyl or $C_{10-28}$ alkynyl. In some embodiments, the $C_{10-28}$ alkenyl is linear or branched. In some embodiments, the $C_{10-28}$ alkenyl has one or more double bonds. In some embodiments, each double bond has cis configuration. In some embodiments, each double bond has trans configuration. In some embodiments, the $C_{10-28}$ alkenyl is substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl and heterocyclyl. In some embodiments, the phospholipid of Formula (PL-1) is 1,2-dioleoyl-sn-glycero-3-phosphoethanolamine (DOPE) or a salt thereof. In one variation, the phospholipid of Formula (PL-1) is

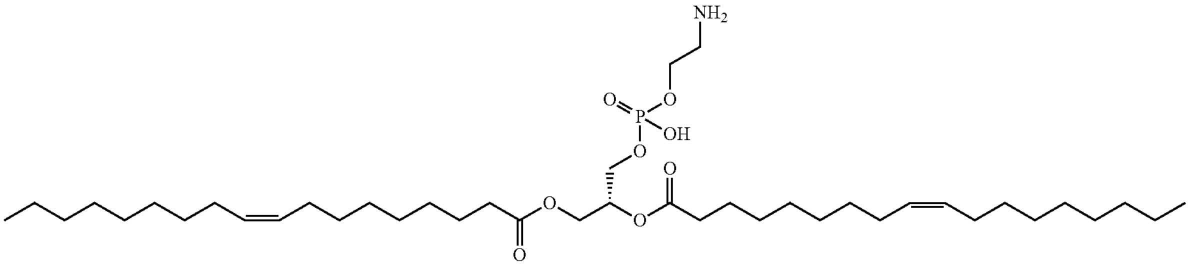 [SMILES: CCCCCCCC/C=C\CCCCCCCC(=O)OC[C@H](COP(=O)(O)OCCN)OC(=O)CCCCCCC/C=C\CCCCCCCC]

or a salt thereof.

In some embodiments, the phospholipid of Formula (PL-1) is present in the amount of up to about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent, about 70 molar percent, about 75 molar percent, about 80 molar percent, about 85 molar percent or about 90 molar percent. In some embodiments, the phospholipid of Formula (PL-1) is present in the amount of at least about 10 molar percent, at least about 20 molar percent, at least about 30 molar percent, at least about 40 molar percent, at least about 50 molar percent, at least about 60 molar percent, at least about 70 molar percent or at least about 80 molar percent. In some embodiments, the phospholipid of Formula (PL-1) is present in the amount of about 10-20 molar percent, about 20-30 molar percent, about 30-40 molar percent, about 40-50 molar percent, about 50-60 molar percent, about 60-70 molar percent, about 70-80 molar percent, about 10-30 molar percent, about 30-50 molar percent, about 50-80 molar percent, about 10-50 molar percent or about 40-80 molar percent.

In some embodiments, $R^2$ of Formula (PL-2) is an alkyl substituted with a quaternary ammonium or glycerol. In some embodiments, $R^2$ of Formula (PL-2) is a $C_{1-6}$ alkyl substituted with a quaternary ammonium or glycerol. In some embodiments, the quaternary ammonium is

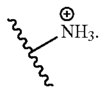

In other embodiments, the quaternary ammonium comprises one or more $C_{1-6}$ alkyl groups. In one embodiment, the quaternary ammonium is

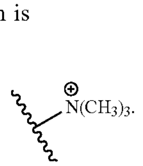

In some embodiments, $R^2$ of Formula (PL-2) is choline. In some embodiments, the $R^2$ of Formula (PL-2) is an alkyl substituted with —COOH and —$NH_2$. In some embodiments, the $R^2$ of Formula (PL-2) is a $C_{1-6}$ alkyl substituted with —COOH and —$NH_2$. In some embodiments, the $R^2$ of Formula (PL-2) is serine. In some embodiments, the $R^2$ of Formula (PL-2) is L-serine. In some embodiments, each of $T^{2a}$ and $T^{2b}$ is independently $C_{10-28}$ alkenyl or $C_{10-28}$ alkynyl. In some embodiments, the $C_{10-28}$ alkenyl is linear or branched. In some embodiments, the $C_{10-28}$ alkenyl has one or more double bonds. In some embodiments, each double bond has cis configuration. In some embodiments, each double bond has trans configuration. In some embodiments, the $C_{10-28}$ alkenyl is unsubstituted. In some embodiments, the $C_{10-28}$ alkenyl is substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In some embodiments, the phospholipid of Formula (PL-2) is 1,2-dioleoyl-sn-glycero-3-phosphocholine (DOPC) or 1,2-dioleoyl-sn-glycero-3-phospho-L-serine (DOPS), or a salt thereof.

In some embodiments, $G^3$ of Formula (PL-3) or Formula (PL-3A) is H. In some embodiments, $G^3$ of Formula (PL-3) or Formula (PL-3A) is an alkyl substituted with at least one —OH. In some embodiments, $G^3$ of Formula (PL-3) or Formula (PL-3A) is an alkyl substituted with two —OH. In some embodiments, $G^3$ of Formula (PL-3) or Formula (PL-3A) is glycerol. In some embodiments of Formula (PL-3) or Formula (PL-3A), each of Tia and Tb is independently a saturated carbon chain. In some embodiments, the saturated carbon chain is an optionally substituted $C_{10-28}$ alkyl. In some embodiments, the $C_{10-28}$ alkyl is linear or branched. In some embodiments, the $C_{10-28}$ alkyl is unsubstituted. In some embodiments, each of $T^{3a}$ and $T^{3b}$ is independently is a $C_{10-28}$ alkyl substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In some embodiments, the phospholipid of Formula (PL-3) or Formula (PL-3A) is 1,2-dipalmitoyl-phosphatidyl-glycerole (DPPG) or 1,2-distearoyl-sn-glycero-3-phosphate (DSPA). In some embodiments of Formula (PL-3A), each of $T^{1a}$ and $T^{ab}$ in Formula (PL-3A) is independently an unsaturated carbon chain. In some embodiments of Formula (PL-3A), each of $T^{1a}$ and $T^{ab}$ in Formula (PL-3A) is independently $C_{10-28}$ alkenyl or $C_{10-28}$ alkynyl. In some embodiments, the $C_{10-28}$ alkenyl is linear or branched. In some embodiments, the $C_{10-28}$ alkenyl has one or more double bonds. In some embodiments, each double bond has cis configuration. In some embodiments, each double bond has trans configuration. In some embodiments, the $C_{10-28}$ alkenyl is unsubstituted. In some embodiments, the $C_{10-28}$ alkenyl is substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In other embodiments, the phospholipid of Formula (PL-3A) is 1,2-dioleoyl-sn-glycero-3-phosphoglycerol (DOPG), or a salt thereof.

In some embodiment, $Z^1$ of Formula (CE) is a $C_{1-6}$ alkyl substituted with —COOH. In some embodiments, Formula (CE) is cholesteryl hemisuccinate, or a salt thereof.

In some embodiments, the at least one phospholipid of formula (PL-2), at least one phospholipid of formula (PL-3), at least one phospholipid of formula (PL-3A), or at least one cholesterol ester of formula (CE), or any combination of the foregoing is present in the amount of up to about 5 molar percent, about 10 molar percent, about 15 molar percent, about 20 molar percent, about 25 molar percent, about 30 molar percent, about 35 molar percent, about 40 molar percent, about 45 molar percent, about 50 molar percent, about 55 molar percent, about 60 molar percent, about 65 molar percent or about 70 molar percent. In some embodiments, the at least one phospholipid of formula (PL-2), at least one phospholipid of formula (PL-3), at least one phospholipid of formula (PL-3A), or at least one cholesterol ester of formula (CE), or any combination of the foregoing is present in the amount of at least about 5 molar percent, at least about 10 molar percent, at least about 15 molar percent, at least about 20 molar percent, at least about 25 molar percent, at least about 30 molar percent, at least about 35 molar percent, at least about 40 molar percent, at least about 45 molar percent, at least about 50 molar percent, at least about 55 molar percent or at least about 60 molar percent. In some embodiments, the at least one phospholipid of formula (PL-2), at least one phospholipid of formula (PL-3), at least one phospholipid of formula (PL-3A), or at least one cholesterol ester of formula (CE), or any combination of the foregoing is present in the amount of about 5-10 molar percent, about 10-15 molar percent, about 15-20 molar percent, about 20-25 molar percent, about 25-30 molar percent, about 30-35 molar percent, about 35-40 molar percent, about 40-45 molar percent, about 45-50 molar percent, about 50-55 molar percent, about 55-60 molar percent, about 60-65 molar percent, about 65-70 molar percent, about 5-25 molar percent, about 25-50 molar percent or about 50-70 molar percent.

In some embodiments, the at least one phospholipid that is conjugated to PEG is selected from the group consisting of phosphatidylcholine (PC), phosphatidylethanolamine (PE), phosphatidylserine (PS), phosphatidylglycerol (PG) and phosphatidylinositol (PI). In some embodiments, such phospholipid is 1,2-dioleoyl-sn-glycero-3-phosphoethanolamine (DOPE), 1,2-dioleoyl-sn-glycero-3-phosphocholine (DOPC), 1,2-dipalmitoyl-phosphatidyl-glycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS) or 1,2-distearoyl-sn-glycero-3-phosphoethanolamine (DSPE), or a salt thereof. In some embodiments, such phospholipid conjugated to PEG is 1,2-distearoyl-sn-glycero-3-phosphoethanolamine (DSPE), or a salt thereof.

In one variation, the phospholipid that is conjugated to PEG is:

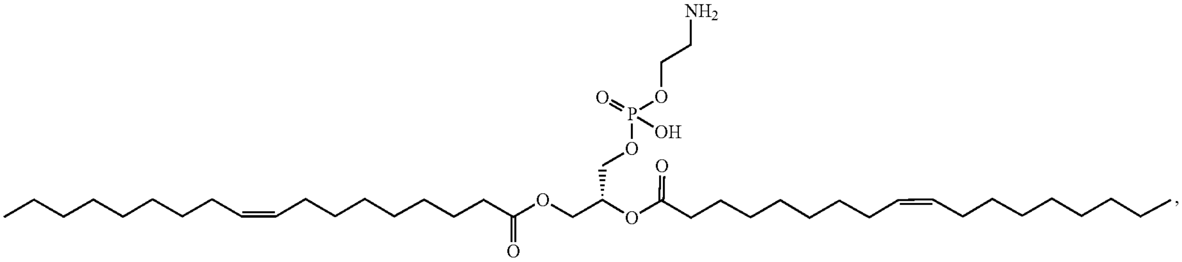
,

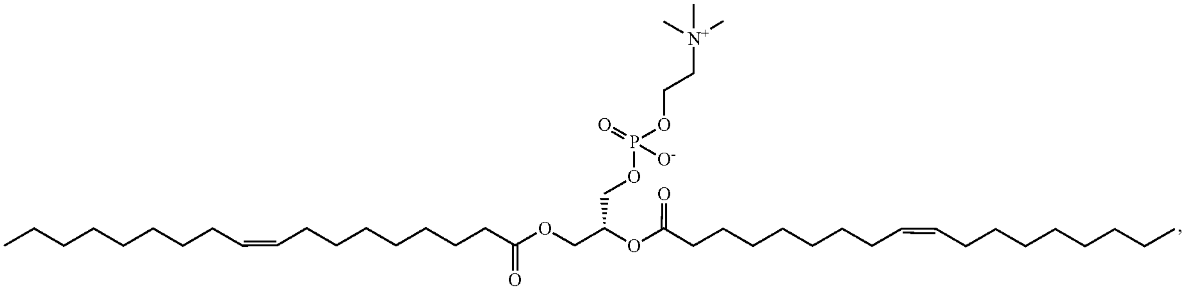
,

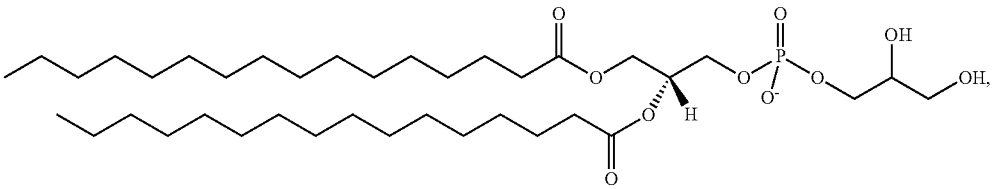
,

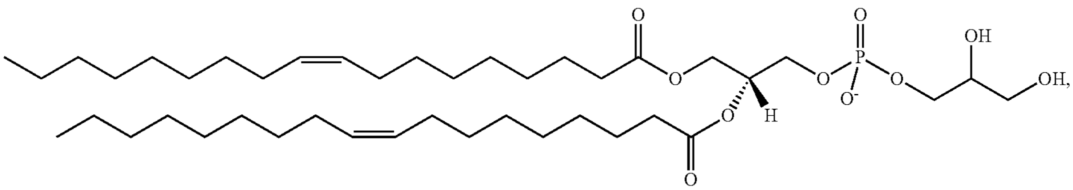
,

-continued

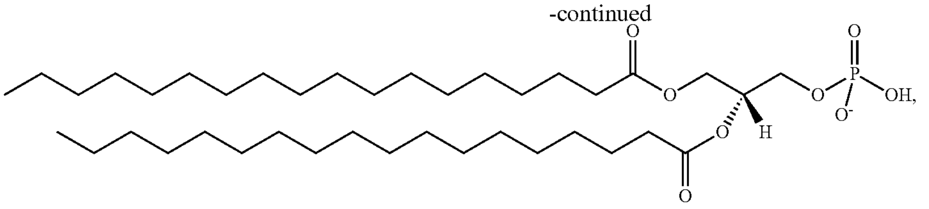

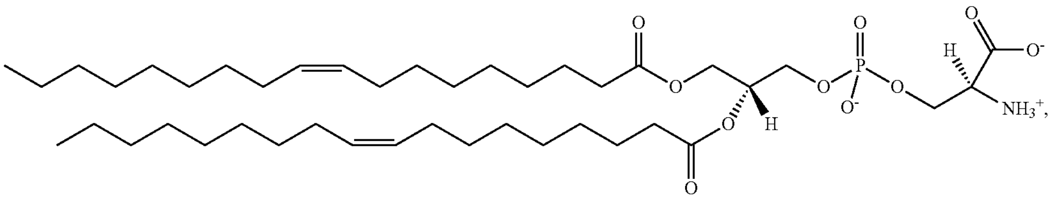

or

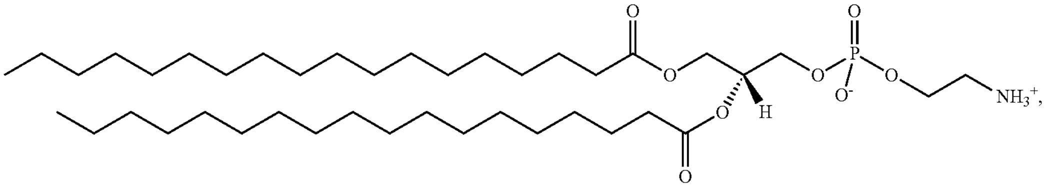

or a salt thereof.

In some embodiments, the conjugated PEG is present in the liposome at a concentration that ranges from about 0.5 molar percent to about 20 molar percent. In some embodiments, the conjugated PEG is present in the liposome at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent, or about 20 molar percent. In certain embodiments, the conjugated PEG is present in the liposome at a concentration of about 3 molar percent. In certain embodiments, the conjugated PEG is present in the liposome at a concentration of about 5 molar percent.

In some embodiments, the liposome further comprises cholesterol. In some embodiments, the cholesterol is present in the amount of up to about 10 molar percent, about 15 molar percent, about 20 molar percent, about 25 molar percent, about 30 molar percent, about 35 molar percent or about 40 molar percent.

In another aspect, the liposome comprises:

i) N-dodecanoyl-1,2-di-(9Z-octadecenoyl)-sn-glycero-3-phosphoethanolamine (N-C12-DOPE), or a salt thereof and ii) 1,2-dioleoyl-sn-glycero-3-phosphocholine (DOPC), or a salt thereof.

In another aspect, the liposome comprises:

i)

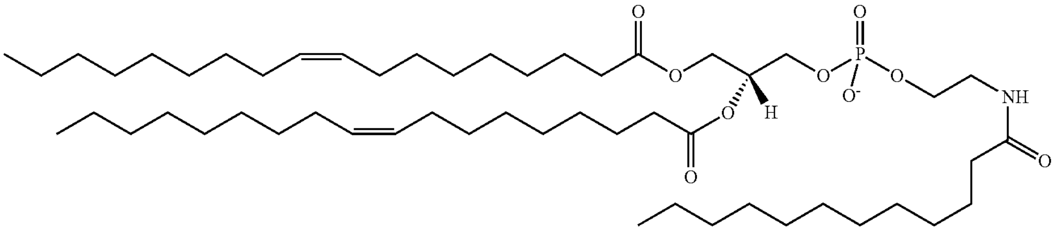 [SMILES: CCCCCCCC/C=C\CCCCCCCC(=O)OC[C@H](COP(=O)([O-])OCCNC(=O)CCCCCCCCCCC)OC(=O)CCCCCCC/C=C\CCCCCCCC]

or a salt thereof; and ii)

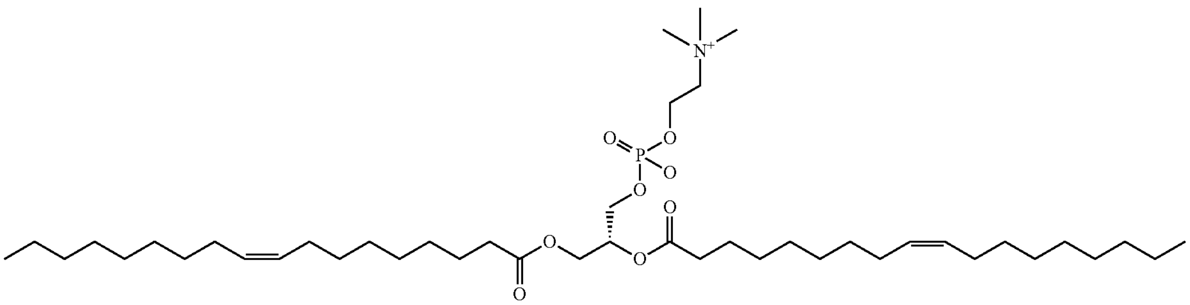 [SMILES: CCCCCCCC/C=C\CCCCCCCC(=O)OC[C@H](COP(=O)(O)OCC[N+](C)(C)C)OC(=O)CCCCCCC/C=C\CCCCCCCC]

or a salt thereof.

In some embodiments, N-C12-DOPE is present in the amount of up to about 40 molar percent, about 45 molar percent, about 50 molar percent, about 55 molar percent, about 60 molar percent, about 65 molar percent, about 70 molar percent, about 75 molar percent, about 80 molar percent, about 85 molar percent or about 90 molar percent. In some embodiments, N-C12-DOPE is present in the amount of at least about 30 molar percent, at least about 40 molar percent, at least about 50 molar percent, at least about 60 molar percent, at least about 70 molar percent or at least about 80 molar percent. In some embodiments, N-C12-DOPE is present in the amount of about 30-40 molar percent, about 40-50 molar percent, about 50-60 molar percent, about 60-70 molar percent, about 70-80 molar percent, about 30-50 molar percent or about 50-80 molar percent or about 40-80 molar percent.

In some embodiments, the DOPC is present in the amount of up to about 5 molar percent, about 10 molar percent, about 15 molar percent, about 20 molar percent, about 25 molar percent, about 30 molar percent, about 35 molar percent, about 40 molar percent, about 45 molar percent, about 50 molar percent, about 55 molar percent or about 60 molar percent. In some embodiments, the DOPC is present in the amount of at least about 5 molar percent, at least about 10 molar percent, at least about 15 molar percent, at least about 20 molar percent, at least about 25 molar percent, at least about 30 molar percent, at least about 35 molar percent, at least about 40 molar percent, at least about 45 molar percent or at least about 50 molar percent. In some embodiments, the DOPC is present in the amount of about 5-10 molar percent, about 10-15 molar percent, about 15-20 molar percent, about 20-25 molar percent, about 25-30 molar percent, about 30-35 molar percent, about 35-40 molar percent, about 40-45 molar percent, about 45-50 molar percent, about 50-55 molar percent, about 55-60 molar percent, about 5-30 molar percent or about 30-50 molar percent.

In some embodiments, the liposome further comprises PEG conjugated to at least one phospholipid, cholesterol, CHEMS or a combination of the foregoing. In some embodiments, the at least one phospholipid that is conjugated to PEG is phosphatidylcholine (PC), phosphatidylethanolamine (PE), phosphatidylserine (PS), phosphatidylglycerol (PG) or phosphatidylinositol (PI). In some embodiments, such phospholipid is 1,2-dioleoyl-sn-glycero-3-phosphoethanolamine (DOPE), 1,2-dioleoyl-sn-glycero-3-phosphocholine (DOPC), 1,2-dipalmitoyl-phosphatidylglycerole (DPPG), 1,2-dioleoyl-sn-glycero-3-phosphoglycerol (DOPG), 1,2-distearoyl-sn-glycero-3-phosphate (DSPA), 1,2-dioleoyl-sn-glycero-3-phospho-L-serine (DOPS) or 1,2-distearoyl-sn-glycero-3-phosphoethanolamine (DSPE), or a salt thereof. In some embodiments, the at least one phospholipid conjugated to PEG is 1,2-distearoyl-sn-glycero-3-phosphoethanolamine (DSPE), or a salt thereof.

In some embodiments, at least one phospholipid, cholesterol, CHEMS or a combination of the foregoing is present in the liposome at a concentration that ranges from about 0.5 molar percent to about 20 molar percent. In some embodiments, at least one phospholipid, cholesterol, CHEMS or a combination of the foregoing is present in the liposome at a concentration of about 0.5 molar percent, about 1 molar percent, about 2 molar percent, about 3 molar percent, about 4 molar percent, about 5 molar percent, about 6 molar percent, about 7 molar percent, about 8 molar percent, about 9 molar percent, about 10 molar percent, about 11 molar percent, about 12 molar percent, about 13 molar percent, about 14 molar percent, about 15 molar percent, about 16 molar percent, about 17 molar percent, about 18 molar percent, about 19 molar percent or about 20 molar percent. In certain embodiments, at least one phospholipid, cholesterol, CHEMS or a combination of the foregoing is present in the liposome at a concentration of about 3 molar percent. In certain embodiments, at least one phospholipid, cholesterol, CHEMS or a combination of the foregoing is present in the liposome at a concentration of about 5 molar percent.

In another aspect, the liposome comprises a phospholipid of formula (PL-4):

(PL-4)

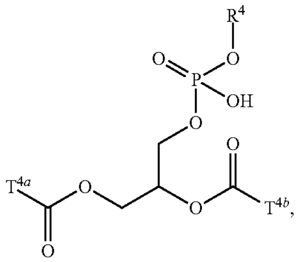

or a salt thereof, wherein:

at least one of $T^{1a}$ and $T^{1b}$ is an unsaturated carbon chain; and $R^4$ is an aliphatic chain comprising an amide moiety.

In some embodiments, $R^4$ of Formula (PL-4) is an alkyl comprising an amide moiety. In some embodiments, $R^4$ of Formula (PL-4) is a $C_{10-28}$ alkyl comprising an amide moiety. In some embodiments, $R^4$ of Formula (PL-4) is $-C_{1-12}$alkyl-NH—C(O)—$C_{1-12}$alkyl. In certain embodiments, $R^4$ of Formula (PL-4) is $-CH_2CH_2-NH-C(O)-C_{11}H_{23}$. In some embodiments, each of $T^{4a}$ and $T^{4b}$ is independently $C_{10-28}$ alkenyl or $C_{10-28}$ alkynyl. In some embodiments, the $C_{10-28}$ alkenyl is linear or branched. In some embodiments, the $C_{10-28}$ alkenyl has one or more double bonds. In some embodiments, each double bond has cis configuration. In some embodiments, each double bond has trans configuration. In some embodiments, the $C_{10-28}$ alkenyl is substituted by a substituent selected form the group consisting of acyl, hydroxyl, cycloalkyl, alkoxy, acyloxy, amino, aminoacyl, nitro, halo, thiol, thioalkyl, alkyl, alkenyl, alkynyl, and heterocyclyl. In some embodiments, the phospholipid of formula (PL-4) is N-dodecanoyl-1,2-di-(9Z-octadecenoyl)-sn-glycero-3-phosphoethanolamine (N-C12-DOPE) or a salt thereof. In one variation, the phospholipid of formula (PL-4) is:

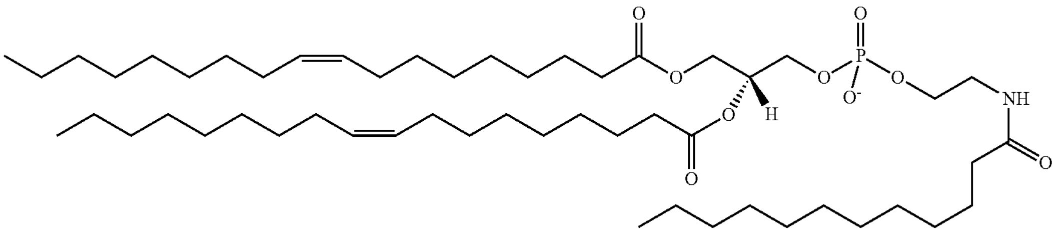 [SMILES: CCCCCCCC/C=C\CCCCCCCC(=O)OC[C@H](COP(=O)([O-])OCCNC(=O)CCCCCCCCCCC)OC(=O)CCCCCCC/C=C\CCCCCCCC]

or a salt thereof.

In some embodiments, the phospholipid of formula (PL-4) is present in the amount of up to about 40 molar percent, about 45 molar percent, about 50 molar percent, about 55 molar percent, about 60 molar percent, about 65 molar percent, about 70 molar percent, about 75 molar percent, about 80 molar percent, about 85 molar percent or about 90 molar percent. In some embodiments, the phospholipid of formula (PL-4) is present in the amount of at least about 30 molar percent, at least about 40 molar percent, at least about 50 molar percent, at least about 60 molar percent, at least about 70 molar percent or at least about 80 molar percent. In some embodiments, the phospholipid of formula (PL-4) is present in the amount of about 30-40 molar percent, about 40-50 molar percent, about 50-60 molar percent, about 60-70 molar percent, about 70-80 molar percent, about 30-50 molar percent or about 50-80 molar percent or about 40-80 molar percent.

In some embodiments, the liposome further comprises 1,2-dioleoyl-sn-glycero-3-phosphocholine (DOPC), PEG conjugated to at least one phospholipid, cholesterol, CHEMS or a combination of the foregoing.

In some aspects, provided is a liposome that comprises at least one phospholipid of formula (A):

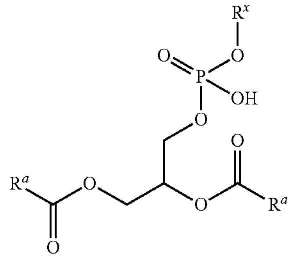

or a salt thereof, wherein $R^X$ is $-SO_2$, wherein the S atom of $-SO_2$ is substituted with an optionally substituted rhodamine, and each $R^a$ is independently a carbon chain. In other embodiments, each $R^a$ is independently an unsaturated carbon chain. In some embodiments, each $R^a$ is independently a saturated carbon chain. In some embodiments, each $R^b$ is a $C_{10-28}$ alkyl. In one variation, the liposome comprises RH-DHPE. In one variation, the liposome comprises N-(lissamine rhodamine B sulfonyl)-1,2-dihexadecanoyl-sn-glycero-3-phosphoethanolamine, or a salt thereof. In one variation, the liposome comprises 1,2-dioleoyl-sn-glycero-3-phosphoethanolamine-N-(lissamine rhodamine B sulfonyl), or a salt thereof. In one variation, the liposome comprises:

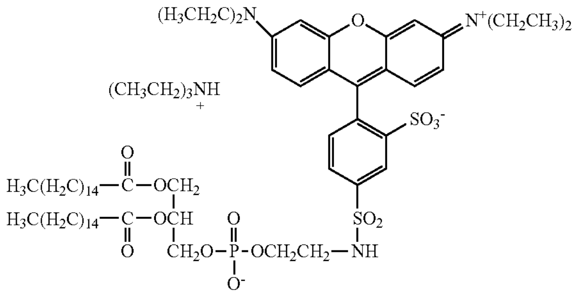

or a salt thereof.

In some embodiments of the foregoing aspect, the liposome that comprises at least one phospholipid of formula (A) may be combined with one or more of the lipids and/or other compounds described herein. For example, in certain variations, the liposome further comprises at least one phosphatidylcholine or phosphatidylethanolamine. In other variations, the liposome further comprises polyethylene glycol conjugated to at least one lipid, including at least one phospholipid. In certain variations, the liposome further comprises cholesterol. In one variation, the liposome composition comprises: DSPC/DSPE-PEG/RH-DHPE, or DSPC/DSPE-PEG/RH-DHPE/Chol, or DSPC/Chol/DSPE-PEG/DOTAP/RH-DHPE.

In some aspects, the liposome comprises at least one compound of formula (B):

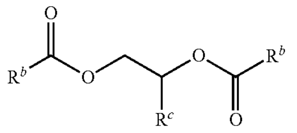

or a salt thereof, wherein: each $R^b$ is independently a carbon chain and $R^c$ is a carbon chain substituted with an optionally substituted amino group or a quaternary ammonium. In some embodiments, each $R^b$ is a saturated carbon chain. In other embodiments, each $R^b$ is an unsaturated carbon chain. In some embodiments, each $R^b$ is a $C_{10-28}$ alkenyl. In certain embodiments, $R^c$ is a —$C_{1-6}$alkyl-$N(CH_3)_2$. In other embodiments, $R^c$ is a —$C_{1-6}$alkyl substituted with

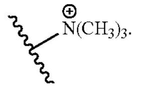

In some embodiments, the at least one compound of formula (B) is 1,2-dioleoyl-3-dimethylammonium-propane (DODAP) or a salt thereof. In some embodiments, the at least one compound of formula (B) is

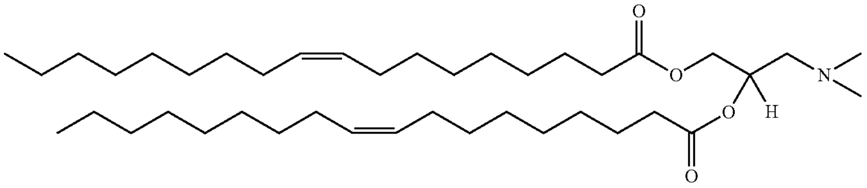 [SMILES: CCCCCCCC/C=C\CCCCCCCC(=O)OCC(CN(C)C)OC(=O)CCCCCCC/C=C\CCCCCCCC]

or a salt thereof. In certain embodiments, the at least one compound of formula (B) is 1,2-dioleoyl-3-trimethylammonium-propane (DOTAP) or a salt thereof. In some embodiments, the at least one compound of formula (B) is:

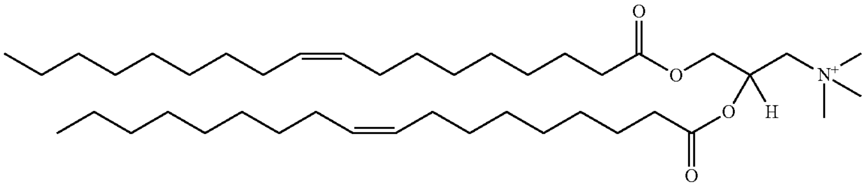

or a salt thereof.

In some embodiments of the foregoing aspect, the liposome that comprises at least one compound of formula (B) may be combined with one or more of the lipids and other compounds described herein. For example, in certain variations, the liposome further comprises at least one phosphatidylcholine or phosphatidylethanolamine. In other variations, the liposome further comprises polyethylene glycol conjugated to at least one lipid, including at least one phospholipid. In certain variations, the liposome further comprises cholesterol. In one variation, the liposome composition comprises DSPC/Chol/DSPE-PEG/DOTAP/RH-DHPE.

In some aspects, the liposome comprises at least one compound of formula (C):

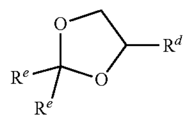

or a salt thereof, wherein $R^d$ is a carbon chain substituted with an optionally substituted amino group, and each $R^e$ is independently a carbon chain. In some embodiments, $R^d$ is a $C_{1-6}$ alkyl substituted with a substituted amino group. In certain embodiments, $R^d$ is a —$C_{1-6}$ alkyl-N(alkyl)$_2$ group. In certain embodiments, $R^d$ is a —$C_{1-6}$ alkyl-N($CH_3$)$_2$ group. In certain embodiments, $R^d$ is —$CH_2CH_2N(CH_3)_2$. In other embodiments, $R^d$ is —$CH_2CH_2CH_2N(CH_3)_2$. In some embodiments, each $R^e$ is a saturated carbon chain. In other embodiments, each $R^e$ is an unsaturated carbon chain. In some embodiments, each $R^e$ is a $C_{10-28}$ alkenyl. In some embodiments, the at least compound of formula (C) is Dlin-KC2-DMA. In some embodiments, the at least one compound of formula (C) is 2,2-dilinoleyl-4-dimethylaminoethyl[1,3]-dioxolane or a salt thereof. In certain embodiments, the at least compound of formula (C) is

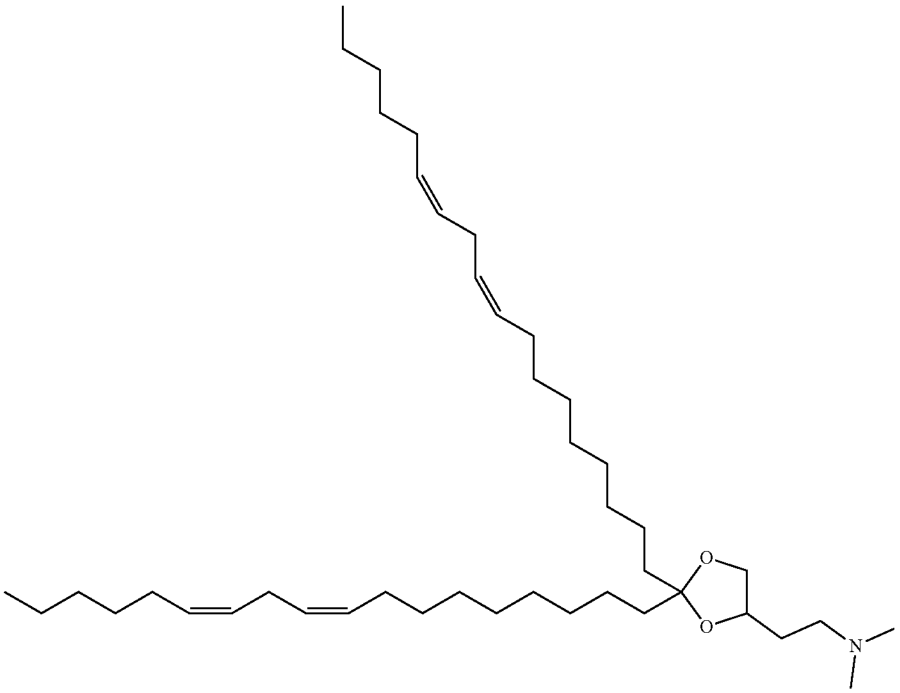 [SMILES: CCCCC/C=C\C/C=C\CCCCCCCCC1(CCCCCCCC/C=C\C/C=C\CCCCC)OCC(CCN(C)C)O1]

or a salt thereof. In other embodiments, the at least compound of formula (C) is Dlin-KC3-DMA. In some embodiments, the at least one compound of formula (C) is 2,2-dilinoleyl-4-dimethylaminopropyl-[1,3]-dioxolane or a salt thereof. In certain variations, the at least compound of formula (C) is

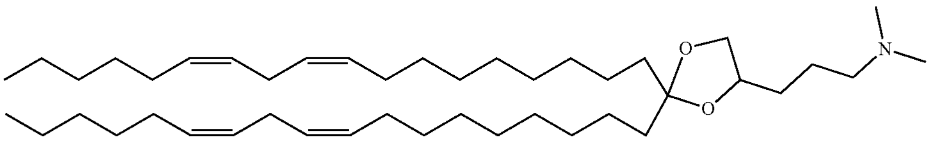 [SMILES: CCCCC/C=C\C/C=C\CCCCCCCCC1(CCCCCCCC/C=C\C/C=C\CCCCC)OCC(CCCN(C)C)O1]

or a salt thereof.

In some embodiments of the foregoing aspect, the liposome that comprises at least one compound of formula (C) may be combined with one or more of the lipids and other compounds described herein. For example, in certain variations, the liposome further comprises at least one phosphatidylcholine or phosphatidylethanolamine. In other variations, the liposome further comprises polyethylene glycol conjugated to at least one lipid, including at least one phospholipid. In certain variations, the liposome further comprises cholesterol. In one variation, the liposome composition comprises DSPC/DMG-PEG/Dlin-KC2-DMA/Chol.

In some aspects, the liposome comprises at least one compound of formula (D):

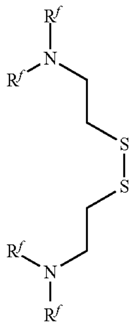

or a salt thereof, wherein each $R^f$ is independently an optionally substituted carbon chain, or the two $R^f$ bonded to the same N atom come together to form an optionally substituted ring. In some embodiments, each $R^f$ is independently a $C_{1-6}$ alkyl that is optionally substituted with one or more —O—C(O)—$C_{10-28}$ alkyl. In other embodiments, the two $R^f$ bonded to the same N atom come together to form a 6-membered ring, wherein the 6-membered ring is substituted with a $C_{1-6}$ alkyl, wherein the $C_{1-6}$ alkyl is further optionally substituted. In one embodiment, the at least one compound of formula (D) is ssPalmm, which corresponds to bis{2-{N-methyl-N-(tetradecanoylpropyl)amino]ethyl} disulfide, or a salt thereof. In one embodiment, the at least one compound of formula (D) is

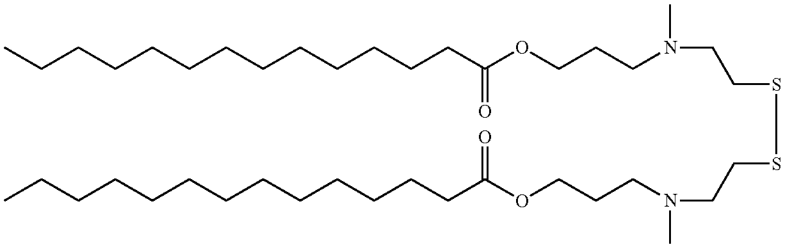 [SMILES: CCCCCCCCCCCCCC(=O)OCCCN(C)CCSSCCN(C)CCCOC(=O)CCCCCCCCCCCCC]

or a salt thereof. In other embodiments, the at least one compound of formula (D) is ssPalme, which corresponds to bis{2-[4-(α-D-tocopherolhemisuccinateethyl)piperidyl] ethyl} disulfide or a salt thereof. In one embodiment, the at least one compound of formula (D) is

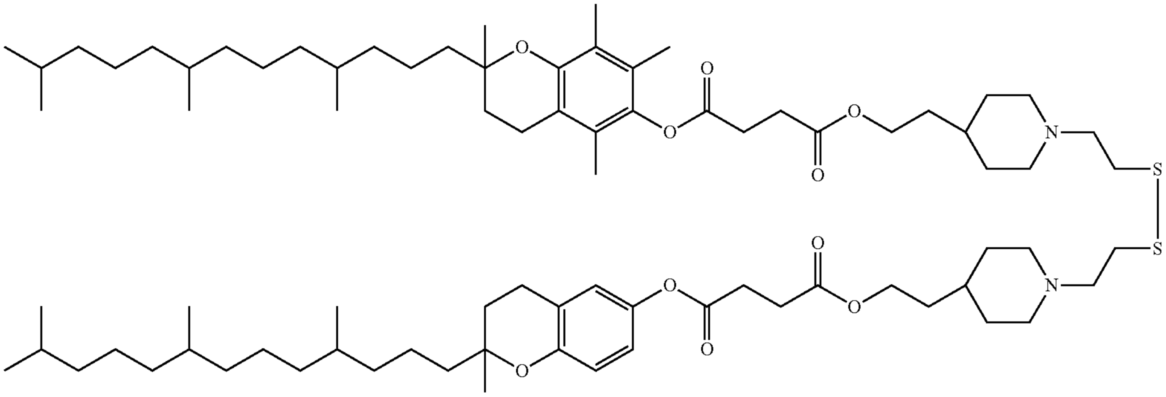 [SMILES: Cc1c(C)c2c(c(C)c1OC(=O)CCC(=O)OCCC1CCN(CCSSCCN3CCC(CCOC(=O)CCC(=O)Oc4ccc5c(c4)CCC(C)(CCCC(C)CCCC(C)CCCC(C)C)O5)CC3)CC1)CCC(C)(CCCC(C)CCCC(C)CCCC(C)C)O2]

or a salt thereof.

In some embodiments of the foregoing aspect, the liposome that comprises at least one compound of formula (D) may be combined with one or more of the lipids and other compounds described herein. For example, in certain variations, the liposome further comprises at least one phosphatidylcholine or phosphatidylethanolamine. In other variations, the liposome further comprises polyethylene glycol conjugated to at least one lipid, including at least one phospholipid. In certain variations, the liposome further comprises cholesterol. In one variation, the liposome composition comprises ssPalmm/SOPC/PEG(2k)-DSG/Chol; or ssPalme/SOPC/PEG(2k)-DSG/Chol.

In another aspect, provided herein is a composition comprising a liposome comprising a phospholipid of formula (PL-2A):

(PL-2A)

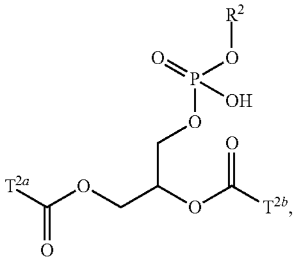

or a salt thereof, wherein:

each of $T^{2a}$ and $T^{2b}$ is a carbon chain; and $R^2$ is alkyl substituted with a quaternary ammonium.

In some embodiments, each of $T^{2a}$ and $T^{2b}$ is independently a saturated or unsaturated carbon chain. In certain variations, the quaternary ammonium is —$N^+$(alkyl)$_3$. In one variation of foregoing, the alkyl is independently C1-6 alkyl, or C1-4 alkyl, or methyl, ethyl, or propyl. In one variation, the phospholipid of Formula (PL-2A) is 1-stearoyl-2-oleoyl-sn-glycero-3-phosphocholine (SOPC) or a salt thereof. In one variation, the phospholipid of Formula (PL-2A) is

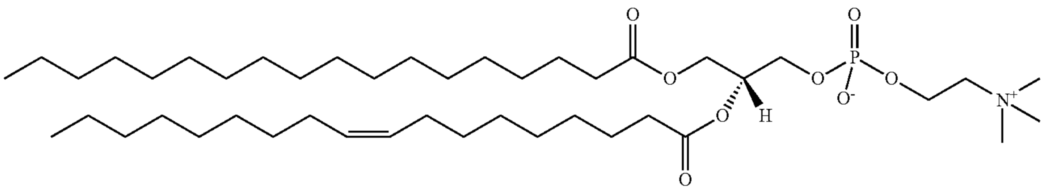 [SMILES: CCCCCCCC/C=C\CCCCCCCC(=O)O[C@H](COC(=O)CCCCCCCCCCCCCCCCC)COP(=O)([O-])OCC[N+](C)(C)C]

or a salt thereof.

In some embodiments of the foregoing aspect, the liposome that comprises at least one phospholipid of formula (PL-2A) may be combined with one or more of the lipids and other compounds described herein. For example, in certain variations, the liposome further comprises at least one phosphatidylcholine or phosphatidylethanolamine. In other variations, the liposome further comprises polyethylene glycol conjugated to at least one lipid, including at least one phospholipid. In certain variations, the liposome further comprises cholesterol. In one variation, the liposome composition comprises ssPalmm/SOPC/PEG(2k)-DSG/Chol; or ssPalme/SOPC/PEG(2k)-DSG/Chol.

In one aspect, the liposome comprises at least one phospholipid having an ethanolamine head group and an unsaturated fatty acid tail, wherein the unsaturated fatty acid tail comprises at least one $C_{10-28}$ carbon chain. In some embodiments, the at least one phospholipid having an ethanolamine head group and an unsaturated fatty acid tail, wherein the unsaturated fatty acid tail comprises at least one $C_{10-28}$ carbon chain is 1,2-distearoyl-sn-glycero-3-phosphocholine. In some embodiments, the liposome further comprises at least one PEGylated phospholipid. In some embodiments, the at least one PEGylated phospholipid is 1,2-distearoyl-sn-glycero-3-phosphoethanolamine. In other embodiments, the at least one PEGylated lipid is 1,2-dimyristoyl-glycerol (DMG). In some embodiments, the liposome further comprises at least one compound of formula (A):

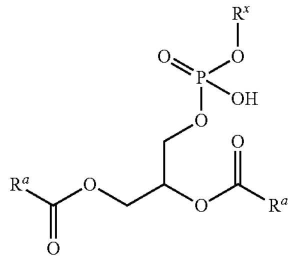

or a salt thereof, as defined above. In some embodiments, the at least one compound of formula (A) is

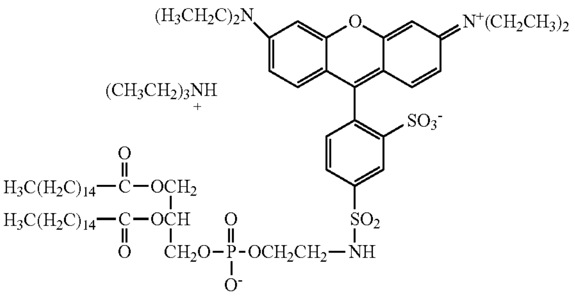

or a salt thereof. In some embodiments, the liposome further comprises at least one sterol. In certain embodiments, the at least one sterol is cholesterol. In certain embodiments, the liposome further comprises at least one compound of formula (B):

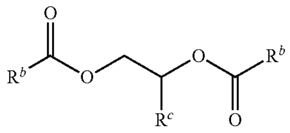

or a salt thereof, as defined above. In some embodiments, at least one compound of formula (B) is 1,2-dioleoyl-3-dimethylammonium-propane (DODAP) or a salt thereof. In certain embodiments, the at least one compound of formula (B) is

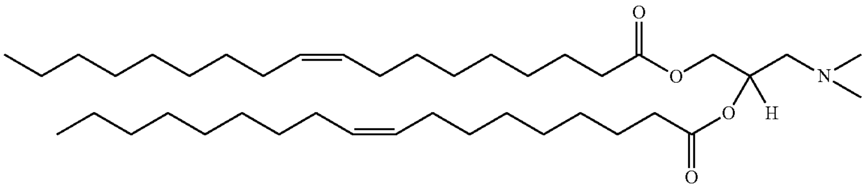 [SMILES: CCCCCCCC/C=C\CCCCCCCC(=O)OCC(CN(C)C)OC(=O)CCCCCCC/C=C\CCCCCCCC]

or a salt thereof.

In other embodiments, the liposome composition further comprises at least one compound of formula (C):

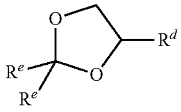

or a salt thereof, as defined above. In some embodiments, the at least one compound of formula (C) is Dlin-KC2-DMA. In other embodiments, the at least one compound of formula (C) is Dlin-KC3-DMA. In certain embodiments, the at least one compound of formula (C) is

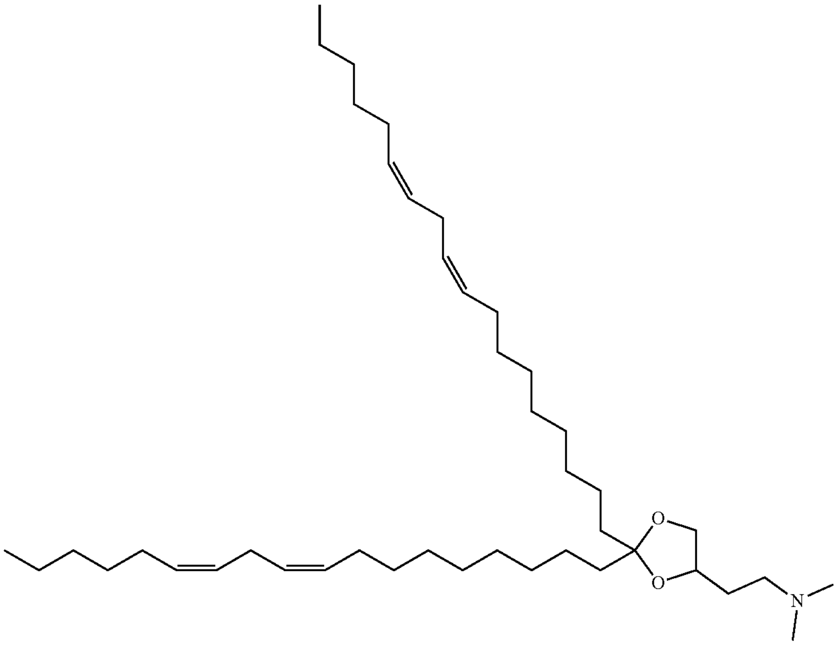 [SMILES: CCCCC/C=C\C/C=C\CCCCCCCCC1(CCCCCCCC/C=C\C/C=C\CCCCC)OCC(CCN(C)C)O1]

or a salt thereof. In other embodiments, the at least one compound of formula (C) is

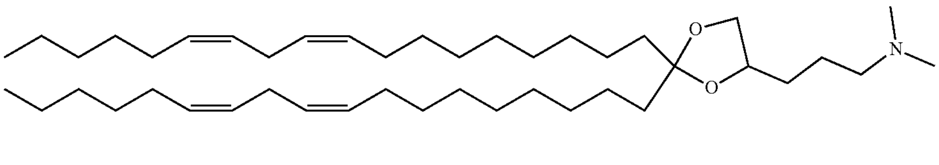 [SMILES: CCCCC/C=C\C/C=C\CCCCCCCCC1(CCCCCCCC/C=C\C/C=C\CCCCC)OCC(CCCN(C)C)O1]

or a salt thereof.

In one aspect, provided herein is a liposome composition comprising at least one compound of formula (D):

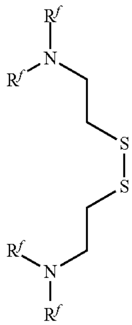

or a salt thereof, as defined above. In some embodiments, the at least one compound of formula (D) is bis{2-{N-methyl-N-(tetradecanoylpropyl)amino]ethyl} disulfide or a salt thereof. In one embodiment, the at least one compound of formula (D) is

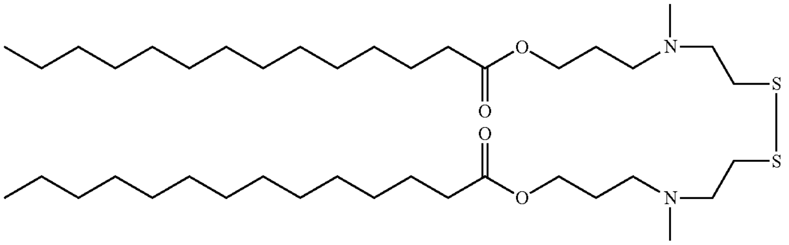 [SMILES: CCCCCCCCCCCCCC(=O)OCCCN(C)CCSSCCN(C)CCCOC(=O)CCCCCCCCCCCCC]

or a salt thereof. In other embodiments, the at least one compound of formula (D) is ssPalme, which corresponds to bis{2-[4-(α-D-tocopherolhemisuccinateethyl)piperidyl] ethyl} disulfide or a salt thereof. In one embodiment, the at least one compound of formula (D) is

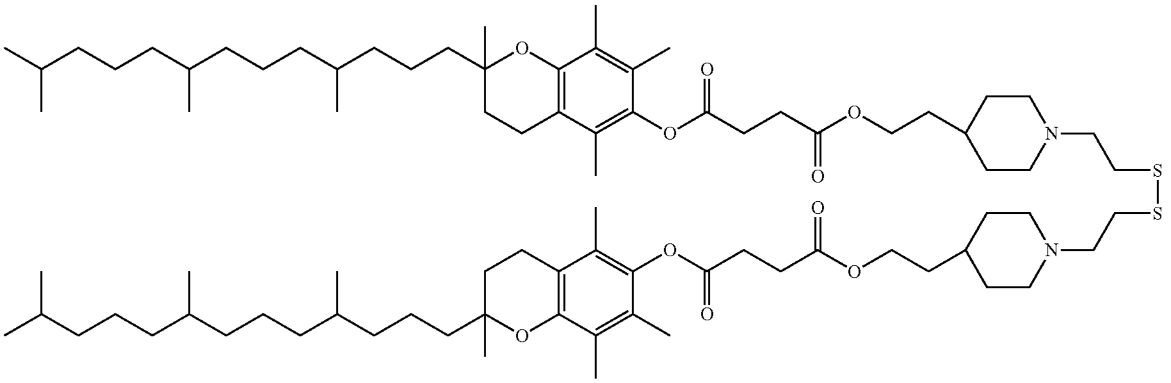 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

or a salt thereof. In some embodiments, the liposome further comprises at least one phospholipid having an ethanolamine head group and an unsaturated fatty acid tail, wherein the unsaturated fatty acid tail comprises at least one $C_{10-28}$ carbon chain. In some embodiments, the at least one phospholipid having an ethanolamine head group and an unsaturated fatty acid tail, wherein the unsaturated fatty acid tail comprises at least one $C_{10-28}$ carbon chain is 1-stearoyl-2-oleoyl-sn-glycero-3-phosphocholine (SOPC). In some embodiments, the liposome further comprises at least one PEGylated phospholipid. In some embodiments, the at least one PEGylated phospholipid is 1,2-diastearoyl glycerol (DSG). In some embodiments, the at least one PEGylated phospholipid is PEG(2k)-DSG. In some embodiments, the liposome further comprises at least one sterol. In certain embodiments, the at least one sterol is cholesterol.

In one aspect, provided herein is a liposome composition comprising one or more phospholipid having a polar head group selected from the group consisting of glycerol, choline, phosphate and serine and a fatty acid tail comprising a $C_{10-28}$ aliphatic chain. In some embodiments, the one or more phospholipid having a polar head group selected from the group consisting of glycerol, choline, phosphate and serine and a fatty acid tail comprising a $C_{10-28}$ aliphatic chain is 1,2-distearoyl-sn-glycero-3-phosphate (DSPA). In some embodiments, the liposome composition further comprises at least one phospholipid having an ethanolamine head group and an unsaturated fatty acid tail, wherein the unsaturated fatty acid tail comprises at least one $C_{10-28}$ carbon chain. In some embodiments, the at least one phospholipid having an ethanolamine head group and an unsaturated fatty acid tail, wherein the unsaturated fatty acid tail comprises at least one $C_{10-28}$ carbon chain is 1,2-dioleoyl-sn-glycero-3-phosphocholine (DOPC). In some embodiments, the liposome further comprises at least one PEGylated phospholipid. In some embodiments, the at least one PEGylated phospholipid is 1,2-distearoyl-sn-glycero-3-phosphoethanolamine. In some embodiments, the liposome further comprises at least one sterol. In certain embodiments, the at least one sterol is cholesterol.

In one aspect, provided is a liposome composition comprising:

DSPC/DSPE-PEG/RH-DHPE,
DSPC/DSPE-PEG/RH-DHPE/Chol,
DSPC/DODAP/DSPE-PEG/Chol,
DSPC/DMG-PEG/Dlin-KC2-DMA/Chol,
ssPalmm/SOPC/PEG(2k)-DSG/Chol,
ssPalme/SOPC/PEG(2k)-DSG/Chol,
DSPA/DOPC/DSPE-PEG/Chol,
N-C12-DOPE/DOPC,
N-C12-DOPE/DOPC/DSPE-PEG,
N-C12-DOPE/DOPC/DSPE-PEG/Chol,
N-C12-DOPE/DPPE/DOPC/DSPE-PEG,
N-C12-DOPE/DOPE/DOPC/DSPE-PEG,
DOPE/DOPG/DSPE-PEG,
DOPE/DSPA/DSPE-PEG,
DOPE/DC-Chol/DSPE-PEG,
DOPE/DOPC/DSPE-PEG,
DOPE/DPPG/DOPC/DSPE-PEG,
DOPE/DOPC/DSPE-PEG/Chol,
DOPE/DOPS/DSPE-PEG,
DOPE/CHEMS,
DOPE/CHEMS/DSPE-PEG,
DOPE/CHEMS/DSPE-PEG/Chol,
DOPE/CHEMS/DOPC/DSPE-PEG, or a salt thereof, or any combination of the foregoing.

In some variations of the foregoing, the PEG may be present in the liposome at a molecular weight that ranges from about 200 Da to about 40,000 Da. In some embodiments, polyethylene glycol (PEG) may be present in the liposome of the present disclosure at a molecular weight that ranges from about 200 Da to about 10,000 Da. In some embodiments, polyethylene glycol (PEG) may be present in the liposome of the present disclosure at a molecular weight of about 200 Da, about 300 Da, about 400 Da, about 500 Da, about 600 Da, about 700 Da, about 800 Da, about 900 Da, about 1,000 Da, about 1,500 Da, about 2,000 Da, about 2,500 Da, about 3,000 Da, about 3,500 Da, about 4,000 Da, about 4,500 Da, about 5,000 Da, about 5,500 Da, about 6,000 Da, about 6,500 Da, about 7,000 Da, about 7,500 Da, about 8,000 Da, about 8,500 Da, about 9,000 Da, about 9,500 Da, or about 10,000 Da; or between about 200 Da and about 10,000 Da.

In some variations of the foregoing, the lipids, including the phospholipids, described herein may be present in the liposome composition in salt form. For example, in one variation, the phospholipid is DOPE or a salt thereof.

Carbohydrates

Other aspects of the present disclosure relate to compositions containing carbohydrates encapsulated within a liposome of the present disclosure. Any suitable carbohydrate known in the art may be used. Suitable carbohydrates that may be used include, for example, monosaccharides, phosphorylated monosaccharides, disaccharides, phosphorylated disaccharides, oligosaccharides, phosphorylated oligosaccharides, polysaccharides, phosphorylated polysaccharides, nucleotide sugars, endogenous carbohydrates, and phosphorylated endogenous carbohydrates. In some embodiments, the carbohydrate is an endogenous carbohydrate. In some variations, the carbohydrate is a phosphorylated carbohydrate.

In some embodiments, a phosphorylated carbohydrate of the present disclosure is an endogenous carbohydrate. In some embodiments, an endogenous carbohydrate is a carbohydrate that is found as a natural product in a subject (including, for example, a human). It should be understood, however, that an endogenous carbohydrate may be either (i) naturally produced by a subject (including, for example, a human) and extracted from the living cells of such subject; or (ii) synthetically made. In some embodiments, the endogenous carbohydrate is produced in vivo by a subject (including, for example, human). In other embodiments, the endogenous carbohydrate is naturally produced by a cell derived from a subject (including, for example, human), such as a cultured cell line. Thus, the source of such endogenous carbohydrates may include, for example, a synthetic source (e.g., chemical synthesis) or a natural source (e.g., extraction, isolation, or purification from a subject or cell that naturally produces the endogenous carbohydrate or a recombinant cell, such as a bacterial cell, that has been genetically engineered to produce the endogenous carbohydrate). Endogenous carbohydrates may include, for example, carbohydrates involved in protein and lipid glycosylation.

Suitable endogenous carbohydrates include, for example, a monosaccharide, a phosphorylated monosaccharide, a disaccharide, a phosphorylated disaccharide, an oligosaccharide, a phosphorylated oligosaccharide, a polysaccharide, a phosphorylated polysaccharide, mannose, a phosphorylated mannose, a mannofuranose, a phosphorylated mannofuranose, a mannopyranos, a phosphorylated mannopyranos, mannose-1-phosphate, mannose-6-phosphate, a nucleotide sugar, a uridine diphosphate, a guanine diphosphate, a cytosine monophosphate, fucose, GDP-fucose, a sialic acid, CMP-sialic acid, N-acetylneuraminic acid (Neu5Ac), and CMP-Neu5Ac. In one variation, the carbohydrate is mannose-1-phosphate, also referred to herein as "M1P".

In some embodiments, the carbohydrate is a phosphorylated endogenous carbohydrate. In some embodiments, the phosphorylated endogenous carbohydrate includes, for example, a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof. In some embodiments, the phosphorylated endogenous carbohydrate is a phosphorylated monosaccharide. In some embodiments, the phosphorylated endogenous carbohydrate is mannose-1-phosphate. In some embodiments, the phosphorylated endogenous carbohydrate is mannose-6-phosphate.

In some variations of the foregoing embodiments, any of the carbohydrates listed herein may be present in the liposome composition in salt form. For example, in one variation, the phosphorylated carbohydrate is mannose-1-phosphate or a salt thereof.

Liposome Composition Encapsulating Carbohydrate

Any liposome described herein can be used to encapsulate a carbohydrate in a liposome composition. Any carbohydrate described herein can be encapsulated in a liposome in a liposome composition.

In one aspect, provided herein is a composition comprising:

a liposome comprising:

i) 1,2-dioleoyl-sn-glycero-3-phosphoethanolamine (DOPE) or a salt thereof ii) one or more stabilizer selected from (a) one or more phospholipid having a polar head group selected from the group consisting of glycerol, choline, phosphate and serine and a fatty acid tail comprising a $C_{10-28}$ aliphatic chain, or (b) an acidic cholesterol ester, or a mixture of (a) and (b); and iii) PEG conjugated to at least one phospholipid; and at least one endogenous phosphorylated carbohydrate, wherein the at least one endogenous phosphorylated carbohydrate is encapsulated in the liposome.

In another aspect, provided herein is a composition comprising a liposome comprising:

i) a phospholipid of formula (PL-1):

(PL-1)

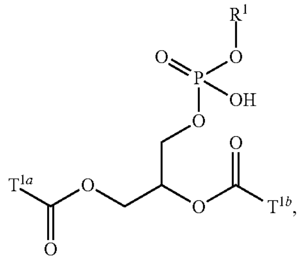

or a salt thereof, wherein:

at least one of $T^{1a}$ and $T^{1b}$ is an unsaturated carbon chain; and $R^1$ is aminoalkyl;

ii) at least one phospholipid of formula (PL-2), at least one phospholipid of formula (PL-3), or at least one cholesterol ester of formula (CE), or any combination of the foregoing:

(PL-2)

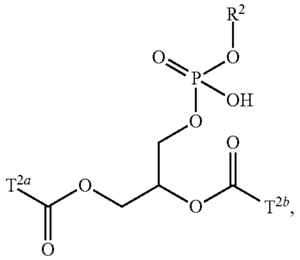

or a salt thereof, wherein:

each of $T^{2a}$ and $T^{2b}$ is an unsaturated carbon chain; and $R^2$ is alkyl substituted with a quaternary ammonium, glycerol, or alkyl substituted with —COOH and —$NH_2$;

(PL-3)

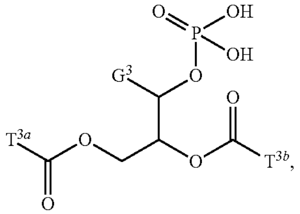

or a salt thereof, wherein:

each of $T^{3a}$ and $T^{3b}$ is a saturated carbon chain; and $G^3$ is H or alkyl substituted with at least one —OH; and (CE)

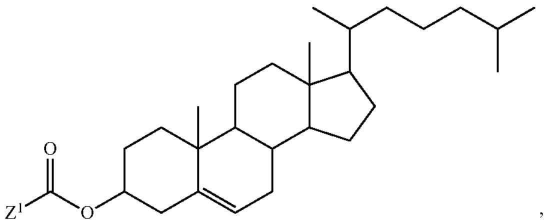

or a salt thereof, wherein:

$Z^1$ is alkyl substituted with —COOH; and iii) polyethylene glycol (PEG), wherein the PEG is conjugated to at least one phospholipid.

at least one phosphorylated endogenous carbohydrate, wherein the at least one endogenous carbohydrate is encapsulated in the liposome.

In another aspect, provided herein is a composition comprising a liposome comprising:

i) a phospholipid of formula (PL-1):

(PL-1)

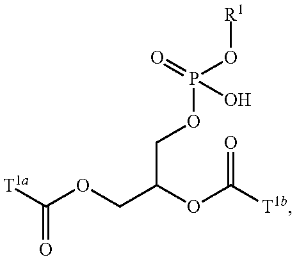

or a salt thereof, wherein:

at least one of $T^{1a}$ and $T^{1b}$ is an unsaturated carbon chain; and $R^1$ is aminoalkyl;

ii) at least one phospholipid of formula (PL-2), at least one phospholipid of formula (PL-3), or at least one cholesterol ester of formula (CE), or any combination of the foregoing:

(PL-2)

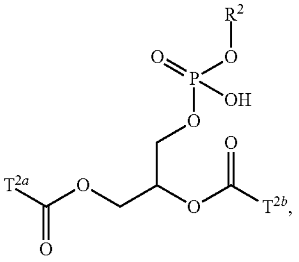

or a salt thereof, wherein:

each of $T^{2a}$ and $T^{2b}$ is an unsaturated carbon chain; and $R^2$ is alkyl substituted with a quaternary ammonium, glycerol, or alkyl substituted with —COOH and —$NH_2$;

(PL-3A)

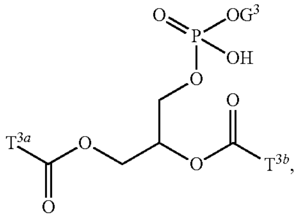

or a salt thereof, wherein:

each of $T^{3a}$ and $T^{3b}$ is a carbon chain; and $G^3$ is H or alkyl substituted with at least one —OH; and (CE)

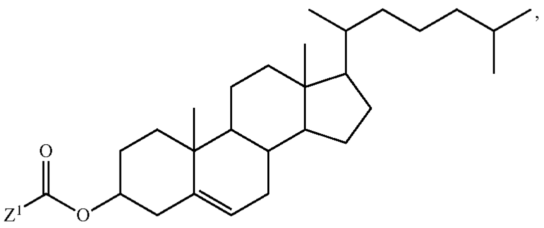

or a salt thereof, wherein:

$Z^1$ is alkyl substituted with —COOH; and iii) polyethylene glycol (PEG), wherein the PEG is conjugated to at least one phospholipid.

at least one phosphorylated endogenous carbohydrate, wherein the at least one endogenous carbohydrate is encapsulated in the liposome.

In another aspect, provided herein is a composition comprising a liposome comprising:

i) N-dodecanoyl-1,2-di-(9Z-octadecenoyl)-sn-glycero-3-phosphoethanolamine (N-C12-DOPE) or a salt thereof;

ii) 1,2-dioleoyl-sn-glycero-3-phosphocholine (DOPC) or a salt thereof; and at least one phosphorylated endogenous carbohydrate, wherein the at least one endogenous carbohydrate is encapsulated in the liposome.

In another aspect, provided herein is a composition comprising a liposome comprising:

i)

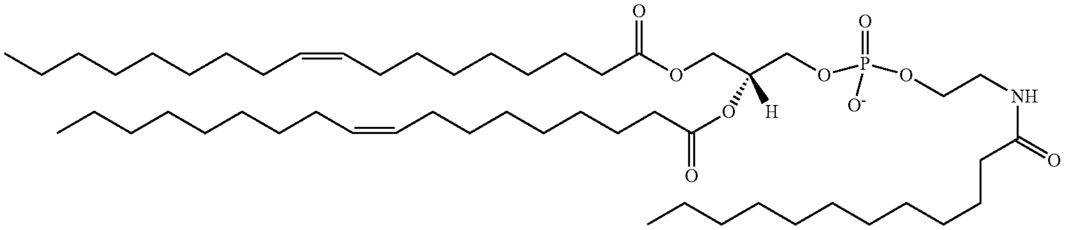 [SMILES: CCCCCCCC/C=C\CCCCCCCC(=O)OC[C@H](COP(=O)([O-])OCCNC(=O)CCCCCCCCCCC)OC(=O)CCCCCCC/C=C\CCCCCCCC]

or a salt thereof;

ii)

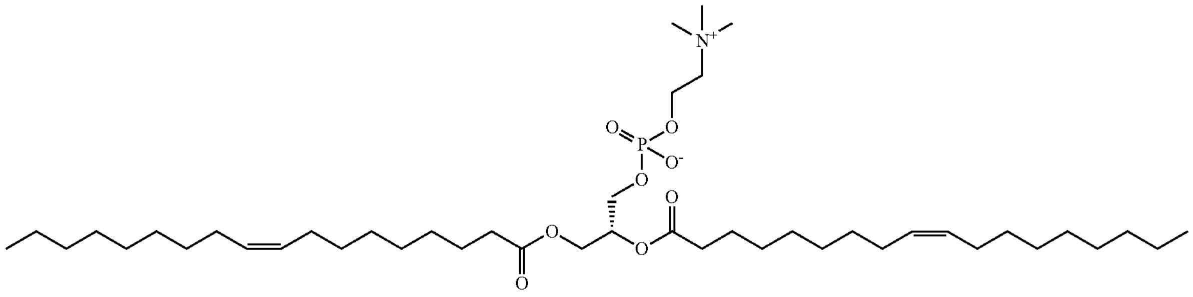 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

or a salt thereof; and at least one phosphorylated endogenous carbohydrate, wherein the at least one endogenous carbohydrate is encapsulated in the liposome.

In another aspect, provided herein is a composition comprising a liposome comprising a phospholipid of formula (PL-4):

(PL-4)

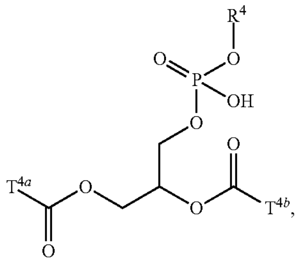

or a salt thereof, wherein:

at least one of $T^{1a}$ and $T^{1}$ is an unsaturated carbon chain; and $R^4$ is an aliphatic chain comprising an amide moiety; and at least one phosphorylated endogenous carbohydrate, wherein the at least one endogenous carbohydrate is encapsulated in the liposome.

The at least one phosphorylated endogenous carbohydrate of the compositions described herein is present in the amount of about 0.1-75 mM, about 0.1-0.5 mM, about 0.1-40 mM, about 0.1-30 mM, about 0.1-20 mM, about 0.1-10 mM, about 0.5-1.0 mM, about 1.0-1.5 mM, about 1.5-2.0 mM, about 2.0-2.5 mM, about 2.5-3.0 mM, about 3.0-3.5 mM, about 3.5-4.0 mM, about 4.0-4.5 mM, about 4.5-5.0 mM, about 5.0-7.5 mM, about 7.5-10 mM, about 10-15 mM, about 15-20 mM, about 20-30 mM, about 30-40 mM, about 40-50 mM, about 50-75 mM, about 0.1-2.5 mM, about 2.5-5.0 mM, about 5.0-10 mM, about 10-25 mM, about 25-50 mM, about 50-75 mM, about 0.1-10 mM, about 10-30 mM or about 30-75 mM.

Pharmaceutical Compositions

Compositions of the present disclosure containing a liposome of the present disclosure and a phosphorylated carbohydrate of the present disclosure encapsulated in the liposome can be incorporated into a variety of formulations for therapeutic use (e.g., by administration) or in the manufacture of a medicament (e.g., for delivering a carbohydrate of the present disclosure to a subject in need thereof and/or cell interior of a subject in need thereof and/or for treating or preventing a disease or disorder such as a congenital disorder of glycosylation (CDG) in a subject in need thereof) by combining the composition with appropriate carriers (including, for example, pharmaceutically acceptable carriers or diluents), and may be formulated, for example, into preparations in liquid, aerosolized, semisolid, or powder forms.

In some embodiments, carriers include pharmaceutically acceptable carriers, excipients, or stabilizers that are nontoxic to the cell or subject being exposed thereto at the dosages and concentrations employed. Often the physiologically acceptable carrier is an aqueous pH buffered solution. Suitable physiologically acceptable carriers include, for example, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. In certain embodiments, wherein the physiologically acceptable carrier is a salt-forming counterion such as sodium, the sodium ion is present in solution alongside other ions, including, for example, chloride. In certain embodiments, the physiologically acceptable carrier comprises a saline solution. In some embodiments, the saline solution is present in the amount of 0-200 mM. In other embodiments, the saline solution is present in the amount of 0-175 mM. In still other embodiments, the saline solution is present in the amount of 0-150 mM.

In other embodiments, the pharmaceutically acceptable carrier is glycerol, xylitol, sucrose, trehalose, polysorbate 80, alanine, proline, taurine, betaine, octopine, histidine, calcium citrate, ammoinum sulfate, urea, or cetylmethylammonium.

Suitable formulations include, for example, solutions, injections, inhalants, microspheres, aerosols, gels, ointments, creams, lotions, powders, dry vesicular powders, tablets, and capsules. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Such diluents include, for example, distilled water, buffered water, physiological saline, phosphate buffered saline (PBS), Ringer's solution, dextrose solution, and Hank's solution. A pharmaceutical composition or formulation of the present disclosure can further include, for example, other carriers or non-toxic, nontherapeutic, non-immunogenic stabilizers, and excipients. The compositions can also include additional substances to approximate physiological conditions, such as pH adjusting and buffering agents, toxicity adjusting agents, wetting agents and detergents. A pharmaceutical composition of the present disclosure can also include any of a variety of stabilizing agents, such as an antioxidant for example.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Pharmaceutical Dosages

Pharmaceutical compositions of the present disclosure containing a composition containing a liposome of the present disclosure and a carbohydrate of the present disclosure encapsulated by the liposome may be used (e.g., administered to a subject in need of treatment with a carbohydrate of the present disclosure, such as a human individual) in accord with known methods, such as oral administration, intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the compositions of the present disclosure containing a liposome of the present disclosure and a carbohydrate of the present disclosure encapsulated by the liposome, normal dosage amounts may vary from 10 ng/kg up to 100 mg/kg of a subject's body weight per day.

Administration of a composition of the present disclosure containing a liposome of the present disclosure and a carbohydrate of the present disclosure encapsulated by the liposome can be continuous or intermittent, depending, for example, on the recipient's physiological condition, whether the purpose of the administration is therapeutic or prophylactic, and other factors known to skilled practitioners.

It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Thus, in some variations, the compositions provided herein may be chronically or intermittently administered to a subject (including, for example, a human) in need thereof. In certain variations, chronic administration is administration of the medicament(s) in a continuous as opposed to acute mode, so as to maintain the initial therapeutic effect (activity) for an extended period of time. In certain variations, intermittent administration is treatment that is not consecutively done without interruption, but rather is cyclic in nature.

Manufacturing Methods

In certain aspects, provided herein are methods of producing the liposome compositions described herein. In certain embodiments, the method comprises: a) dissolving lipids in solvent to produce a mixture; b) drying the mixture to form a thin-film; c) hydrating the thin-film with an aqueous solution comprising a phosphorylated carbohydrate; d) heating the solution in step c) to re-suspend the thin-film, thereby producing a suspension; and e) subjecting the suspension to at least one freeze-thaw cycle to produce the liposomal composition. In some variations, the method further comprises: adjusting the size of the liposome composition by sonication, extrusion, or microfluidization, or any combination thereof.

In some variations of the foregoing, the method further comprises adjusting the pH of the liposomal composition. In other variations, the method further comprises removing unencapsulated phosphorylated carbohydrate by dialysis, solid phase extraction, or tangential flow filtration.

In one embodiment, the lipid components of the liposome are dissolved in chloroform, and the resulting mixture is heated to dissolve the lipids completely. Then, the mixture is dried to a thin-film coating on, for example, a flask or tube. The thin films are then hydrated with a solution containing mannose-1-phosphate, and the resulting suspension is heated, vortexed, and sonicated to produce a complete suspension of lipids. The liposome suspension is then subjected to freeze-thaw cycles, followed by sizing, using, for example: sonication, extrusion, or microfluidization. In some variations, the pH of the solution is adjusted and/or unencapsulated mannose-1-phosphate is removed from the formulation using techniques such as dialysis, solid phase extraction, or tangential flow filtration.

Therapeutic Uses

The present disclosure provides compositions containing a liposome of the present disclosure and a phosphorylated carbohydrate of the present disclosure encapsulated by the liposome that are capable of delivering the carbohydrate into the interior of a cell. These compositions are useful for delivering phosphorylated carbohydrates of the present disclosure to a subject in need of such carbohydrates.

In some embodiments, the subject is a mammal, such as a human, domestic animal, such as a feline or canine subject, farm animal (e.g., bovine, equine, caprine, ovine, and porcine subject), wild animal (whether in the wild or in a zoological garden), research animal, such as mouse, rat, rabbit, goat, sheep, pig, dog, and cat, and birds. In one embodiment, the subject is a human.

In some variations, the subject may be at risk. For example, in one variation, the subject is an at risk human. A subject at risk of developing a particular disease, disorder, or condition, such as a congenital disorder of glycosylation, may or may not have detectable disease or symptoms of disease, and may or may not have displayed detectable disease or symptoms of disease prior to the treatment methods described herein. In certain variations, an individual "at risk" is an individual having risk factors, which are measurable parameters that correlate with development of a particular disease, disorder, or condition, as known in the art. A subject having one or more of these risk factors has a higher probability of developing a particular disease, disorder, or condition such as a congenital disorder of glycosylation, than a subject without one or more of these risk factors.

In some embodiments, congenital disorders of glycosylation (CDG) is a group of genetic disorders that result in errors of metabolism in which glycosylation of a variety of tissue proteins and/or lipids is deficient or defective. Congenital disorders of glycosylation may also be known as CDG syndromes. CDG syndromes may often cause serious, occasionally fatal, malfunction of several different organ systems, such as the nervous system, brain, muscles, and intestines, in affected infants. Manifestations of CDG syndromes may range from severe developmental delay and hypotonia beginning in infancy, to hypoglycemia and protein-losing enteropathy with normal development. Developmental delay can be a common initial indication for a CDG diagnosis. One of the most common subtype of CDG syndromes is CDG-Ia (also known as PMM2-CDG) where the genetic defect leads to the loss of phosphomannomutase 2, which is the enzyme responsible for the conversion of mannose-6-phosphate into mannose-1-phosphate.

CDG syndromes may be classified as type I (CDG-I) and type II (CDG-II). Such classification may depend on the nature and location of the biochemical defect in the metabolic pathway relative to the action of oligosaccharyltransferase. Methods for screening for CDG subtype may include the analysis of transferrin glycosylation status by, for example, isoelectric focusing or ESI-MS. CDG type I include, for example, Ia (PMM2-CDG), Ib (MPI-CDG), Ic (ALG6-CDG), Id (ALG3-CDG), Ie (DPM1-CDG), If (MPDU1-CDG), Ig (ALG12-CDG), Ih (ALG8-CDG), Ii (ALG2-CDG), Ij (DPAGT1-CDG), Ik (ALG1-CDG), 1L (ALG9-CDG), Im (DOLK-CDG), In (RFT1-CDG), Io (DPM3-CDG), Ip (ALG11-CDG), Iq (SRD5A3-CDG), Ir (DDOST-CDG), DPM2-CDG, TUSC3-CDG, MAGT1-CDG, DHDDS-CDG, and I/IIx. CDG type II include, for example, IIa (MGAT2-CDG), IIb (GCS1-CDG), IIc (SLC335C1-CDG), IId (B4GALT1-CDG), IIe (COG7-CDG), IIf (SLC35A1-CDG), IIg (COG1-CDG), IIh (COG8-CDG), IIi (COG5-CDG), IIj (COG4-CDG), IIL (COG6-CDG), ATP6VOA2-CDG, MAN1B1-CDG, and ST3GAL3-CDG.

Congenital disorders of glycosylation (CDG) that may be treated with compositions of the present disclosure containing a liposome of the present disclosure and a carbohydrate of the present disclosure encapsulated by the liposome include, for example, Ia (PMM2-CDG), Ib (MPI-CDG), Ic (ALG6-CDG), Id (ALG3-CDG), Ie (DPM1-CDG), If (MPDU1-CDG), Ig (ALG12-CDG), Ih (ALG8-CDG), Ii (ALG2-CDG), Ij (DPAGT1-CDG), Ik (ALG1-CDG), 1L (ALG9-CDG), Im (DOLK-CDG), In (RFT1-CDG), Io (DPM3-CDG), Ip (ALG11-CDG), Iq (SRD5A3-CDG), Ir (DDOST-CDG), DPM2-CDG, TUSC3-CDG, MAGT1-CDG, DHDDS-CDG, I/IIx, IIa (MGAT2-CDG), IIb (GCS1-CDG), IIc (SLC335C1-CDG), IId (B4GALT1-CDG), IIe (COG7-CDG), IIf (SLC35A1-CDG), IIg (COG1-CDG), IIh (COG5-CDG), IIi (COG5-CDG), IIj (COG4-CDG), IIL (COG6-CDG), ATP6VOA2-CDG, MAN1B1-CDG, and ST3GAL3-CDG.

In some embodiments, "treatment" or "treating" includes an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

In some embodiments, "prevention" or "preventing" includes any treatment of a disease or condition that causes the clinical symptoms of the disease or condition not to develop. Compounds may, in some embodiments, be administered to a subject (including a human) who is at risk or has a family history of the disease or condition.

In some variations, an "effective amount" is at least an amount effective, at dosages and for periods of time necessary, to achieve the desired therapeutic or prophylactic result. An effective amount can be provided in one or more administrations.

In some variations, a "therapeutically effective amount" is at least the minimum concentration required to effect a measurable improvement of a particular disease, disorder, or condition, such as a congenital disorder of glycosylation. A therapeutically effective amount herein may vary according to factors such as the disease state, age, sex, and weight of the subject, and the ability of the lipid compositions of the present disclosure to elicit a desired response in the subject. A therapeutically effective amount is also one in which any toxic or detrimental effects of the lipid compositions of the present disclosure are outweighed by the therapeutically beneficial effects.

In one aspect, provided herein is a method for delivering a phosphorylated carbohydrate to a subject in need thereof. In some embodiments, the method comprises administering to the subject any of the compositions described herein.

In another aspect, provided herein is a method for delivering a phosphorylated carbohydrate to a cell interior of a subject in need thereof. In some embodiments, the method comprises administering to the subject any of the compositions described herein. In some embodiments, at least a portion of the administered composition traverses the cell plasma membrane to deliver the carbohydrate to the cell interior.

In another aspect, provided herein is a method for treating a congenital disorder of glycosylation (CDG) in a subject in need thereof. In some embodiments, the method comprises administering to the subject any of the compositions described herein. In some embodiments, the congenital disorder of glycosylation (CDG) is a CDG-Ia disorder. In some embodiments, the administration of the composition induces a 0.05-fold to at least a 3-fold increase in cellular production of higher-order lipid-linked oligosaccharides in the human, as compared to cellular production of higher-order lipid-linked oligosaccharides in the human in the absence of administering the composition to the subject.

Articles of Manufacture and Kits

The present disclosure also provides articles of manufacture and/or kits containing a composition of the present disclosure containing a liposome of the present disclosure and a carbohydrate of the present disclosure encapsulated by the liposome. Articles of manufacture and/or kits of the present disclosure may include one or more containers comprising a purified composition of the present disclosure. Suitable containers may include, for example, bottles, vials, syringes, and IV solution bags. The containers may be formed from a variety of materials such as glass or plastic. In some embodiments, the articles of manufacture and/or kits further include instructions for use in accordance with any of the methods of the present disclosure. In some embodiments, these instructions comprise a description of administration of the composition containing a liposome of the present disclosure and a carbohydrate of the present disclosure encapsulated by the liposome to deliver the carbohydrate to a subject in need thereof, to deliver the carbohydrate to a cell interior of a subject in need thereof, or to treat a congenital disorder of glycosylation (CDG) to a subject in need thereof, according to any of the methods of the present disclosure. In some embodiments, the instructions comprise a description of how to detect a congenital disorder of glycosylation (CDG), for example in a subject, in a tissue sample, or in a cell. The article of manufacture and/or kit may further comprise a description of selecting a subject suitable for treatment based on identifying whether that subject has the disease and the stage of the disease.

The instructions generally include information as to dosage, dosing schedule, and route of administration for the intended treatment. The containers may be unit doses, bulk packages (e.g., multi-dose packages) or sub-unit doses. Instructions supplied in the articles of manufacture and/or kits of the present disclosure are typically written instructions on a label or package insert (e.g., a paper sheet included in the article of manufacture and/or kit), but machine-readable instructions (e.g., instructions carried on a magnetic or optical storage disk) are also acceptable.

The label or package insert indicates that the composition is used for delivering a carbohydrate and/or treating, e.g., a congenital disorder of glycosylation (CDG). Instructions may be provided for practicing any of the methods described herein.

The articles of manufacture and/or kits of the present disclosure may be in suitable packaging. Suitable packaging includes, for example, vials, bottles, jars, and flexible packaging (e.g., sealed Mylar or plastic bags). Also contemplated are packages for use in combination with a specific device, such as an inhaler, nasal administration device (e.g., an atomizer) or an infusion device such as a minipump. An article of manufacture and/or kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is a carbohydrate capable of treating a congenital disorder of glycosylation (CDG) and/or improving one or more symptoms thereof. The container may further comprise a second pharmaceutically active agent.

Articles of manufacture and/or kits may optionally provide additional components such as buffers and interpretive information. Normally, the article of manufacture and/or kit comprises a container and a label or package insert(s) on or associated with the container.

ENUMERATED EMBODIMENTS

The following enumerated embodiments are representative of some aspects of the invention.

1. A composition comprising:
   a liposome comprising:
   i) 1,2-dioleoyl-sn-glycero-3-phosphoethanolamine (DOPE);
   ii) one or more stabilizer selected from the group consisting of
      (a) one or more phospholipid having a polar head group selected from the group consisting of glycerol, choline, phosphate and serine and a fatty acid tail comprising a $C_{10-28}$ aliphatic chain, and
      (b) an acidic cholesterol ester, or a mixture of (a) and (b); and
   iii) PEG conjugated to at least one phospholipid; and
   at least one endogenous phosphorylated carbohydrate, wherein the at least one endogenous phosphorylated carbohydrate is encapsulated in the liposome.
2. The composition of embodiment 1, wherein the liposome further comprises cholesterol.
3. The composition of embodiment 2, wherein the cholesterol is present in the amount of up to 25 mol %.
4. The composition of any one of embodiments 1-3, wherein the at least one endogenous phosphorylated carbohydrate is a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof.

5. The composition of any one of embodiments 1-4, wherein the at least one endogenous phosphorylated carbohydrate is a phosphorylated mannose.
6. The composition of embodiment 5, wherein the phosphorylated mannose is mannose-1-phosphate.
7. The composition of any one of embodiments 1-6, wherein the endogenous phosphorylated carbohydrate is present at a concentration of about 0.1-75 mM.
8. The composition of any one of embodiments 1-7, wherein DOPE is present at a concentration of up to 80 mol %.
9. The composition of any one of embodiments 1-8, wherein the one or more stabilizers comprise 1,2-dioleoyl-sn-glycero-3-phosphocholine (DOPC).
10. The composition of any one of embodiments 1-8, wherein the one or more stabilizers comprise 1,2-dipalmitoyl-phosphatidyl-glycerole (DPPG).
11. The composition of any one of embodiments 1-8, wherein the one or more stabilizers comprise 1,2-dioleoyl-sn-glycero-3-phosphoglycerol (DOPG).
12. The composition of any one of embodiments 1-8, wherein the one or more stabilizers comprise 1,2-distearoyl-sn-glycero-3-phosphate (DSPA).
13. The composition of any one of embodiments 1-8, wherein the one or more stabilizers comprise 1,2-dioleoyl-sn-glycero-3-phospho-L-serine (DOPS).
14. The composition of any one of embodiments 1-13, wherein the one or more stabilizers are present in the amount of up to 70 mol %.
15. The composition of any one of embodiments 1-14, wherein the at least one phospholipid conjugated to PEG is 1,2-distearoyl-sn-glycero-3-phosphoethanolamine (DSPE).
16. The composition of embodiment 15, wherein PEG-DSPE is present at a concentration of up to 5 mol %.
17. A composition comprising:
 a liposome comprising:
  i) N-dodecanoyl-1,2-di-(9Z-octadecenoyl)-sn-glycero-3-phosphoethanolamine (N-C12-DOPE);
  ii) 1,2-dioleoyl-sn-glycero-3-phosphocholine (DOPC); and
 at least one phosphorylated endogenous carbohydrate, wherein the at least one endogenous carbohydrate is encapsulated in the liposome.
18. The composition of embodiment 17, wherein the at least one endogenous phosphorylated carbohydrate is a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof.
19. The composition of embodiment 17 or embodiment 18, wherein the at least one endogenous phosphorylated carbohydrate is a phosphorylated mannose.
20. The composition of embodiment 19, wherein the phosphorylated mannose is mannose-1-phosphate.
21. The composition of any one of embodiments 17-20, wherein the endogenous phosphorylated carbohydrate is present at a concentration of about 0.1-75 mM.
22. The composition of any one of embodiments 17-21, wherein N-C12-DOPE is present in the amount of up to 80 mol %.
23. The composition of any one of embodiments 17-22, wherein DOPC is present in the amount of up to 30 mol %.
24. The composition of any one of embodiments 17-23, wherein the liposome further comprises PEG conjugated to at least one phospholipid.
25. The composition of embodiment 24, wherein the at least one phospholipid conjugated to PEG is 1,2-distearoyl-sn-glycero-3-phosphoethanolamine (DSPE).
26. The composition of embodiment 25, wherein PEG-DSPE is present at a concentration of up to 5 mol %.
27. The composition of any one of embodiments 17-26, wherein the liposome further comprises cholesterol.
28. The composition of embodiment 27, wherein the cholesterol is present in the amount of up to 25 mol %.
29. A composition comprising:
 a liposome comprising:
  i) at least one phospholipid having an ethanolamine head group and an unsaturated fatty acid tail, wherein the unsaturated fatty acid tail comprises at least one $C_{10-28}$ carbon chain;
  ii) one or more of (a) to (c):
   a) at least one phospholipid having a polar head group and a saturated fatty acid tail,
   b) at least one phospholipid having a polar head group and an unsaturated fatty acid tail, wherein the polar head group comprises a quaternary ammonium cation, a glycerol group, or a serine group, and
   c) at least one acidic cholesterol ester; and
  iii) polyethylene glycol (PEG), wherein the PEG is conjugated to at least one phospholipid; and
 at least one phosphorylated endogenous carbohydrate, wherein the at least one endogenous carbohydrate is encapsulated in the liposome.
30. The composition of embodiment 29, wherein the unsaturated fatty acid tail of the at least one phospholipid in i) comprises at least one double bond.
31. The composition of embodiment 29 or embodiment 30, wherein the unsaturated fatty acid tail of the at least one phospholipid in i) comprises one double bond.
32. The composition of any one of embodiments 29-31, wherein the unsaturated fatty acid tail comprises at least one C16-20 carbon chain.
33. The composition of any one of embodiments 29-32, wherein the phospholipid having an ethanolamine head group and a fatty acid tail is 1,2-dioleoyl-sn-glycero-3-phosphoethanolamine (DOPE).
34. The composition of any one of embodiments 29-33, wherein the saturated fatty acid tail of the at least one phospholipid in a) comprises at least C16-20 carbon chain.
35. The composition of any one of embodiments 29-34, wherein the at least one phospholipid having a polar head group and a saturated fatty acid tail is 1,2-dipalmitoyl-sn-glycero-3-phosphorylglycerol (DPPG) or 1,2-distearoyl-sn-glycero-3-phosphate (DSPA), or both.
36. The composition of any one of embodiments 29-35, wherein the polar head group of the at least one phospholipid in b) is choline.
37. The composition of any one of embodiments 29-36, wherein the at least one phospholipid having a polar head group with a quaternary ammonium cation and an unsaturated fatty acid tail is 1,2-dioleoyl-sn-glycero-3-phosphocholine (DOPC).
38. The composition of any one of embodiments 29-35, wherein the polar head group of the at least one phospholipid in b) is serine.

39. The composition of embodiment 38, wherein the at least one phospholipid having a polar head group with a serine group and an unsaturated fatty acid tail is 1,2-dioleoyl-sn-glycero-3-phospho-L-serine (DOPS).

40. The composition of any one of embodiments 29-35, wherein the polar head group of the at least one phospholipid in b) is glycerol.

41. The composition of embodiment 40, wherein the at least one phospholipid having a polar head group with a glycerol group and an unsaturated fatty acid tail is 1,2-dioleoyl-sn-glycero-3-phosphoglycerol (DOPG).

42. The composition of any one of embodiments 29-41, wherein the at least one acidic cholesterol ester is cholesteryl hemisuccinate (CHEMS).

43. The composition of any one of embodiments 29-42, wherein the at least one phospholipid conjugated to PEG is 1,2-distearoyl-sn-glycero-3-phosphoethanolamine (DSPE).

44. The composition of any one of embodiments 29-43, wherein the at least one phospholipid having an ethanolamine head group and an unsaturated fatty acid tail is present at a concentration of up to 50 mol %.

45. The composition of any one of embodiments 29-44, wherein the one or more of (a) to (c) is present at a concentration of up to 70 mol %.

46. The composition of any one of embodiments 29-45, wherein the PEG conjugated to at least one phospholipid is present at a concentration of up to 5 mol %.

47. The composition of any one of embodiments 29-45, wherein the PEG conjugated to at least one phospholipid is present at a concentration of up to 3 mol %.

48. The composition of any one of embodiments 29-47, wherein the at least one endogenous phosphorylated carbohydrate is a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof.

49. The composition of embodiments 29-48, wherein the at least one endogenous phosphorylated carbohydrate is a phosphorylated mannose.

50. The composition of embodiment 49, wherein the phosphorylated mannose is mannose-1-phosphate.

51. The composition of any one of embodiments 29-50, wherein the endogenous phosphorylated carbohydrate is present at a concentration of about 0.1-75 mM.

52. The composition of any one of embodiments 29-51, wherein the liposome further comprises cholesterol.

53. The composition of embodiment 52, wherein the cholesterol is present in the amount of up to 25 mol %.

54. A composition comprising:
 a liposome comprising:
  i) a phospholipid of formula (PL-1):

(PL-1)

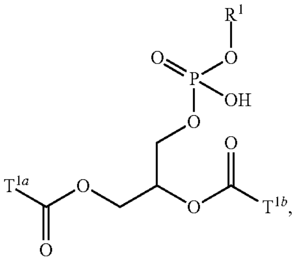

or a salt thereof, wherein:
 at least one of $T^{1a}$ and $T^{1b}$ is an unsaturated carbon chain comprising a $C_{10-28}$ alkenyl or a $C_{10-28}$ alkynyl; and
 $R^1$ is aminoalkyl;
 ii) at least one phospholipid of formula (PL-2), at least one phospholipid of formula (PL-3), or at least one cholesterol ester of formula (CE), or any combination of the foregoing:

(PL-2)

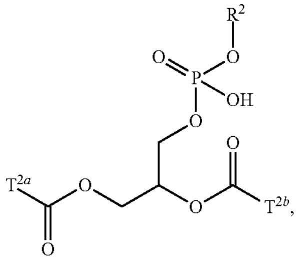

or a salt thereof, wherein:
 each of $T^{2a}$ and $T^{2b}$ is an unsaturated carbon chain comprising a $C_{10-28}$ alkenyl or a $C_{10-28}$ alkynyl; and
 $R^2$ is alkyl substituted with a quaternary ammonium, glycerol, or alkyl substituted with —COOH and —$NH_2$;

(PL-3)

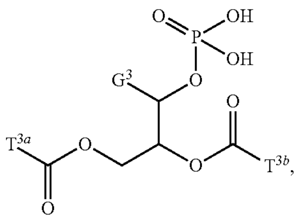

or a salt thereof, wherein:
 each of $T^{3a}$ and $T^{3b}$ is a saturated carbon chain; and
 $G^3$ is H or alkyl substituted with at least one —OH; and (CE)

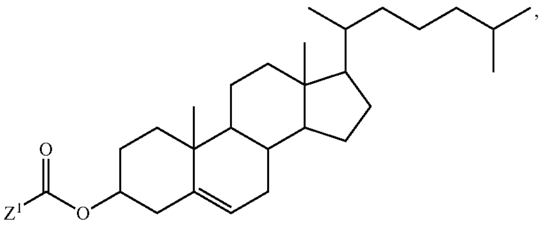

or a salt thereof, wherein:
 $Z^1$ is alkyl substituted with —COOH; and
 iii) polyethylene glycol (PEG), wherein the PEG is conjugated to at least one phospholipid; and
at least one phosphorylated endogenous carbohydrate, wherein the at least one endogenous carbohydrate is encapsulated in the liposome.

55. The composition of embodiment 54, wherein each of $T^{1a}$, $T^{1b}$, $T^{2a}$ and $T^{2b}$ is independently an unsaturated carbon chain a comprising one double bond.
56. The composition of embodiment 55, wherein the unsaturated carbon chain is a cis-isomer.
57. The composition of any one of embodiments 54-56, wherein each carbon chain has 10-28 carbon atoms.
58. The composition of embodiment 54, wherein the at least one phospholipid of formula (PL-1) is DOPE.
59. The composition of embodiment 54 or embodiment 58, wherein the at least one phospholipid of formula (PL-2) is DOPC or DOPS.
60. The composition of embodiment 54, 58, or 59, wherein at least one phospholipid of formula (PL-3) is DPPG, DOPG, or DSPA.
61. The composition of any one of embodiments 54-60, wherein the at least one cholesterol ester of formula (CE) is CHEMS.
62. The composition of any one of embodiments 51-61, wherein the liposome further comprises cholesterol.
63. The composition of embodiment 62, wherein the cholesterol is present in the amount of up to 25 mol %.
64. The composition of any one of embodiments 51-63, wherein the at least one phospholipid conjugated to PEG is 1,2-distearoyl-sn-glycero-3-phosphoethanolamine (DSPE).
65. The composition of embodiment 64, wherein PEG-DSPE is present at a concentration of up to 5 mol %.
66. A composition comprising:
a liposome comprising a phospholipid of formula (PL-4):

(PL-4)

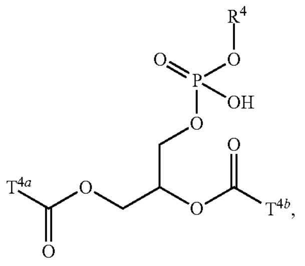

or a salt thereof, wherein:
at least one of $T^{1a}$ and $T^{1b}$ is an unsaturated carbon chain comprising a $C_{10-28}$ alkenyl or a $C_{10-28}$ alkynyl; and
$R^4$ is an aliphatic chain comprising an amide moiety; and
at least one phosphorylated endogenous carbohydrate, wherein the at least one endogenous carbohydrate is encapsulated in the liposome.
67. The composition of embodiment 66, wherein PL-4 is N-dodecanoyl-1,2-di-(9Z-octadecenoyl)-sn-glycero-3-phosphoethanolamine (N-C12-DOPE).
68. The composition of embodiment 66 or embodiment 67, wherein the at least one endogenous phosphorylated carbohydrate is a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof.
69. The composition of embodiment 66, wherein the at least one endogenous phosphorylated carbohydrate is a phosphorylated mannose.
70. The composition of embodiment 69, wherein the phosphorylated mannose is mannose-1-phosphate.
71. The composition of any one of embodiments 66-70, wherein the endogenous phosphorylated carbohydrate is present at a concentration of about 0.1-75 mM.
72. A pharmaceutical composition comprising the composition of any one of the preceding embodiments, and a pharmaceutically acceptable carrier.
73. A method for delivering a carbohydrate to a human in need thereof, comprising administering to the human the composition of any one of the preceding embodiments.
74. A method for delivering a carbohydrate to a cell interior of a subject in need thereof, comprising administering to the subject a composition of any one of embodiments 1 to 71, or a pharmaceutical composition of embodiment 72, wherein at least a portion of the administered composition traverses the cell plasma membrane to deliver the carbohydrate to the cell interior.
75. A method for treating a congenital disorder of glycosylation (CDG) in a human in need thereof, comprising administering to the human a composition of any one of embodiments 1 to 71, or a pharmaceutical composition of embodiment 72.
76. The method of embodiment 75, wherein the congenital disorder of glycosylation (CDG) is a CDG-Ia disorder.
77. The method of embodiment 76, wherein the administration of the composition induces a 0.05-fold to at least a 3-fold increase in cellular production of higher-order lipid-linked oligosaccharides in the human, as compared to cellular production of higher-order lipid-linked oligosaccharides in the human in the absence of administering the composition to the human.
78. A kit comprising: a composition of any one of embodiments 1 to 71 or the pharmaceutical composition of embodiment 72.
79. The kit of embodiment 78, further comprising a container and a label or package insert(s) on or associated with the container.
80. A composition comprising:
a liposome comprising:
i) 1,2-dioleoyl-sn-glycero-3-phosphoethanolamine or a salt thereof; and
ii) (a) one or more phospholipid having a polar head group, wherein the polar head group comprises glycerol, choline, phosphate and serine and a fatty acid tail comprising a $C_{10-28}$ aliphatic chain, or (b) an acidic cholesterol ester, or both (a) and (b); and
iii) polyethylene glycol (PEG) conjugated to at least one phospholipid; and
at least one endogenous carbohydrate encapsulated in the liposome.
81. The composition of embodiment 80, wherein the one or more phospholipid having a polar head group comprise:
1,2-dioleoyl-sn-glycero-3-phosphocholine;
1,2-dipalmitoyl-phosphatidyl-glycerole;
1,2-dioleoyl-sn-glycero-3-phosphoglycerol;
1,2-distearoyl-sn-glycero-3-phosphate; or
1,2-dioleoyl-sn-glycero-3-phospho-L-serine,
or a salt thereof, or any combination of the foregoing.

82. The composition of embodiment 81, wherein the one or more phospholipid having a polar head group comprise 1,2-dioleoyl-sn-glycero-3-phosphocholine or a salt thereof 83. A composition comprising:
 a liposome comprising:
  i) N-dodecanoyl-1,2-di-(9Z-octadecenoyl)-sn-glycero-3-phosphoethanolamine or a salt thereof; and
  ii) 1,2-dioleoyl-sn-glycero-3-phosphocholine or a salt thereof; and
 at least one endogenous carbohydrate encapsulated in the liposome.

84. The composition of embodiment 83, wherein the liposome further comprises PEG conjugated to at least one phospholipid.

85. A composition comprising:
 a liposome comprising:
  i) at least one phospholipid having an ethanolamine head group and at least one unsaturated fatty acid tail, wherein each unsaturated fatty acid tail independently comprises at least one $C_{10-28}$ carbon chain;
  ii) one or more of (a) to (c):
   a) at least one phospholipid having a polar head group and at least one saturated fatty acid tail,
   b) at least one phospholipid having a polar head group and at least one unsaturated fatty acid tail, wherein the polar head group comprises a quaternary ammonium cation, a glycerol group, or a serine group, and
   c) at least one acidic cholesterol ester; and
  iii) polyethylene glycol (PEG), wherein the PEG is conjugated to at least one phospholipid; and
 at least one endogenous carbohydrate encapsulated in the liposome.

86. The composition of embodiment 85, wherein each unsaturated fatty acid tail of the at least one phospholipid in i) comprises at least one double bond.

87. The composition of embodiment 85 or 86, wherein each unsaturated fatty acid tail of the at least one phospholipid in i) comprises one double bond.

88. The composition of any one of embodiments 85 to 87, wherein the unsaturated fatty acid tail comprises at least one $C_{16-20}$ carbon chain.

89. The composition of any one of embodiments 85 to 88, wherein the phospholipid having an ethanolamine head group and at least one unsaturated fatty acid tail is 1,2-dioleoyl-sn-glycero-3-phosphoethanolamine or a salt thereof.

90. The composition of any one of embodiments 85 to 89, wherein the saturated fatty acid tail of the at least one phospholipid in a) comprises at least $C_{16-20}$ carbon chain.

91. The composition of any one of embodiments 85 to 90, wherein the at least one phospholipid having a polar head group and a saturated fatty acid tail is 1,2-dipalmitoyl-sn-glycero-3-phosphorylglycerol or 1,2-distearoyl-sn-glycero-3-phosphate, or a salt there of, or a combination of the foregoing.

92. The composition of any one of embodiments 85 to 91, wherein the polar head group of the at least one phospholipid in b) is choline.

93. The composition of embodiment 92, wherein the at least one phospholipid having a polar head group with a quaternary ammonium cation and an unsaturated fatty acid tail is 1,2-dioleoyl-sn-glycero-3-phosphocholine or a salt thereof.

94. The composition of any one of embodiments 85 to 91, wherein the polar head group of the at least one phospholipid in b) is serine.

95. The composition of embodiment 94, wherein the at least one phospholipid having a polar head group with a serine group and an unsaturated fatty acid tail is 1,2-dioleoyl-sn-glycero-3-phospho-L-serine or a salt thereof.

96. The composition of any one of embodiments 85 to 91, wherein the polar head group of the at least one phospholipid in b) is glycerol.

97. The composition of embodiment 96, wherein the at least one phospholipid having a polar head group with a glycerol group and an unsaturated fatty acid tail is 1,2-dioleoyl-sn-glycero-3-phosphoglycerol or salt thereof 98. The composition of any one of embodiments 85 to 97, wherein the at least one acidic cholesterol ester is cholesteryl hemisuccinate.

99. The composition of any one of embodiments 80 to 82 or 84 to 98, wherein the at least one phospholipid conjugated to PEG is 1,2-distearoyl-sn-glycero-3-phosphoethanolamine or a salt thereof.

100. A composition comprising:
 a liposome comprising:
  i) a phospholipid of formula (PL-1):

(PL-1)

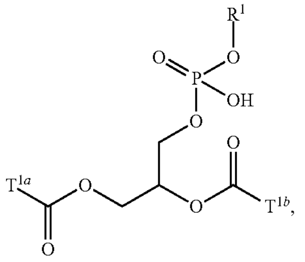

or a salt thereof, wherein:
   at least one of $T^{1a}$ and $T^{1b}$ is an unsaturated carbon chain comprising a $C_{10-28}$ alkenyl or a $C_{10-28}$ alkynyl; and
   $R^1$ is aminoalkyl;
  ii) at least one phospholipid of formula (PL-2), at least one phospholipid of formula (PL-3A), or at least one cholesterol ester of formula (CE), or any combination of the foregoing:

(PL-2)

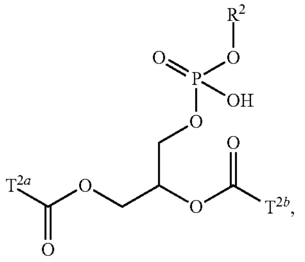

or a salt thereof, wherein:

each of $T^{2a}$ and $T^{2b}$ is an unsaturated carbon chain comprising a $C_{10\text{-}28}$ alkenyl or a $C_{10\text{-}28}$ alkynyl; and $R^2$ is alkyl substituted with a quaternary ammonium, glycerol, or alkyl substituted with —COOH and —$NH_2$;

(PL-3A)

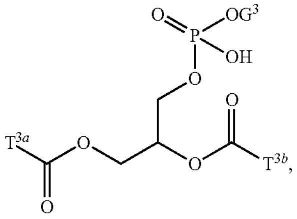

or a salt thereof, wherein:

each of $T^{3a}$ and $T^{3b}$ is a carbon chain; and $G^3$ is H or alkyl substituted with at least one —OH; and (CE)

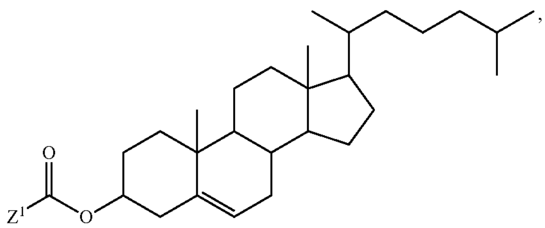

or a salt thereof, wherein:

$Z^1$ is alkyl substituted with —COOH; and iii) polyethylene glycol (PEG), wherein the PEG is conjugated to at least one phospholipid; and at least one endogenous carbohydrate encapsulated in the liposome.

101. The composition of embodiment 100, wherein each of $T^{1a}$, $T^{1b}$, $T^{2a}$ and $T^{2b}$ is independently an unsaturated carbon chain a comprising one double bond.

102. The composition of embodiment 101, wherein the unsaturated carbon chain is a cis-isomer.

103. The composition of any one of embodiments 100 to 102, wherein each carbon chain has 10-28 carbon atoms.

104. The composition of embodiment 103, wherein the at least one phospholipid of formula (PL-1) is

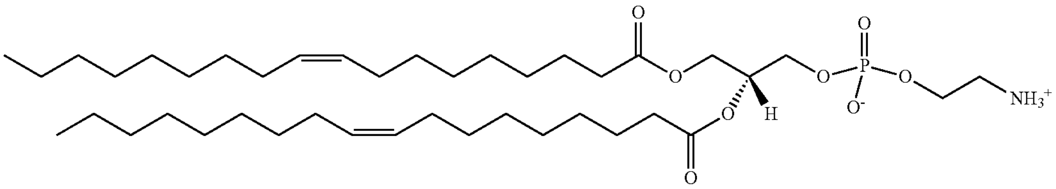 [SMILES: CCCCCCCC/C=C\CCCCCCCC(=O)OC[C@H](COP(=O)([O-])OCC[NH3+])OC(=O)CCCCCCC/C=C\CCCCCCCC]

or a salt thereof.

105. The composition of any one of embodiments 100 to 104, wherein the at least one phospholipid of formula (PL-2) is

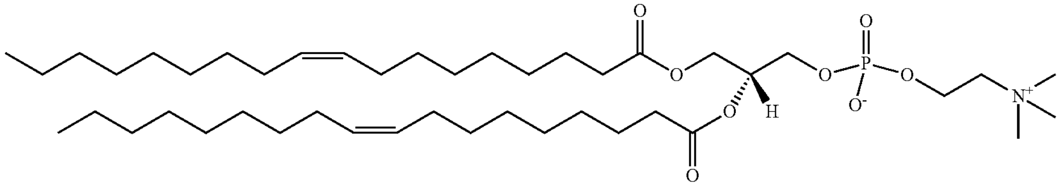

or

-continued

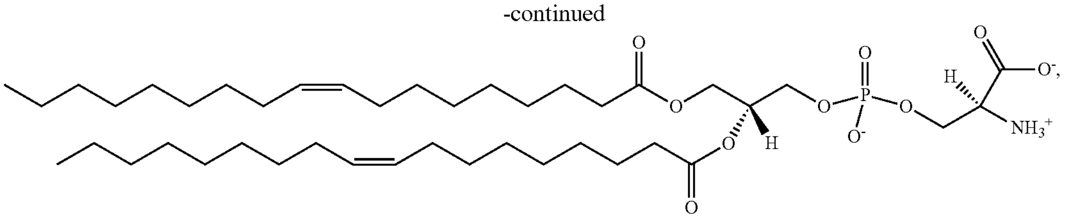

or a salt thereof.

106. The composition of any one of embodiments 100 to 105, wherein at least one phospholipid of formula (PL-3A) is

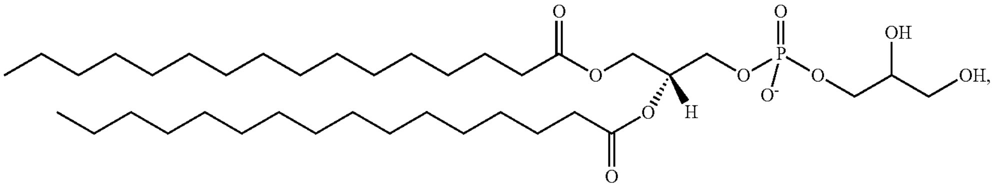

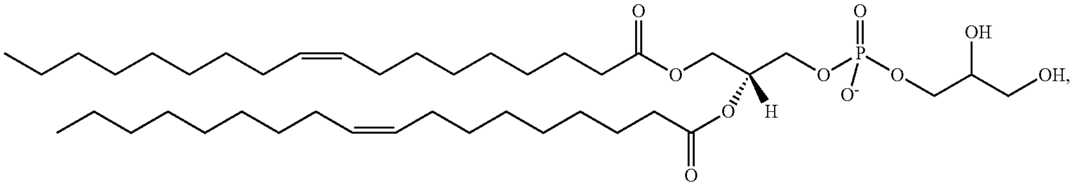

or

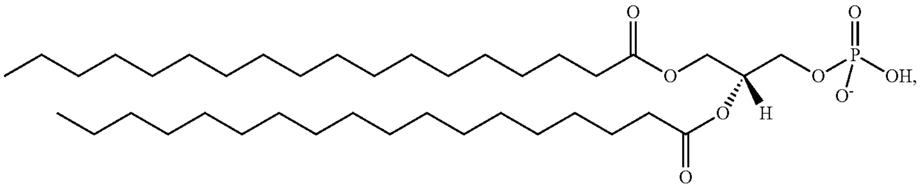

or a salt thereof.

107. The composition of any one of embodiments 100 to 106, wherein the at least one cholesterol ester of formula (CE) is

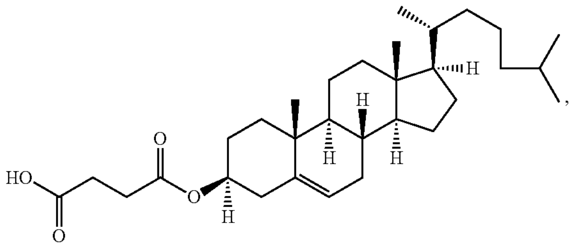

or a salt thereof.

108. The composition of any one of embodiments 80 to 82 and 84 to 107, wherein the at least one phospholipid conjugated to PEG is

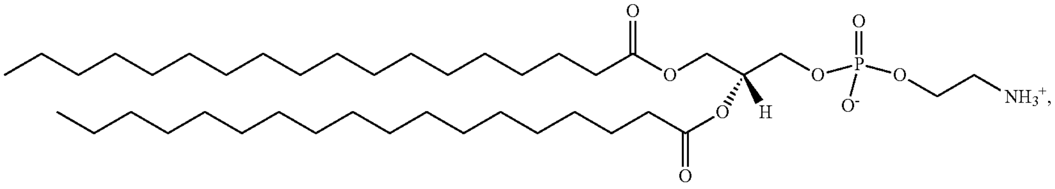

or a salt thereof.

109. A composition comprising:

a liposome comprising a phospholipid of formula (PL-4):

(PL-4)

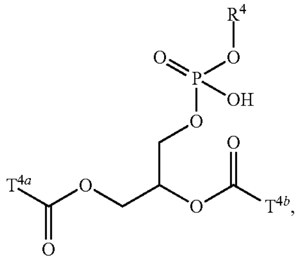

or a salt thereof, wherein:

at least one of $T^{1a}$ and $T^{1b}$ is an unsaturated carbon chain comprising a $C_{10-28}$ alkenyl or a $C_{10-28}$ alkynyl; and $R^4$ is an aliphatic chain comprising an amide moiety; and at least one endogenous carbohydrate encapsulated in the liposome.

110. The composition of embodiment 109, wherein PL-4 is

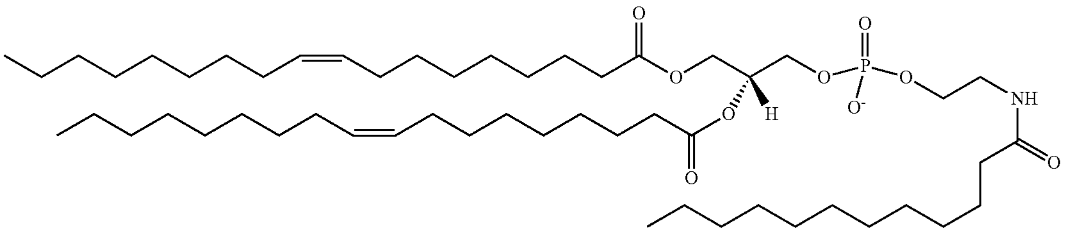 [SMILES: CCCCCCCC/C=C\CCCCCCCC(=O)OC[C@H](COP(=O)([O-])OCCNC(=O)CCCCCCCCCCC)OC(=O)CCCCCCC/C=C\CCCCCCCC]

or a salt thereof.

111. The composition of any one of embodiments 80 to 110, wherein the at least one endogenous carbohydrate is:

(i) a endogenous phosphorylated carbohydrate; or (ii) a phosphorylated monosaccharide, a phosphorylated disaccharide, a phosphorylated oligosaccharide, a phosphorylated polysaccharide, a phosphorylated mannose, a phosphorylated mannofuranose, a phosphorylated mannopyranos, or a nucleotide sugar, or any combination thereof.

112. The composition of embodiment 111, wherein the phosphorylated mannose is mannose-1-phosphate.

113. A pharmaceutical composition comprising the composition of any one of the preceding embodiments, and a pharmaceutically acceptable carrier.

114. A method for delivering a carbohydrate to a human in need thereof, comprising administering to the human the composition of any one of the preceding embodiments.

115. A method for delivering a carbohydrate to a cell interior of a subject in need thereof, comprising administering to the subject a composition of any one of embodiments 1 to 113, wherein at least a portion of the administered composition traverses the cell plasma membrane to deliver the carbohydrate to the cell interior.

116. A method for treating a congenital disorder of glycosylation (CDG) in a human in need thereof, comprising administering to the human a composition of any one of embodiments 1 to 113.

117. The method of embodiment 116, wherein the congenital disorder of glycosylation (CDG) is a CDG-Ia disorder.

118. The method of embodiment 116 or 117, wherein the administration of the composition induces a 0.05-fold to at least a 3-fold increase in cellular production of higher-order lipid-linked oligosaccharides in the human, as compared to cellular production of higher-order lipid-linked oligosaccharides in the human in the absence of administering the composition to the human.

119. A kit comprising:

a composition of any one of embodiments 1 to 113;

a container; and a label or package insert on or associated with the container.

EXAMPLES

The following Examples are merely illustrative and is not meant to limit any aspects of the present disclosure in any way.

Liposomes

Materials for liposome preparation were purchased from Avanti Polar Lipids, NOF America Corporation, FormuMax Scientific, Inc., CordenPharma, and Lipoid. The following lipids were purchased from Avanti: DOPE, DOPC, DPPG, DOPG, DOPS, N-C12-DOPE, Chol, CHEMS, and DSPE-PEG-Gal. The following lipids were purchased from NOF America Corporation: DSPA, DMG-PEG, ssPalmm, ssPalme, SOPC, and PEG(2k)-DSG. The following lipids were purchased from FormuMax Scientific, Inc.: RH-DHPE, DODAP, and DOTAP. The following lipids were purchased from CordenPharma: Dlink-KC2-DMA.

Lipid raw materials were dissolved in chloroform and warmed up for complete dissolution. The mixture was then dried to form a thin-film. The film was then hydrated with an aqueous solution that contains the phosphorylated carbohydrate. The solution was heated and mixed well to re-suspend the thin-film. The suspension was subject to three freeze-thaw cycles. Finally the sizes of the liposomes were adjusted either by sonication, extrusion, or microfluidization.

Cell Lines

CDG-Ia human dermal fibroblasts and wild-type human dermal fibroblasts were purchased from Coriell Institute.

Culture Media

RPMI media was mixed with FBS (10% v/v), Pen-Strep (1% v/v), and L-glutamine (1% v/v) to make a complete RPMI media. This media was used for the expansion of the fibroblasts. All of them were purchased from Thermo Fisher Scientific.

Example 1

Screening and Selection of Lipids for Intracellular Delivery of M1P

In order to select the appropriate combination of lipids for intracellular delivery of M1P, different Lipo-M1P formulations were evaluated for their ability to penetrate cellular membranes, as well as, to promote endosomal escape and release of the M1P active ingredient into the cytosol. A functional cell-based assay measuring GDP-Mannose levels before and after treatment with Lipo-M1P was used as measure of delivery and bioactivity of various liposomal compositions. A total of 34 different Lipo-M1P formulations were prepared using a bench scale thin-film hydration method. Cells were treated with the different Lipo-M1P formulations at a total lipid concentrations of up to 5.4 mM. Cell viability was determined using XTT cell proliferation assay (Thermo Fisher Scientific) and 28 out of 33 formulations tested maintained cell viability above the desired 80%. After treatment, cells were harvested, GDP-Mannose was extracted, and analyzed by liquid chromatography mass spectrometry (LC-MS). Results are summarized in Table 1.

TABLE 1

Liposomal formulations of M1P and their effect on synthesis of GDP-Mannose and cell viability

| ID | Liposome Composition | Lipid Ratio, mol % | Total Lipid, mM | Lipo-M1P, mM | GDP-Man, % | Cell Viability % |
|---|---|---|---|---|---|---|
| 1 | DSPC/DSPE-PEG/RH-DHPE | 95:5:0.25 | 5.4 | 0.77 | 35 | 59 |
| 2 | DSPC/DSPE-PEG/RH-DHPE/Chol | 74:5:0.25:21 | 5.4 | 0.66 | 24 | 99 |
| 3 | DSPC/DODAP/DSPE-PEG/Chol | 25:25:5:45 | 1.2 | 0.15 | 34 | 99 |
| 4 | DSPC/DMG-PEG/Dlin-KC2-DMA/Chol | 10:10:40:40 | 1.2 | 0.09 | 17 | 59* |
| 5 | ssPalmm/SOPC/PEG(2k)-DSG/Chol | 29.1:38.8:3:29.1 | 5.4 | 0.44 | 51 | 132 |
| 6 | ssPalme/SOPC/PEG(2k)-DSG/Chol | 29.1:38.8:3:29.1 | 4.0 | 0.15 | 35 | NP |
| 7 | DSPA/DOPC/DSPE-PEG/Chol | 11.9:35.6:5:47.5 | 1.2 | 0.24 | 33 | 104 |
| 8 | N-C12-DOPE/DOPC | 71.8:28.2 | 4.0 | 0.67 | 220 | 105 |
| 9 | N-C12-DOPE/DOPC/DSPE-PEG | 77.6:19.4:3 | 4.0 | 0.52 | 131 | 102 |
| 10 | N-C12-DOPE/DOPC/DSPE-PEG | 69.6:27.4:3 | 5.4 | 0.80 | 201 | 88 |
| 11 | N-C12-DOPE/DOPC/DSPE-PEG | 68.6:26.4:5 | 5.4 | 0.78 | 270 | 84 |
| 12 | N-C12-DOPE/DOPC/DSPE-PEG/Chol | 66:26:3:5 | 5.4 | 0.47 | 272 | 103 |
| 13 | N-C12-DOPE/DPPE/DOPC/DSPE-PEG | 69.6:13.7:13.7:3 | 4.0 | 0.58 | 163 | 98 |
| 14 | N-C12-DOPE/DOPE/DOPC/DSPE-PEG | 69.6:13.7:13.7:3 | 4.0 | 0.41 | 120 | 100 |
| 15 | DOPE/DOPG/DSPE-PEG | 38.8:58.2:3 | 4.0 | 0.40 | 160 | 112 |
| 16 | DOPE/DOPG/DSPE-PEG | 58.2:38.8:3 | 5.4 | 0.81 | 191 | 111 |
| 17 | DOPE/DSPA/DSPE-PEG | 75.4:21.6:3 | 5.4 | 0.58 | 115 | 106 |
| 18 | DOPE/DC-Chol/DSPE-PEG | 48.5:48.5:3 | 0.022 | 0.0039 | 45 | 19** |
| 19 | DOPE/DOPC/DSPE-PEG | 38.8:58.2:3 | 4.0 | 0.55 | 174 | 131 |
| 20 | DOPE/DOPC/DSPE-PEG | 48.5:48.5:3 | 5.4 | 0.63 | 261 | 126 |
| 21 | DOPE/DOPC/DSPE-PEG | 58.2:38.8:3 | 5.4 | 0.72 | 222 | 94 |
| 22 | DOPE/DOPC/DSPE-PEG | 30:67:3 | 1.23 | 0.7 | 365 | 90 |
| 23 | DOPE/DOPC/DSPE-PEG | 40:57:3 | 0.98 | 0.7 | 311 | 93 |
| 24 | DOPE/DPPG/DOPC/DSPE-PEG | 40:10:47:3 | 0.93 | 0.7 | 413 | 98 |
| 25 | DOPE/DOPC/DSPE-PEG/Chol | 46:46:3:5 | 5.4 | 0.79 | 145 | 115 |
| 26 | DOPE/DOPS/DSPE-PEG | 58.2:38.8:3 | 5.4 | 0.72 | 592 | 66 |
| 27 | DOPE/CHEMS | 60:40 | 1.2 | 0.18 | 305 | 84 |
| 28 | DOPE/CHEMS/DSPE-PEG | 57:38:5 | 1.2 | 0.14 | 182 | 95 |
| 29 | DOPE/CHEMS/DSPE-PEG | 58.2:38.8:3 | 3.1 | 0.45 | 134 | 78 |
| 30 | DOPE/CHEMS/DSPE-PEG | 77.6:19.4:3 | 1.2 | 0.18 | 36 | 134 |
| 31 | DOPE/CHEMS/DSPE-PEG/Chol | 57:33:5:5 | 1.2 | 0.14 | 68 | 92 |

TABLE 1-continued

Liposomal formulations of M1P and their effect on synthesis of GDP-Mannose and cell viability

| ID | Liposome Composition | Lipid Ratio, mol % | Total Lipid, mM | Lipo-M1P, mM | GDP-Man, % | Cell Viability % |
|---|---|---|---|---|---|---|
| 32 | DOPE/CHEMS/DSPE-PEG/Chol | 58.2:19.4:3:19.4 | 1.2 | 0.07 | 22 | 107 |
| 33 | DOPE/CHEMS/DSPE-PEG/Chol | 58.2:33.8:3:5 | 5.4 | 0.61 | 269 | 104 |
| 34 | DOPE/CHEMS/DOPC/DSPE-PEG | 72.75:9.7:14.55:3 | 1.2 | 0.14 | 33 | 113 |

*Cell viability measured at total lipid concentration of 3.2 mM
**Cell viability measured at total lipid concentration of 0.1 mM
NP = not performed

Example 2

Initial Formulation Stability Studies of Lipo-M1P

In vitro evaluation of M1P leakage from the liposome was performed to characterize the physical state of the lipid bilayer and encapsulated M1P to gain an understanding of M1P stability inside the liposome under physiological conditions. After washing freshly prepared Lipo-M1P particles to remove free un-encapsulated M1P, Lipo-M1P was re-suspended in PBS pH 7.4 and stored at 37° C. The liposome composition is DOPE:DOPC:DSPE-PEG2000=48.5:48.5:3 (mol %). At several time points up to 24 hours, M1P that had leaked out of the particles was isolated using a 10 kDa molecular weight cut-off membrane (MWCO) centrifugal filter and liposomes in the filter were brought up to the original volume by adding fresh PBS. Filtrates containing the leaked M1P were quantified by bicinchoninic acid assay (BCA assay). M1P leakage was calculated as % of total Lipo-M1P and plotted over time shown in FIG. 1. A negligible amount of leakage was observed with only 2.5% released at the 24 hour time point, thus demonstrating that Lipo-M1P particles show good stability in a physiological buffer.

Figure 2A:
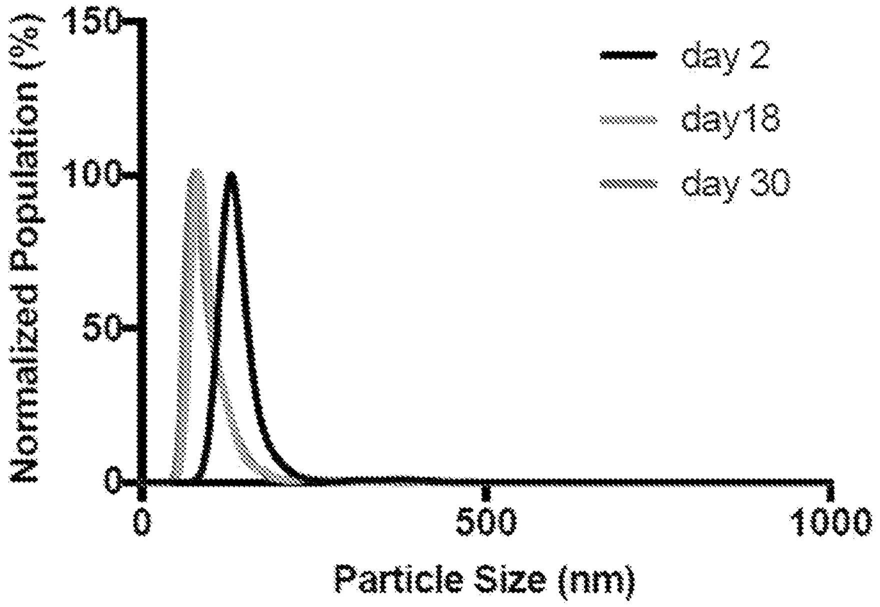
FIG. 2A depicts the aggregation profile of Lipo-M1P in phosphate buffered saline (PBS) solution pH 7.4 with size distribution in nanometer-range.
Figure 2B:
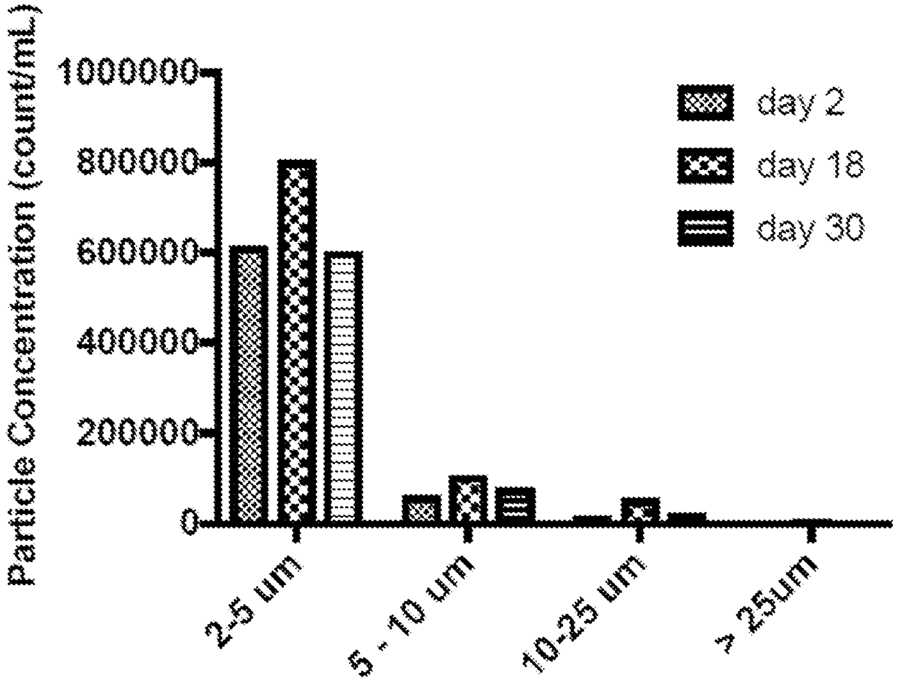
FIG. 2B depicts the concentration of micron-size particles of Lipo-M1P in PBS pH 7.4.

FIGS. 2A and 2B show the nanoparticle size distribution and concentration of micron size particles measured in Lipo-M1P in PBS pH 7.4 on day 2, 18, and 30 of storage at 4° C. The number of micron size particles in the 2 to 5 micron range measured on day 2 represents 10^-7% of the total number of both nanometer and micron size particles. No significant changes in particle size and distribution between day 2 and 30 were observed demonstrating that Lipo-M1P has a very limited tendency to aggregate during refrigerated storage. Data was collected using NanoSight and FlowCam particle imaging systems for nanometer and micron size ranges, respectively.

Further stability data was collected for aggregation of Lipo-M1P nanoparticles in 10% FBS first incubated at 37° C. for 18 h, followed by storage at 4° C. for 21 days. No shift in particle size distribution was observed between day 2 in PBS and day 21 in FBS (data not shown). A slight increase in the concentration of micron size particles was observed, however, it did not change the overall low percentage of 10^-7%.

Example 3

In Vitro Study of Lipo-M1P Bioactivity in PMM2-CDG Fibroblasts

This example explores the bioactivity of various Lipo-M1P formulations in patient-derived cultured fibroblast cells. Three Lipo-M1P formulations were used:

Formulation A: DOPE/DOPC/DSPE-PEG(2000)=58.2:38.8:3;

Formulation B: N-C12-DOPE/DOPC/DSPE-PEG(2000)=69.6:27.4:3

Formulation C: DSPC/Chol/DSPE-PEG/DOTAP/Rh-DHPE=24:45:5:25:0.5

Figure 3A:
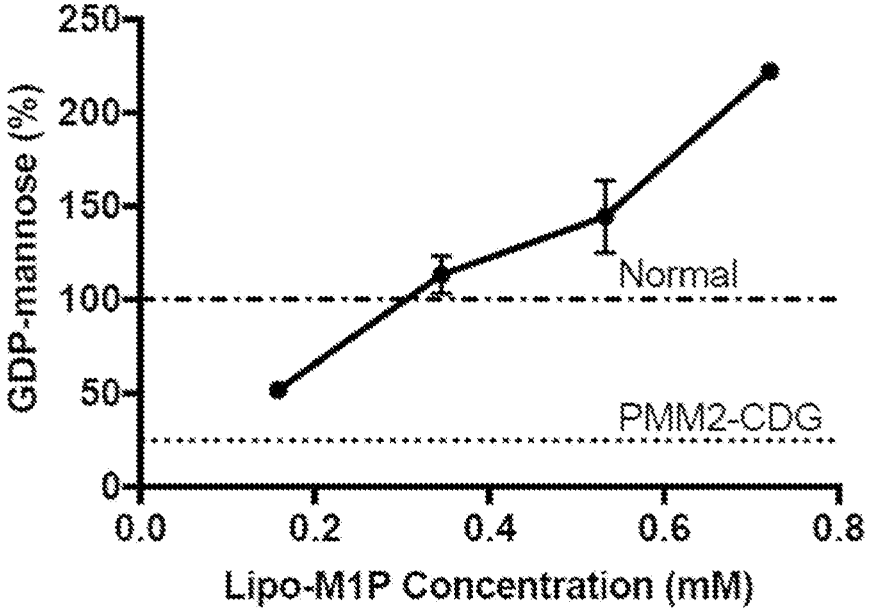
FIGS. 3A and 3B depict the bioactivity of Lipo-M1P in PMM2-CDG fibroblasts. Lipo-M1P dose response study is shown in FIG. 3A. Cell viability of Lipo-M1P at concentrations tested in the dose-response study is shown in FIG. 3B.
Figure 3B:
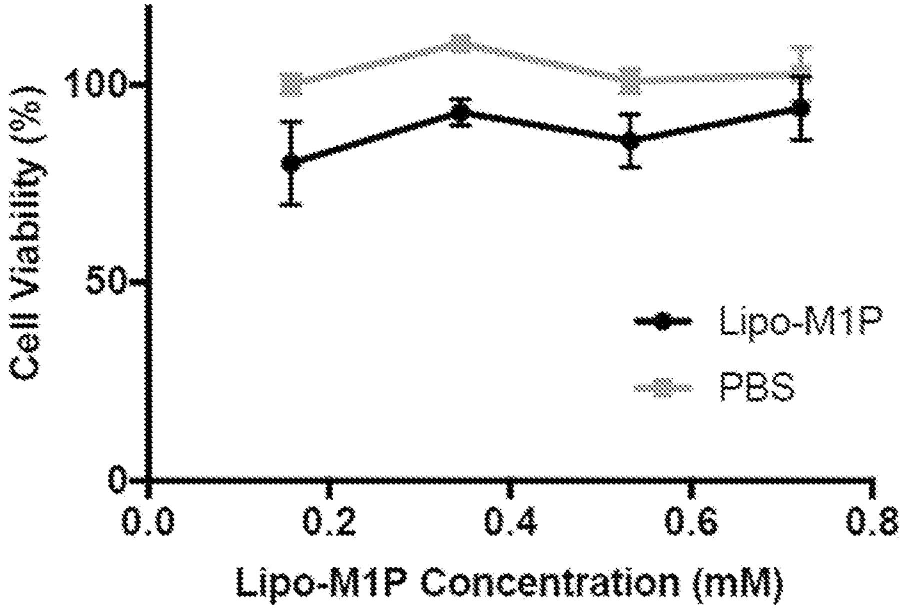

Patient-derived cultured fibroblast cells were treated at concentrations ranging from 0.15 to 0.72 mM of Formulation A for 18 hours. Mass spectrometric analysis showing GDP-Mannose increase over untreated patient and normal fibroblasts is shown in FIG. 3A. Levels of the M1P metabolite were normalized with an overnight treatment with a low dose of Lipo-M1P of roughly 0.35 mM. As expected, GDP-Mannose increased with increasing concentration of Lipo-M1P. Cell viability was maintained at nearly 100% across the Lipo-M1P concentration range explored, FIG. 3B.

Figure 4:
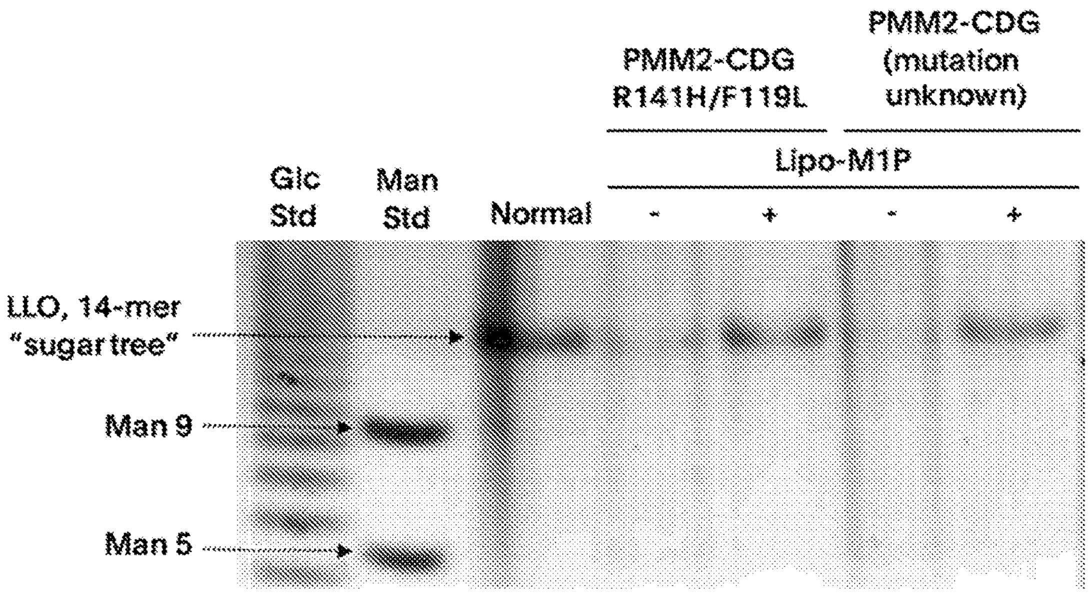
FIG. 4 depicts FACE gel of LLO in normal and PMM2-CDG fibroblasts from two patients before and after treatment with Lipo-M1P.

To determine whether decreased levels of full length mature LLO can be corrected with Formulation B, patient fibroblasts were incubated with 0.24 mM Lipo-M1P for LLO studies and a range of concentrations between 0.06 and 0.48 mM Lipo-M1P for ICAM-1. After an 18-hour treatment, cells were harvested and LLO was extracted, labeled with a fluorescence tag and examined by fluorophore-assisted carbohydrate electrophoresis (FACE). Qualitative results are presented in FIG. 4. Lipo-M1P treatment increased levels of full length LLO indicating that the delivered M1P is being metabolized to GDP-Mannose and entering the LLO biosynthesis pathway.

Figure 5:
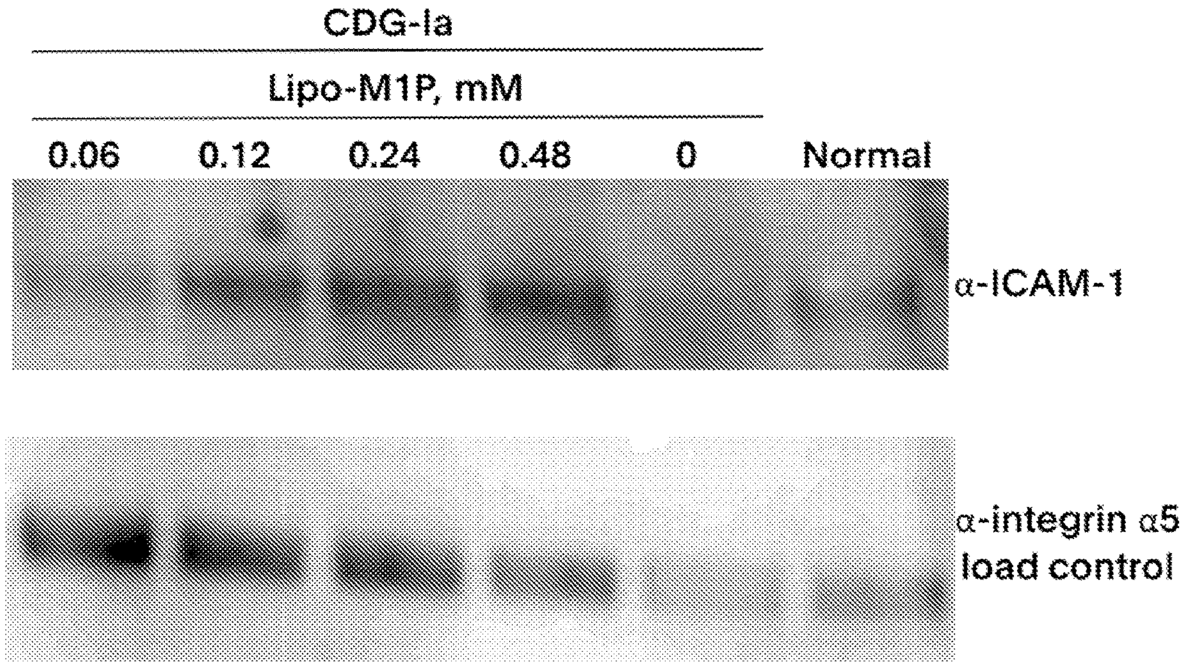
FIG. 5 depicts Western blot of ICAM-1 in normal and PMM2-CDG fibroblasts untreated and treated with different concentrations of Lipo-M1P.

To evaluate the effect of treatment on levels of the protein biomarker intercellular adhesion molecule 1 (ICAM-1), ICAM-1 was extracted using Mem-PER™ Plus membrane protein extraction kit (Thermo Fisher Scientific) and visualized by western blot using anti-ICAM-1 antibody (R&D). Results are presented in FIG. 5. The concentration dependent increase in ICAM-1 provides evidence that Formulation C restores the N-glycan biosynthetic pathway and corrects protein hypo-glycosylation in patient cells.

Example 4

Biodistribution and Pharmacokinetics of Lipo-M1P in CD-1 Mice

A study evaluating the pharmacokinetics of Lipo-M1P in female CD-1 mice was performed at Bayside Biosciences (Santa Clara, CA). Sixteen CD-1 female mice were injected via tail vain injection with Oregon Green-labeled Lipo-M1P representing a dose of 250 mg/kg lipid and 12.5 mg/kg M1P. The liposome composition is DOPE:DOPC:DSPE-PEG and the ratio of DOPE and DOPC was 1:1 (mol %). The mice were divided into four groups and at each time point one group was chosen for blood collection or blood and liver collection at various time points up to 48 hours. Concentrations of liposomes in plasma and homogenized livers were measured using fluorescence of the Oregon Green label. The pharmacokinetic characteristics of Lipo-M1P are summarized in Table 2.

TABLE 2

Pharmacokinetic profile of Lipo-M1P in mice.

| Parameter (Units) | |
|---|---|
| $C_{max}$ (mg/mL) | 4.5 |
| Elimination half-life (hours) | 4.36 |
| AUC (h * kg * mg/mL) | 1.12 |
| 1st Volume of Distribution (mL/kg) | 1754 ± 26 |
| 2nd Volume of Distribution (mL/kg) | 206 ± 98 |
| 1st Clearance (mL/(kg * h)) | 222 ± 5 |
| 2nd Clearance (mL/(kg * h)) | 226 ± 108 |

n = 4;
mean ± standard error
Population PK modeling was done with Pharsight NLME 7.0 software (Certara). The best fit was obtained with an additive 2-compartment clearance model.

Figure 6A:
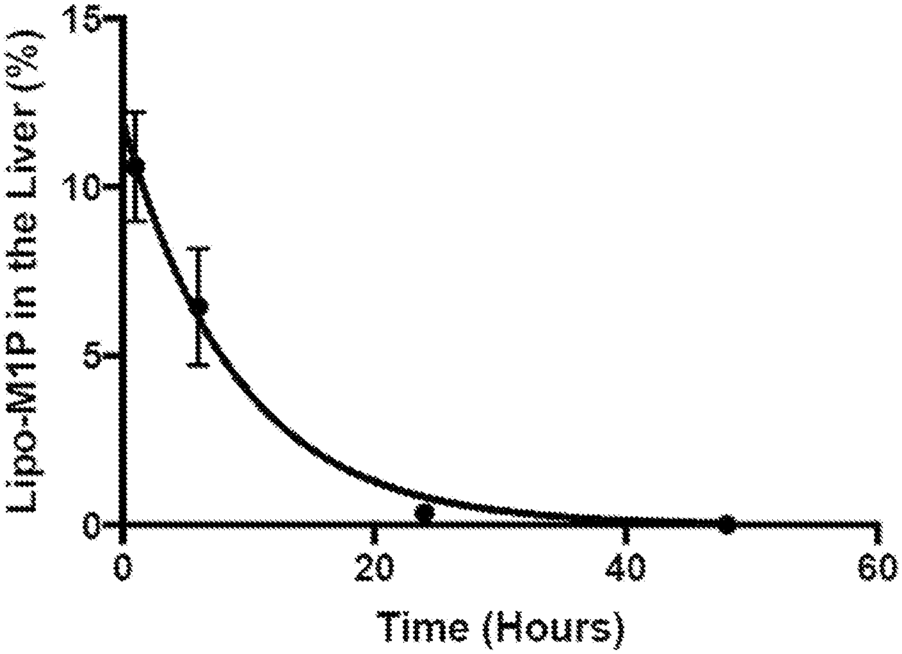
FIG. 6A depicts distribution of Lipo-M1P to the liver expressed as percentage of total dose.
Figure 6B:
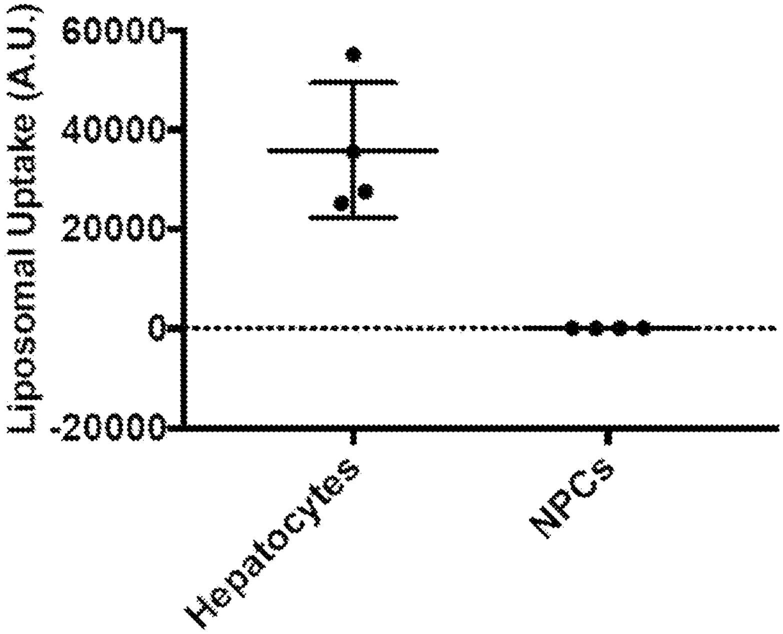
FIG. 6B depicts liposomal uptake to hepatocytes and NPCs.

In addition to plasma PK, liposome PK in the liver was evaluated and shown in FIG. 6A. The elimination half-life in the liver was 6.22 h. Intra-hepatic distribution of Lipo-M1P was evaluated and confirmed the delivery of Lipo-M1P into hepatocytes. Four CD-1 female mice were dosed with Oregon Green-labeled Lipo-M1P at 290 mg/kg lipid and 15 mg/kg M1P. Mice were sacrificed 1 hour after injection and livers were perfused and digested using liver digestion media (Thermo Fisher Scientific). Hepatocytes and non-parenchymal cells (NPCs) were isolated from the digested liver suspension using Percoll density gradient centrifugation. The fluorescence from liposomes in hepatocytes and NPCs were measured using flow cytometry. Auto-fluorescence from cells was subtracted. FIG. 6B shows that Lipo-M1P was preferentially taken up by hepatocytes while no statistically significant uptake of Lipo-M1P into NPCs was observed.

The effect of PEGylation and presence of galactose moiety on the surface of the liposome on hepatic uptake of Lipo-M1P were extensively evaluated (data not shown). There were no significant differences in hepatic uptake between 3% and 5% PEG with molecular weight of 2000 Da. Reducing PEG length to 350 Da and increasing its percentage to 7.5% resulted in 1-fold greater cellular uptake; however, it significantly decreased plasma half-life. Galactose moiety did not significantly improve the hepatocytes targeting ability of the liposomes in vitro or in vivo.

Example 5

Safety and Toxicity of Lipo-M1P in Rats

Dose escalation and repeat dose studies in Sprague Dawley rats were performed at Charles River Laboratories. Animals were approximately five weeks old at study initiation. The Lipo-M1P was administered via intravenous (slow bolus) injection into the tail vein. For the dose escalation phase, four groups of three males were administered a single dose of Lipo-M1P (DOPE/DOPC/DSPE-PEG/M1P; lipid ratio: 48.5:48.5:3). Group 1 were administered 100 mg lipid per kg weight, Group 2 were administered 250 mg/kg, Group 3 were administered 500 mg/kg and Group 4 were administered 652.8 mg/kg. The maximum M1P dose administered (Group 4) was 47.1 mg/kg M1P. The Group 4 dose was at the maximum feasible dose volume of 10 ml/kg. A 24-hour observation period was maintained before proceeding to subsequent dosing groups. No clinical effects were observed at any concentration. One group of three females received the maximum dose of 652.8 mg/kg lipid. No clinical effects were observed. Blood was drawn from all animals seven days after administration for clinical chemistry and hematology analysis. In males, a small dose-dependent increase in both red blood cells and platelets was observed. Results are summarized in Table 3. A similar protocol was used for dosing of rats with Lipo-M1P (N-C12-DOPE/DOPC/DSPE-PEG/M1P; lipid ratio: 69.6:27.4:3) for which the maximum feasible dose was 864.2 mg/kg (10 ml/kg dose volume of 86.42 mg/ml lipid) and no adverse clinical effects were observed at any dose. Clinical pathology results are summarized in Table 3.

TABLE 3

Summary of major clinical pathology findings of dose escalation phase

| | N-C12-DOPE/DOPC/DSPE-PEG | DOPE/DOPC/DSPE-PEG |
|---|---|---|
| Doses | 69.6:27.4:3<br>Males: 100, 250, 500, 864.2 mg/kg<br>Females: 864.2 mg/kg only | 48.5:48.5:3<br>Males: 100, 250, 500, 652.8 mg/kg<br>Females: 652.8 mg/kg only |
| Death | 1 male at 864.2 mg/kg (unknown case) | none |
| Clinical Observations | none | none |
| Hematology | In males, dose-dependent increase in red blood cell distribution width (RDW) (15.7 to 18.75%)<br>In females, RDW outside normal range (17.6% vs highest value of 13.7% in historical control data)<br>In males, dose-dependent increase in platelets (648 × 10^3/uL to 1556 × 10^3/uL) | In males, dose-dependent increase in RBCs (6.2 × 10^6/uL to 6.5 × 10^6/uL)<br>In males, dose-dependent increase in platelets (1115 × 10^3/uL to 1273 × 10^3/uL) |
| Coagulation | In males, dose-dependent increase in activated prothrombin time (11.35 to 14.45 sec) | none |

TABLE 3-continued

Summary of major clinical pathology findings of dose escalation phase

| | N-C12-DOPE/DOPC/DSPE-PEG | DOPE/DOPC/DSPE-PEG |
|---|---|---|
| Clinical Chemistry | In males, dose-dependent decrease in ALT (67.3 to 46 U/L)<br>In males, wide variation in Creatine Kinase (424.7 to 2387 U/L) but not dose-dependent | In males, ALT decreased from 70.3 U/L at lowest dose to ≤58 U/L at all higher doses<br>In males, wide variation in Creatine Kinase (322 to 3880 U/L) but not dose-dependent |

A repeat dose study was performed using Lipo-M1P at a lipid concentration of 62 mg/ml. One group of three males and three females each received a daily IV bolus injection at 620 mg/kg lipid (34.3 mg/kg M1P) for seven consecutive days. This dose represented the maximum feasible dose volume of 10 ml/kg. No clinical effects were observed during the dosing phase. One day after the final dose administration blood was drawn for clinical chemistry and hematology analysis and necropsy examinations were performed. No visible lesions were observed. Clinical pathology results are summarized in Tables 4 and 5.

TABLE 4

Summary of key clinical chemistry findings of repeated Lipo-M1P dose phase

| | Male 1 | Male 2 | Male 3 | Normal Range | 95% Spread (Normal Range) | Female 1 | Female 2 | Female 3 | Normal Range | 95% Spread (Normal Range) |
|---|---|---|---|---|---|---|---|---|---|---|
| Sodium (mEq/L) | 140 | 136 | 133 | 123-151 | 139-147 | N.D. | 136 | 139 | 125-148 | 137-146 |
| Phosphorus (mg/dL) | 11.7 | 13.0 | 11.3 | 6.67-12.25 | 7.03-10.92 | N.D. | 13.9 | 15.0 | 4.9-11.97 | 5.58-9.72 |
| Alkaline phosphatase (U/L) | 383 | 284 | 276 | 73.0-598.6 | 93.0-397.0 | N.D. | 231 | 265 | 38.0-379.0 | 50.0-225.0 |
| Albumin (g/dL) | 2.6 | 2.4 | 2.8 | 2.31-3.59 | 2.67-3.34 | N.D. | 2.8 | 2.6 | 2.22-4.07 | 2.77-3.75 |
| Total protein (g/dL) | 4.5 | 4.1 | 4.6 | 4.54-6.43 | 4.8-6.12 | N.D. | 4.7 | 4.5 | 4.37-7.25 | 4.94-6.71 |
| Cholesterol (mg/dL) | 298 | 491 | 348 | 19.0-149.0 | 32.0-113.0 | N.D. | 311 | 423 | 14.0-132.0 | 38.0-112.0 |

TABLE 5

Summary of key hematology/coagulation findings of repeated Lipo-M1P dose phase

| | Male 1 | Male 2 | Male 3 | Normal Range | 95% Spread (Normal Range) | Female 1 | Female 2 | Female 3 | Normal Range | 95% Spread (Normal Range) |
|---|---|---|---|---|---|---|---|---|---|---|
| White Blood Cells ($10_3$/μl) | 4.04 | 2.59 | N.D. | 1.42-19.95 | 4.89-15.39 | N.D. | 5.53 | 4.93 | 2.58-22.07 | 3.85-13.92 |
| Neutrophils ($10_3$/μl) | 0.54 | 0.21 | N.D. | 0.33-8.02 | 0.58-3.74 | N.D. | 0.75 | 0.42 | 0.29-5.56 | 0.39-2.60 |
| Lymphocytes ($10_3$/μl) | 3.30 | 2.23 | N.D. | 1.05-16.04 | 3.82-12.55 | N.D. | 4.39 | 4.25 | 2.12-16.28 | 2.85-11.60 |
| Hemoglobin ($10_3$/μl) | 12.1 | 12.5 | N.D. | 9.20-17.80 | 12.70-16.10 | N.D. | 11.8 | 12.4 | 6.50-17.40 | 12.00-15.80 |
| Platelets ($10_3$/μl) | 520 | 1028 | N.D. | 496.0-1800.0 | 841.0-1548.0 | N.D. | 1308 | 1447 | 457.0-1968.0 | 858.0-1606.0 |
| Monocytes ($10_3$/μl) | 0.08 | 0.11 | N.D. | 0.04-1.10 | 0.09-0.53 | N.D. | 0.29 | 0.19 | 0.04-0.95 | 0.07-0.46 |

A single dose-ascending study in rats, up to 652.8 mg/kg of Lipo-M1P (i.e. 47.1 mg/kg of M1P) did not show any clinical effect. A repeat dose at 620 mg/kg of Lipo-M1P (i.e. 34.3 mg/kg of M1P) was then performed as daily bolus injections in 3 male and 3 female rats for 7 days. There were no visible clinical manifestations and no visible lesions at necropsy. There was an increase in plasma cholesterol, both in males and in females.

What is claimed is:

1. A pharmaceutical composition comprising:

a liposome comprising:

i) 1,2-dioleoyl-sn-glycero-3-phosphoethanolamine (DOPE), or a salt thereof, present in an amount between about 30 mol % and about 50 mol %;

ii) 1,2-dioleoyl-sn-glycero-3-phosphocholine (DOPC), or a salt thereof, present in an amount between about 45 mol % and about 75 mol %; and iii) 1,2-distearoyl-sn-glycero-3-phosphoethanolamine (DSPE), or a salt thereof, conjugated to polyethylene glycol (PEG), present in an amount between about 0.1 mol % and about 10 mol %; and mannose-1-phosphate or a salt thereof encapsulated in the liposome.

2. A method for delivering mannose-1-phosphate or a salt thereof to a human in need thereof, comprising administering to the human the pharmaceutical composition of claim 1.

3. A method for delivering mannose-1-phosphate or a salt thereof to a cell interior of a subject in need thereof, comprising administering to the subject a pharmaceutical composition of claim 1, wherein at least a portion of the administered composition traverses the cell plasma membrane to deliver the mannose-1-phosphate or a salt thereof to the cell interior.

4. A method for treating a congenital disorder of glycosylation (CDG) in a human in need thereof, comprising administering to the human a pharmaceutical composition of claim 1.

5. The method of claim 4, wherein the congenital disorder of glycosylation (CDG) is a CDG-Ia disorder.

6. A kit comprising:

a pharmaceutical composition of claim 1;

a container; and a label or package insert on or associated with the container.

7. The pharmaceutical composition of claim 1, wherein the DSPE conjugated to PEG is $DSPE\text{-}PEG_{2000}$.

8. The pharmaceutical composition of claim 1, wherein the liposome does not comprise cholesterol or a cholesterol ester.

9. The pharmaceutical composition of claim 1, wherein the concentration of mannose-1-phosphate or a salt thereof in the liposome is from about 2.5 mM to about 5 mM.

10. The pharmaceutical composition of claim 1, wherein the concentration of mannose-1-phosphate or a salt thereof in the liposome is from about 5 mM to about 10 mM.

11. The pharmaceutical composition of claim 1, wherein the liposome has an average particle size of about 0.1 microns.

12. The method of claim 4, wherein the CDG is CDG-1a, CDG-Ie, CDG-Ii, CDG-Ik, CDG-Io, GDG-Ip, or DPM2-CDG.

13. The pharmaceutical composition of claim 1, wherein DOPE, or a salt thereof, is present in an amount between about 40 mol % and about 50 mol %.

14. The pharmaceutical composition of claim 1, wherein DOPC, or a salt thereof, is present in an amount between about 50 mol % and about 75 mol %.

15. The pharmaceutical composition of claim 1, wherein DSPE-PEG, or a salt thereof, is present in an amount between about 1 mol % and about 6 mol %.

16. The pharmaceutical composition of claim 1, wherein the molar ratio of DOPE, or a salt thereof; DOPC, or a salt thereof; and DSPE-PEG, or a salt thereof, is about 30:67:3.

* * * * *